US012728122B2

(12) United States Patent
Jamal

(10) Patent No.: US 12,728,122 B2
(45) **Date of Patent: *Sep. 8, 2026**

(54) TREATMENT OF UROTHELIAL AND KIDNEY CANCERS BY USE OF ENDOTHELIN B RECEPTOR ANTAGONISTS

(71) Applicant: ENB Therapeutics, Inc., New York, NY (US)

(72) Inventor: Sumayah Jamal, New York, NY (US)

(73) Assignee: ENB Therapeutics, Inc., New York, NY (US)

( * ) Notice: Subject to any disclaimer, the term of this patent is extended or adjusted under 35 U.S.C. 154(b) by 1131 days.

This patent is subject to a terminal disclaimer.

(21) Appl. No.: 17/597,553

(22) PCT Filed: Jul. 17, 2020

(86) PCT No.: PCT/US2020/042673

§ 371 (c)(1),
(2) Date: Jan. 11, 2022

(87) PCT Pub. No.: WO2021/011925

PCT Pub. Date: Jan. 21, 2021

(65) Prior Publication Data

US 2022/0265628 A1 Aug. 25, 2022

Related U.S. Application Data

(60) Provisional application No. 62/875,458, filed on Jul. 17, 2019.

(51) Int. Cl.

| | |
|---|---|
| ***A61K 31/00*** | (2006.01) |
| ***A61K 31/4025*** | (2006.01) |
| ***A61K 31/454*** | (2006.01) |
| ***A61K 31/455*** | (2006.01) |
| ***A61K 31/505*** | (2006.01) |
| ***A61K 31/506*** | (2006.01) |
| ***A61K 38/12*** | (2006.01) |
| ***A61K 39/395*** | (2006.01) |
| ***A61K 45/06*** | (2006.01) |
| ***A61P 35/00*** | (2006.01) |
| *A61K 39/00* | (2006.01) |

(52) U.S. Cl.

CPC ........ *A61K 31/454* (2013.01); *A61K 31/4025* (2013.01); *A61K 31/455* (2013.01); *A61K 31/505* (2013.01); *A61K 31/506* (2013.01); *A61K 38/12* (2013.01); *A61K 39/3955* (2013.01); *A61K 45/06* (2013.01); *A61P 35/00* (2018.01); *A61K 2039/545* (2013.01)

(58) Field of Classification Search

CPC .............. A61K 31/454; A61K 31/4025; A61K 31/455; A61K 31/505; A61K 31/506; A61K 38/12; A61K 39/3955; A61K 45/06

See application file for complete search history.

(56) References Cited

U.S. PATENT DOCUMENTS

| | | | |
|---|---|---|---|
| 4,522,811 | A | 6/1985 | Eppstein et al. |
| 4,874,780 | A | 10/1989 | Borretzen et al. |
| 5,496,928 | A | 3/1996 | Ishikawa et al. |
| 6,545,048 | B1 | 4/2003 | Patterson et al. |
| 7,566,452 | B1 | 7/2009 | Schneider et al. |
| 7,713,440 | B2 | 5/2010 | Anderson |
| 7,976,835 | B2 | 7/2011 | Gulati |
| 8,067,000 | B2 | 11/2011 | Schneider et al. |
| 8,597,645 | B2 | 12/2013 | Schneider et al. |
| 9,125,897 | B2 | 9/2015 | Schneider et al. |
| 9,463,201 | B2 | 10/2016 | Alster et al. |
| 10,174,120 | B2 | 1/2019 | Buckanovich et al. |
| 10,435,434 | B2 | 10/2019 | Jamal |
| 10,695,400 | B2 | 6/2020 | Jamal |
| 11,066,442 | B2 | 7/2021 | Jamal |
| 11,338,014 | B2 | 5/2022 | Jamal |
| 12,077,604 | B2 | 9/2024 | Jamal |
| 2006/0122180 | A1 | 6/2006 | Boyle et al. |
| 2008/0102451 | A1 | 5/2008 | Lesniewski et al. |
| 2008/0305147 | A1 | 12/2008 | Macdonald et al. |
| 2009/0005394 | A1 | 1/2009 | Harbeson |
| 2009/0202507 | A1 | 8/2009 | Li et al. |
| 2009/0214518 | A1 | 8/2009 | Buckanovich et al. |
| 2011/0311525 | A1 | 12/2011 | Herbert-Fransen et al. |
| 2013/0216547 | A1 | 8/2013 | Morton et al. |
| 2013/0309253 | A1 | 11/2013 | Schneider et al. |
| 2014/0227260 | A1 | 8/2014 | Zhang |

(Continued)

FOREIGN PATENT DOCUMENTS

| | | | |
|---|---|---|---|
| EP | 0555537 | A2 | 8/1993 |
| WO | 1999018120 | A1 | 4/1999 |

(Continued)

OTHER PUBLICATIONS

Lahav et al ,PNAS 96: 11496-11500 (Year: 1999).*
Wulfing et al, European Urology 47: 593-600, 2005 (Year: 2005).*
U.S. Appl. No. 16/828,895, filed Mar. 24, 2020, U.S. Pat. No. 11,338,014, May 24, 2022, Issued.
U.S. Appl. No. 16/828,907, filed Mar. 24, 2020, Abandoned.
U.S. Appl. No. 17/659,545, filed Apr. 18, 2020, Pending.
Allard, B., et al., Generation and characterization of rendomab-B1, a monoclonal antibody displaying potent and specific antagonism of the human endothelin B receptor, MAbs, 5(1): 56-69 (2013).
American Cancer Society. Cancer Facts & Figures 2015. Atlanta: American Cancer Society (2015).

(Continued)

*Primary Examiner* — Lei Yao
(74) *Attorney, Agent, or Firm* — Antheros Legal Advisors LLP

(57) ABSTRACT

Disclosed herein are deuterated compounds, pharmaceutical compositions thereof, and methods for treating ETBR-related cancers such as urothelial, bladder, and kidney cancers. Also disclosed herein is a delivery system for the controlled, systemic release of at least one deuterated ETBR antagonist, optionally in conjunction with an additional anti-oncologic agent.

14 Claims, 22 Drawing Sheets

(56) References Cited

U.S. PATENT DOCUMENTS

| | | | | |
|---|---|---|---|---|
| 2014/0341916 | A1 | 11/2014 | Polakis et al. | |
| 2015/0190506 | A1 | 7/2015 | Cheung et al. | |
| 2016/0022723 | A1 | 1/2016 | Lee | |
| 2016/0257752 | A1 | 9/2016 | Kim et al. | |
| 2017/0008971 | A1 | 1/2017 | Dennis et al. | |
| 2017/0035836 | A1 | 2/2017 | Jamal | |
| 2018/0030138 | A1 | 2/2018 | Kowanetz | |
| 2018/0037655 | A1 | 2/2018 | Hegde et al. | |
| 2019/0218251 | A1 | 7/2019 | Jamal | |
| 2019/0314444 | A1 | 10/2019 | Jamal | |
| 2019/0345197 | A1* | 11/2019 | Jamal | C07K 5/02 |
| 2020/0268829 | A1 | 8/2020 | Jamal | |
| 2020/0289495 | A1 | 9/2020 | Jamal | |
| 2020/0316046 | A1 | 10/2020 | Jamal | |
| 2020/0316049 | A1 | 10/2020 | Jamal | |
| 2021/0077562 | A1 | 3/2021 | Jamal | |
| 2021/0309694 | A1 | 10/2021 | Jamal | |
| 2022/0257700 | A1 | 8/2022 | Jamal | |
| 2024/0360173 | A1 | 10/2024 | Jamal | |

FOREIGN PATENT DOCUMENTS

| | | | |
|---|---|---|---|
| WO | WO-0067024 | A1 | 11/2000 |
| WO | WO-0100198 | A2 | 1/2001 |
| WO | 2004035057 | A1 | 4/2004 |
| WO | WO-2011019630 | A2 | 2/2011 |
| WO | WO-2013127004 | A1 | 9/2013 |
| WO | WO-2014025837 | A1 | 2/2014 |
| WO | 2015110593 | A1 | 7/2015 |
| WO | WO-2016196381 | A1 | 12/2016 |
| WO | WO-2017024032 | A2 | 2/2017 |
| WO | WO-2017151502 | A1 | 9/2017 |
| WO | WO-2017165491 | A1 | 9/2017 |
| WO | WO-2019140324 | A1 | 7/2019 |
| WO | WO-2019191721 | A1 | 10/2019 |
| WO | WO-2021011925 | A1 | 1/2021 |
| WO | WO2024092239 | A1 | 5/2024 |

OTHER PUBLICATIONS

Asundi, et al. MAPK pathway inhibition enhances the efficacy of an anti-endothelin B receptor drug conjugate by inducing target expression in melanoma. Mol Cancer Ther, 13 (6):1599-610 (2014).
Bacon et al. Serodiagnosis of Lyme disease by kinetic enzyme-linked immunosorbent assay using recombinant VIsE1 or peptide antigens of Borrelia burgdorferi compared with 2-tiered testing using whole-cell lysates. J Infect Dis 187:1187-99 (2003).
Bagnato et al. Endothelin B receptor blockade inhibits dynamics of cell interactions and communications in melanoma cell progression. Cancer Res 64:1436-1443 (2004).
Bagnato et al. Endothelin receptors as novel targets in tumor therapy. J Transl Med 2:16, pp. 1-9 (2004).
Baker et al. Inhibitory effects of deuterium substitution on the metabolism of sevoflurane by the rat. Drug Metabolism and Disposition 21:1170-1171 (1993).
Beatty, G.L., et al. Chimeric receptor T cells are vulnerable to immunosuppressive mechanisms present within the tumor microenvironment, OncoImmunology, 3(11): e970027, (2014).
Bittner et al. Molecular classification of cutaneous malignant melanoma by gene expression profiling. Nature 406:536-540 (2000).
Brosseau, J-P, et al., Development of an efficient strategy for the synthesis of the ETB receptor antagonist BQ-788 and some related analogues, Peptides, 26(8): 1441-1453 (2005).
Buckanovich et al. Endothelin B receptor mediates the endothelial barrier to T cell homing to tumors and disables immune therapy. Nature Medicine 14:28-36. (2008).
Böhm et al. Diffuse melanosis arising from metastatic melanoma: pathogenetic function of elevated melanocyte peptide growth factors. J Am Acad Dermatol 44:747-754 (2001).
Chapman et al. Improved survival with vemurafenib in melanoma with BRAF V600E mutation. New Engl J of Med 364(26):2507-2516 (2011).
Chiriboga et al. Endothelin-1 in the tumor microenvironment correlates with melanoma invasion. Melanoma Research 26(3):236-244 (2016).
ClinicalTrials.gov, NCT00730639 first posted Aug. 8, 2008.
ClinicalTrials.gov, NCT01024231 first posted Dec. 2, 2009.
ClinicalTrials.gov, NCT01295827 first posted Feb. 15, 2011.
ClinicalTrials.gov, NCT01375842 first posted Jun. 17, 2011.
ClinicalTrials.gov, NCT01721772 first posted Nov. 6, 2012.
Coffman et al. Endothelin receptor-A is required for the recruitment of antitumor T cells and modulates chemotherapy induction of cancer stem cells. Cancer Biology & Therapy 14(2):184-192 (2013).
Cruz-Munoz, W., et al., Roles for endothelin receptor B and BCL2A1 in spontaneous CNS metastasis of melanoma, Cancer Res, 72(19): 4909-4919 (2012).
De Tayrac et al. Prognostic significance of EDN/RB, HJURP, p60/CAF-1 and PDLI4, four new markers in high-grade gliomas. PLOS One 8:e73332 (2013).
Deeks, Nivolumab: a review of its use in patients with malignant melanoma. Drugs 74:1233-1239 (2014).
Duraiswamy et al. Therapeutic PD-1 pathway blockade augments with other modalities of immunotherapy T-cell function to prevent immune decline in ovarian cancer. Cancer Research 73:6900-6912. (2013).
Egidy, G., et al. The Endothelin System in Human Glioblastoma, Laboratory Investigation, 80(11): 1681-1689, (2000).
Ehrenreich et al. Potent stimulation of monocytic endothelin-1 production by HIV-1 glycoprotein 120. J Immunol, 150:4601-4609 (1993).
Embers et al. Dominant epitopes of the C6 diagnostic peptide of Borrelia burgdorferi are largely inaccessible to antibody on the parent VISE molecule. Clin Vaccine Immunol 14:931-6 (2007).
Eton, O., et al., "Active Immunotherapy with Ultraviolet B-irradiated Autologous Whole Melanoma Cells plus DETOX in Patients with Metastatic Melanoma", Critical Cancer Research, Vo. 4, pp. 619-627, (Mar. 1998).
Fife et al. Determinants of outcome in melanoma patients with cerebral metastases. J Clin Oncol 22(7): 1293-1300 (2004).
Fukami, T., et al., Synthesis and structure—Activity relationships of 2-Substituted d-Tryptophan-containing peptidic endothelin receptor antagonists: Importance of the C-2 substituent of the d-Tryptophan residue for endothelin A and B receptor subtype selectivity, J Med Chem, 39(12): 2313-2330 (1996).
Fukami, T., et al., Synthesis of 2-substituted d-tryptophan-containing peptide derivatives with endothelin receptor antagonist activity, Bioorg Med Chem Lett, 5(14): 1483-1488 (1995).
Gangadhar et al. Clinical applications of PD-1-based therapy: a focus on pembrolizumab (MK-3475) in the management of melanoma and other tumor types. Oncotargets and Therapy, 8: 929-937 (2015).
Gide, T.N., et al., Primary and acquired resistance to immune checkpoint inhibitors in metastatic melanoma, Clin Cancer Res, 24(6):1260-1270 (2018).
Gray-Schopfer et al. The role of B-RAF in melanoma. Cancer Metastasis Rev 24:165-183 (2005).
Greish, Enhanced permeability and retention of macromolecular drugs in solid tumors: a royal gate for targeted anticancer nanomedicines. J Drug Target 15(7-8): 457-464 (2007).
He, J.X., et al., An efficient preparation of the pseudopeptide endothelin-B receptor selective antagonist BQ-788, J Org Chem, 60: 8262-8266 (1995).
How Significant Can Keytruda Be For Merck? Forbes (3 pgs) (Oct. 2014) http://www.forbes.com/sites/greatspeculations/2014/10/03/how-significant-can-keytruda-be-for-merck/.
Howlader et al. SEER Cancer Statistics Review, 1975-2012, National Cancer Institute. Bethesda, MD. Available at http://seer.cancer.gov/archive/csr/1975_2012/ (4 pgs) (2015).
Huang, X., et al., Transdermal BQ-788/EA@ZnO quantum dots as targeting and smart tyrosinase inhibitors in melanocytes, Mater Sci Eng C Mater Biol Appl, 102: 45-52 (2019).
Imokawa et al. The role of endothelin-1 in epidermal hyperpigmentation and signaling mechanisms of mitogenesis and melanogenesis. Pigment Cell Res 10:218-228 (1997).

(56) References Cited

OTHER PUBLICATIONS

Ishikawa et al. Biochemical and pharmacological profile of a potent and selective endothelin B-receptor antagonist, BQ-788. PNAS USA 91(11): 4892-4896 (1994).
Ishikawa et al. Cyclic pentapeptide endothelin antagonists with high ETA selectivity. Potency- and solubility-enhancing modifications. Journal of Medicinal Chemistry 35(11): 2139-2142 (1992).
Jamal et al. UV-induction of keratinocyte endothelin-1 downregulates E-cadherin in melanocytes and melanoma cells. J Clin Invest 110(4): 443-452 (2002).
Jamal, Endothelin-1 down-regulates E-cadherin in melanocytic cells by apoptosis-independent activation of caspase-8*, J Am Acad Dermatol, 43(4): 703-704 (2000).
Johnstrom et al. Positron emission tomography using 18F-labelled endothelin-1 reveals prevention of binding to cardiac receptors owing to tissue-specific clearance by ETB receptors in vivo. Br J Pharmacol 144(1):115-122 (2005).
Jones, G.W., et al., Understanding immune cells in tertiary lymphoid organ development: It is all starting to come together, Front Immunol. 7: 401 (2016).
Kamino et al. Immunoperoxidase technique modified by counterstain with azure B as a diagnostic aid in evaluating heavily pigmented melanocytic neoplasms. J Cutan Pathol 18:436-439 (1991).
Kandalaft, L.E., et al., Endothelin B receptor, a new target in cancer immune therapy, Clin Cancer Res, 15(14): 4521-4528 (2009).
Karaki et al. Novel antagonist of endothelin ETB1 and ETB2 receptors, BQ-788: effects on blood vessel and small intestine. Biochem Biophys Res Commun. 205:168-173 (1994).
Kim et al. Effective treatment of glioblastoma requires crossing the blood-brain barrier and targeting tumors including cancer stem cells: The promise of nanomedicine. Biochem Biophys Res Commun. 468:485-489 (2015).
Kitadai, T., et al., "Targeting the Expression of Platelet-Derived Growth Factor Receptor by Reactive Stroma Inhibits Growth and Metastasis of Human Colon Carcinoma", American Journal of Pathology, 169:6, pp. 2054-2065 (Dec. 2006).
Lahav et al. An endothelin receptor B antagonist inhibits growth and induces cell death in human melanoma cells in vitro and in vivo. PNAS USA 96(20):11496-11500 (1999).
Lahav et al. Endothelin receptor B inhibition triggers apoptosis and enhances angiogenesis in melanomas, Cancer Res 64: 8945-8953 (2004).
Liang et al. An immunodominant conserved region within the variable domain of VlSE, the variable surface antigen of Borrelia burgdorferi. J Immunol 163:5566-5573 (1999).
Liang et al. Sensitive and specific serodiagnosis of Lyme disease by enzyme-linked immunosorbent assay with a peptide based on an immunodominant conserved region of Borrelia burgdorferi vIsE. J Clin Microbiol 37:3990-6 (1999).
Liu et al. Autocrine endothelin-3/endothelin receptor B signaling maintains cellular and molecular properties of glioblastoma stem cells, Mol Cancer Res, 9(12): 1668-1685 (2011).
Mahoney, K.M., et al., The next immune-checkpoint inhibitors: PD-1/PD-L1 blockade in melanoma, Clin Ther, 37(4): 764-782 (2015).
Mangahas et al. Endothelin-1 induces CXCL1 and CXCL8 secretion in human melanoma cells. J Invest Dermatol 125:307-311 (2005).
Mangahas et al. Endothelin-1 upregulates MCAM in melanocytes. J Invest Dermatol 123:1135-1139 (2004).
Medina et al. Dabrafenib in the treatment of advanced melanoma. Drugs of Today 49(6):377-385 (2013).
Moretti et al. Immunohistochemical evidence of cytokine networks during progression of human melanocytic lesions. Int J Cancer, 84:160-168 (1999).
Nagase, T., et al., Linear peptide ETA antagonists: Rational design and practical derivitization of N-terminal amino- and imino-carboylated tripeptide derivatives, Bioorg Med Chem Lett, 5(13): 1395-1400 (1995).
Nakashima, S., et al., Endothelin B receptor expression in malignant gliomas: the perivascular immune escape mechanism of gliomas, J Neurooncol, 127(1): 23-32 (2016).
Nelson et al. The endothelin axis: emerging role in cancer, Nat Rev Cancer 3(2): 110-116 (2003).
Okada, BQ-788, a selective endothelin ET(B) receptor antagonist. Cardiovascular drug reviews 20(1):53-66 (2002).
Okazawa, M., et al. Endothelin-induced Apoptosis of A375 Human Melanoma Cells, J Biol Chem, 273(20): 12584-12592 (1998).
Ott, P.A., et al., CTLA-4 and PD-1/PD-L1 blockade: new immunotherapeutic modalities with durable clinical benefit in melanoma patients, Clin Cancer Res, 19(19): 5300-5309 (2013).
Pardoll, D.M. The blockade of immune checkpoints in cancer immunotherapy, Nature, 12: 252-264, (2012).
Pardoll, D.M., et al., The blockade of immune checkpoints in cancer immunotherapy, Nat Rev Cancer, 12(4): 252-264 (2012).
Park, J., et al., Immune checkpoint inhibitors for cancer treatment, Arch Pharm Res, 39(11): 1577-1587 (2016).
PCT/US2016/45343 International Search Report and Written Opinion dated Feb. 17, 2017.
PCT/US2019/013377 International Search Report and Written Opinion dated May 8, 2019.
PCT/US2019/013377 Invitation to Pay Additional Fees dated Mar. 12, 2019.
PCT/US2019/025050 International Search Report and Written Opinion dated Aug. 12, 2019.
PCT/US2019/025050 Invitation to Pay Additional Fees dates Jun. 7, 2019.
PCT/US2020/042673 International Search Report and Written Opinion dated Dec. 7, 2020.
Rizvi et al. Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol 16(3):257-265 (2015).
Rosario et al. Endothelin receptor blockade inhibits molecular effectors of Kaposi's sarcoma cell invasion and tumor growth in vivo, Am J Pathol, 163(2): 753-762 (2003).
Ross et al. Systematic variation in gene expression patterns in human cancer cell lines. Nat Genet 24:227-235 (2000).
Saldana-Caboverde et al. Roles in endothelin signaling in melanocyte development and melanoma, Pigment Cell and Melanoma Res. 23(2):160-170 (2010).
Saldanha et al. High BRAF mutation frequency does not characterize all melanocytic tumor types. Int J Cancer 111:705-710 (2004).
Samlowski et al. Management of brain metastases in melanoma, Up to Date literature review. http://www.uptodate.com/contents/management-of-brain-metastases-in-melanoma. (5 pgs) (2016).
Sampson et al. Demographics, prognosis, and therapy in 702 patients with brain metastases from malignant melanoma. J Neurosurg 88:11 (1998).
Sampson, J.H., et al., Randomized phase IIb study of Nivolumab (anti-PD-1; BMS-936558, Ono-4538) alone or in combination with ipilimumab versus bevacizumab in patients (pts) with recurrent glioblastoma (GBM), J Clin Oncol, 32(15): Abstract, (2014).
Sautes-Fridman, C., et al., Tertiary lymphoid structures in the era of cancer immunotherapy, Nat Rev Cancer, 19(6): 307-325 (2019).
Seiwert, T.Y., et al., Antitumor activity and safety of pembrolizumab in patients (pts) with advanced squamous cell carcinoma of the head and neck (SCCHN): Preliminary results from KEYSOTE-012 expansion cohort, J Clin Oncol, 33(18 spp): LBA6008 (Abstract) (2005).
Sharma et al. The future of immune checkpoint therapy. Science 348:56-61 (2015).
Singh, R.K., et al., Organ site-dependent expression of basic fibroblast growth factor in human renal cell carcinoma cells, Am J Pathol, 145(2): 365-374 (1994).
Sosman, Immunotherapy of advanced melanoma with immune checkpoint inhibition, Up to Date literature review. http://www.uptodate.com/contents/immunotherapy-of-advanced-melanoma-with-immune-checkpoint-inhibition. (12 pgs.) (2016).
Sosman, Molecularly targeted therapy for metastatic melanoma, Up to Date Literature review http://www.uptodate.com/contents/molecularly-targeted-therapy-for-metastatic-melanoma. (11 pgs.) (2016).

(56) References Cited

OTHER PUBLICATIONS

Steiniger, S.C.J., et al., Chemotherapy of glioblastoma in rats using doxorubicin-loaded nanoparticles, Int J Cancer, 109: 759-767 (2004).
Takahashi, Molecular-target therapy for advanced malignant melanoma. Japanese Journal of Cancer and Chemotherapy 40(1):19-25 (2013) (English Summary).
Tang et al. Endothelin-3 is produced by metastatic melanoma cells and promotes melanoma cell survival, J Cutan Med and Surg, 12(2): 64-70 (2008).
Terrades-Garcia et al. Pathogenesis of giant-cell arteritis: how targeted therapies are influencing our understanding of the mechanisms involved. Rheumatology (Oxford) 57(supp 2):ii51-ii62 (2018).
Topalian et al. Immune checkpoint blockade: a common denominator approach to cancer therapy. Cancer Cell 27:450-461 (2015).
U.S. Appl. No. 15/227,792 Office Action dated Nov. 15, 2019.
U.S. Appl. No. 15/227,792 Office Action dated Sep. 21, 2018.
U.S. Appl. No. 16/246,398 First Action Interview dated Apr. 8, 2019.
U.S. Appl. No. 16/419,931 Office Action dated Jan. 13, 2020.
U.S. Appl. No. 16/419,931 Office Action dated Jul. 24, 2020.
U.S. Appl. No. 16/526,862 Office Action dated Jan. 7, 2021.
U.S. Appl. No. 16/828,895 Office Action dated Dec. 2, 2020.
U.S. Appl. No. 16/828,895 Office Action dated Jun. 30, 2020.
U.S. Appl. No. 16/828,895 Office Action dated Mar. 3, 2021.
U.S. Appl. No. 16/828,895 Office Action dated Sep. 15, 2021.
U.S. Appl. No. 16/828,900 Office Action dated Jun. 25, 2020.
U.S. Appl. No. 16/828,900 Office Action dated Nov. 10, 2020.
U.S. Appl. No. 16/828,911 Office Action dated Dec. 1, 2020.
U.S. Appl. No. 16/828,911 Office Action dated May 29, 2020.
U.S. Appl. No. 17/350,497, filed Jun. 17, 2021.
Voronin, K., Deuteriodesilylation: a mild and selective method for the site-specific incorporation of deuterium into drug candidates and pharmaceutical structures. Thesis (132 pgs) (2012).
Yohn, J.J., et al. Human melanoma cells express functional endothelin-1 receptors, Biochem Biophys Res Commun, 201:449-457 (1994).
U.S. Appl. No. 17/101,676 Office Action dated Oct. 6, 2022.
U.S. Appl. No. 15/227,792 10,695,400, filed Aug. 3, 2016, U.S. Pat. No. 10,695,400, Jun. 30, 2020, Issued.
U.S. Appl. No. 16/828,900, filed Mar. 24, 2020, Abandoned.
U.S. Appl. No. 16/828,895, filed Mar. 24, 2020, Pending.
U.S. Appl. No. 16/828,907, filed Mar. 24, 2020, Pending.
U.S. Appl. No. 16/828,911, filed Mar. 24, 2020, Abandoned.
U.S. Appl. No. 16/246,398, filed Jan. 11, 2019, U.S. Pat. No. 10,435,434, Oct. 8, 2019, Issued.
U.S. Appl. No. 16/526,862, filed Jul. 30, 2019, U.S. Pat. No. 11,066,442, Jul. 20, 2021, Issued.
U.S. Appl. No. 17/350,497, filed Jun. 17, 2021, Pending.
U.S. Appl. No. 16/419,931, filed May 22, 2019, Abandoned.
U.S. Appl. No. 17/101,676, filed Nov. 23, 2020, Pending.
Budi, H.S., et al., Human Epidermal Growth Factor Receptor 2 (HER2)-Specific Chimeric Antigen Receptor (CAR) for Tumor Immunotherapy; Recent Progress, Stem Cell Research & Therapy, 13(40): 1-21 (2022).
Davuluri, S., API Manufacture of Deuterated Molecules, retrieved from https://www.neulandlabs.com/blog/2016/12/04/api-manufacture-deuterated-molecules, pp. 1-3 (2016).
Lin Z., et al., PD-1 Antibody Monotherapy for Malignant Melanoma: A Systematic Review and Meta-Analysis, PLoS One, vol. 11, No. 8 (e0160485 ), 13 Pages (2018).
Lin, Z., et al., PD-1 Antibody Monotherapy for Malignant Melanoma: A Systematic Review and Meta-Analysis, PLOS ONE, 11(8): e0160485, (13 Pages) (2016).
Pardoll D.M., et al., The Blockade of Immune Checkpoints in Cancer Immunotherapy, Nature, vol. 12, pp. 252-264 (2012).
PCT/US2023/078095 International Search Report and Written Opinion dated Mar. 5, 2024, 12 Pages.
Peng, W., et al., PD-1 Blockade Enhances T-Cell Migration to Tumors by Elevating IFN-(gamma) Inducible Chemokines, Cancer Research, 72(20): 5209-5218 (17 Pages) (2012).
Pimenta, E.M., et al., Role of Tertiary Lymphoid Structures (TLS) in Anti-Tumor Immunity: Potential Tumor-Induced Cytokines/Chemokines that Regulate TLS Formation in Epithelial-Derived Cancers, Cancers (Basel), 6(2): 969-997 (2014).
Seiwert, T.Y., et al., Antitumor Activity and Safety of Pembrolizumab in Patients (pts) With Advanced Squamous Cell Carcinoma of the Head and Neck (SCCHN): Preliminary Results from KEYNOTE-012 Expansion Cohort, Journal of Clinical Oncology, 33(18): LBA6008 (Abstract) 3 Pages, (2015).
Toth, G., et al., A Small Number of HER2 Redirected CAR T Cells Significantly Improves Immune Response of Adoptively Transferred Mouse Lymphocytes against Human Breast Cancer Xenografts, International Journal of Molecular Sciences, 21(3), (1039): 1-10 (2020).
Montgomery, J.P., et al., Endothelin Receptor B Antagonists Decrease Glioma Cell Viability Independently of Their Cognate Receptor, BMC Cancer, Biomed Central, London, GB, 8(354): 1-10 (2008).

* cited by examiner

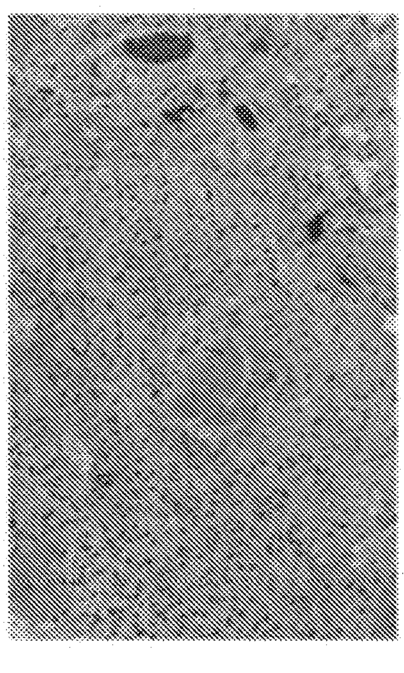
FoxP3
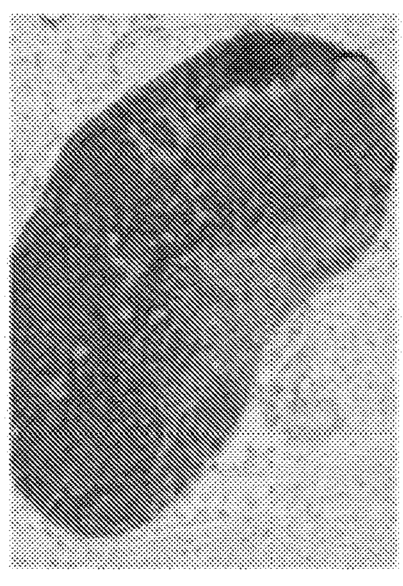
CD4
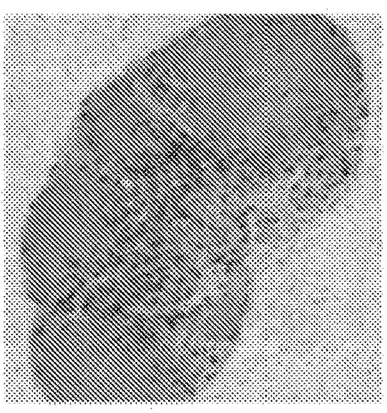
CD8
FIG. 10

| | Group # | Animal # | TLO formation | Tumor eradiction |
|---|---|---|---|---|
| control | Group 1 | 6 | no | no |
| | | 23 | no | no |
| | | 28 | no | no |
| | | 29 | no | no |
| | | 33 | no | no |
| D+P | Group 2 | 3 | no | no |
| | | 10 | no | no |
| | | 17 | tlo peripheral | no |
| | | 32 | no | no |
| | | 35 | no | no |
| D+P+B (0.6 μg) | Group 3 | 5 | no | no |
| | | 13 | no | no |
| | | 20 | tumor undetectable | |
| | | 24 | no | no |
| | | 31 | no | 25% |

| | Group # | Animal # | TLO formation | Tumor eradiction |
|---|---|---|---|---|
| D+P+B (4.0 μg) | Group 4 | 1 | no | no |
| | | 19 | tlo peripheral | no |
| | | 21 | no | no |
| | | 26 | tlo peripheral | no |
| | | 27 | tlo internal | 90% |
| D+P+B (100 μg) | Group 5 | 8 | no | no |
| | | 14 | tlo internal | 80% |
| | | 16 | no | no |
| | | 22 | no | no |
| | | 25 | no | no |
| P+B (4.0 μg) | Group 6 | 7 | tumor undetectable | |
| | | 9 | tlo internal | 90% |
| | | 12 | no | 100% |
| | | 38 | tlo internal | 90% |
| | | 40 | tlo internal | 50% |

D = dabrafenib
P = immunocheckpoint inhibitor
B = BQ-788-B (compound 1) (dosage)

*FIG. 11*

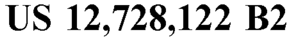
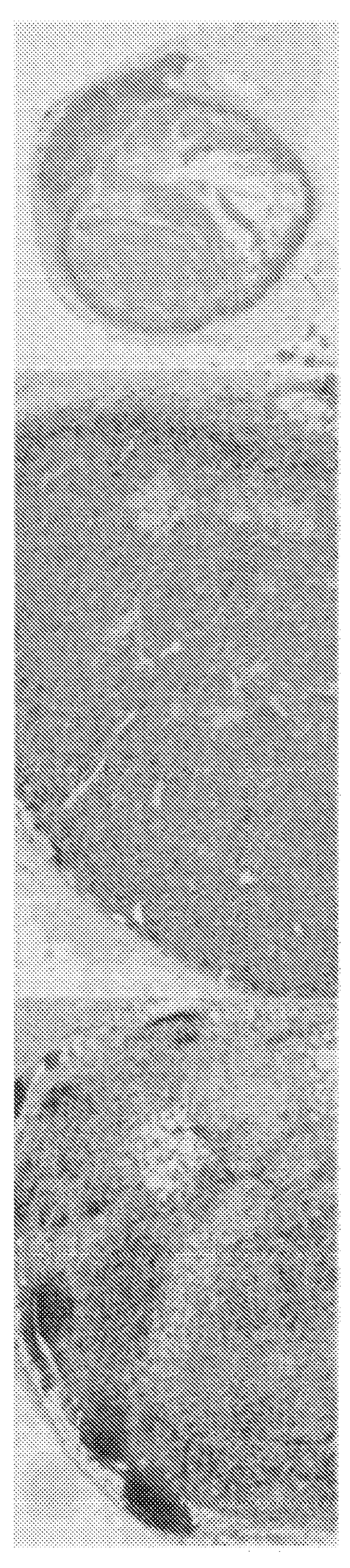
D = dabrafenib
P = immunocheckpoint inhibitor
B = BQ-788-B (Compound 1) (dosage)
*FIG. 13*

A B C D E 13

1 2 3 4 5 6 7 8 9 10

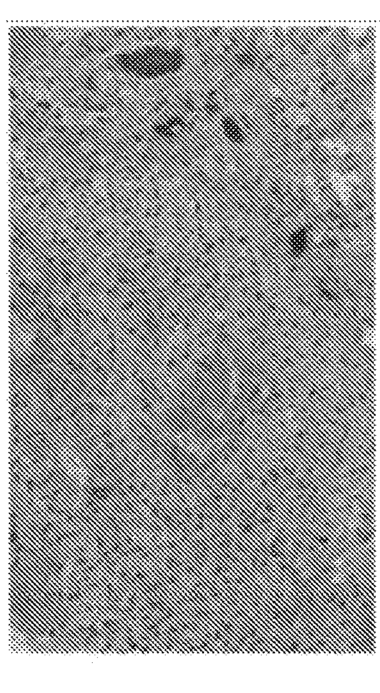
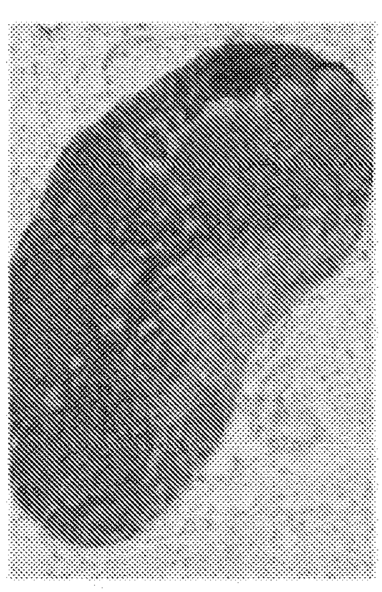
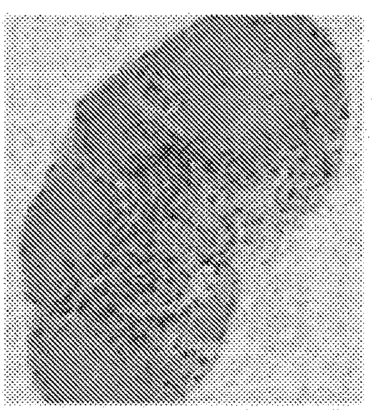
FIG. 20

TREATMENT OF UROTHELIAL AND KIDNEY CANCERS BY USE OF ENDOTHELIN B RECEPTOR ANTAGONISTS

CROSS-REFERENCE

This application is the U.S. National Stage entry of International Application No. PCT/US2020/042673, filed Jul. 17, 2020, which claims the benefit of U.S. Provisional Application No. 62/875,458, filed Jul. 17, 2019; each of which are incorporated herein by reference in their entireties.

SUMMARY OF THE CLAIMS

In certain embodiments, provided herein are compositions for and methods of treating urothelial or kidney cancer in a subject in need thereof. In some embodiments, provided herein are methods of treating urothelial or kidney cancer in a subject in need thereof, comprising administering to the subject an endothelin B receptor (ETBR) antagonist, wherein said administering is effective to treat said urothelial or kidney cancer. In some embodiments the urothelial cancer is bladder cancer. In some embodiments, the ETBR antagonist is BQ-788, A192621, A-308165, IRL-1038, IRL-2500, RO-468443, BQ-017, or a structural analog thereof. In some embodiments, the ETBR antagonist is BQ-788 or a structural analog thereof. In some embodiments, the ETBR antagonist is:

Formula (1)

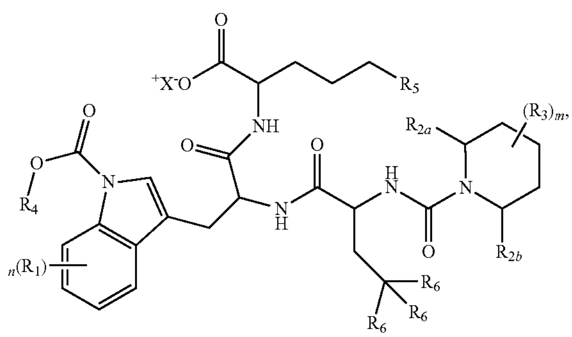

a stereoisomer thereof, or a pharmaceutically acceptable salt thereof, wherein: n is an integer from 0-4; m is an integer from 0-3; X is a positively charged counterion; $R_1$ and $R_3$ are independently —H, -D, —$CH_3$, —$CH_2D$, —$CHD_2$, or —$CD_3$; $R_{2a}$, $R_{2b}$, $R_4$, $R_5$, and $R_6$ are independently —$CH_3$, —$CH_2D$, —$CHD_2$, or —$CD_3$; and at least one of $R_1$, $R_{2a}$, $R_{2b}$, and $R_3$ comprises deuterium. In some embodiments, m is 0, n is 0, and $R_{2a}$ and $R_{2b}$ are —$CH_2D$ in said Formula 1. In some embodiments, the ETBR antagonist of Formula I is:

Formula (2)

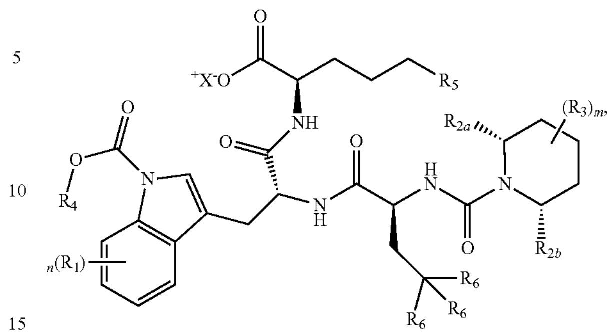

or a pharmaceutically acceptable salt thereof. In some embodiments, the ETBR antagonist of Formula I is:

Formula (3)

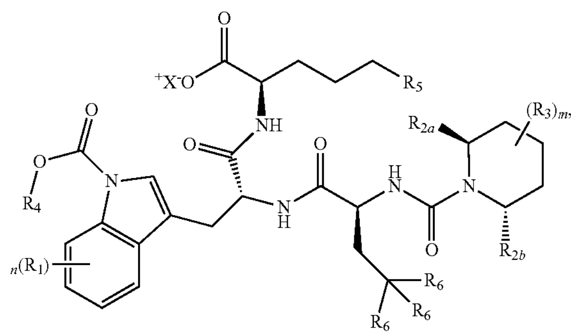

or a pharmaceutically acceptable salt thereof. In some embodiments, the ETBR antagonist of Formula I is:

Formula (4)

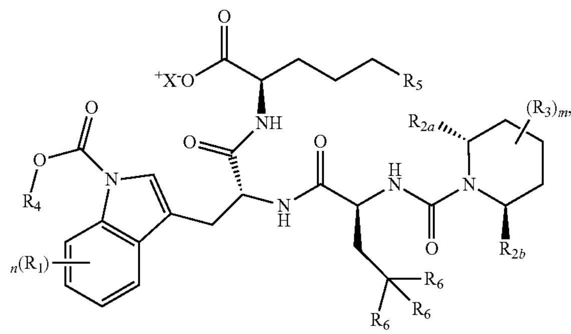

or a pharmaceutically acceptable salt thereof. In some embodiments, the ETBR antagonist of Formula I is:

Formula (5)

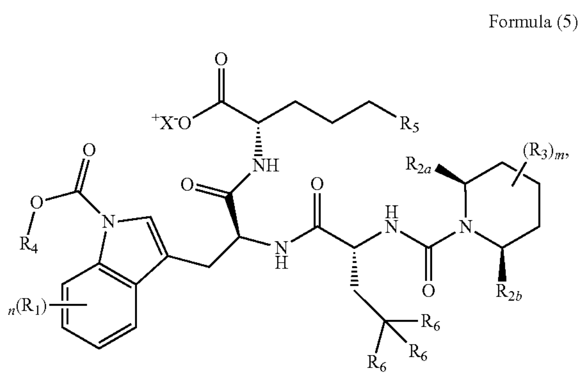

or a pharmaceutically acceptable salt thereof.

In some embodiments, the ETBR antagonist is:

Formula (6)

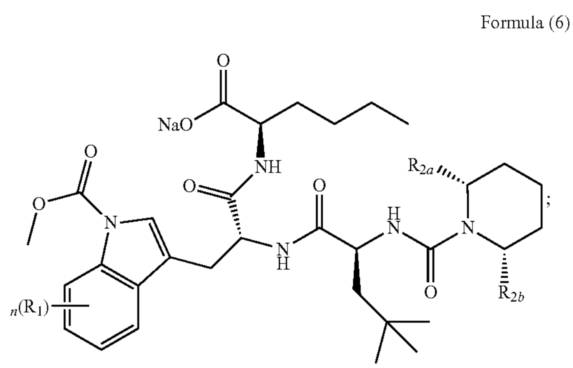

or a pharmaceutically acceptable salt thereof, and wherein n is 0 or 1 in Formula 6. In some embodiments, n is 1, $R_1$ is -D; and $R_{2a}$ and $R_{2b}$ are —$CH_3$ in Formula 6. In some embodiments, n is 0, $R_1$ is —H; $R_{2a}$ is —$CH_3$ and $R_{2b}$ is —$CH_2D$ in Formula 6. In some embodiments, n is 0, $R_1$ is —H; $R_{2a}$ is —$CH_2D$ and $R_{2b}$ is —$CH_3$ in Formula 6. In some embodiments, n is 0, $R_1$ is —H; and $R_{2a}$ and $R_{2b}$ are —$CH_2D$ in Formula 6. In some embodiments, n is 1, $R_1$ is -D; and $R_{2a}$ and $R_{2b}$ are —$CH_2D$ in formula 6. In some embodiments, the ETBR antagonist is Compound (1)

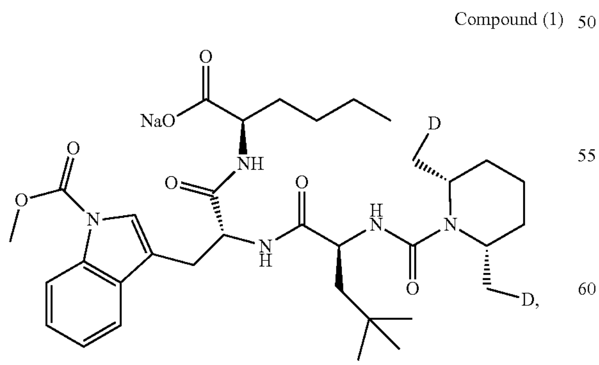

or a pharmaceutically acceptable salt thereof. In some embodiments, the ETBR antagonist is formulated as a controlled, or delayed release formulation. In some embodiments, the ETBR antagonist is formulated as nanoparticles. In some embodiments, the ETBR antagonist is a deuterated BQ-788 analog. In some embodiments, the ETBR antagonist is a non-deuterated BQ-788 analog.

In some embodiments, a method described herein further comprises administering to the subject an additional therapeutic agent. In some embodiments, the additional therapeutic agent is an anti-oncologic, an anti-bacterial, an anti-viral, or an anti-microbial agent. In some embodiments, the additional therapeutic agent is an anti-oncologic agent which is, for instance, an immunotherapy agent. In some embodiments, the anti-oncologic agent is selected from a bRAF inhibitor, an immune checkpoint inhibitor, a caspase-8 inhibitor, an endothelin A receptor (ETAR) antagonist, niacinamide, a chemotherapeutic agent, or any combination thereof. In some embodiments, the anti-oncologic agent is an immune checkpoint inhibitor. In some embodiments, the immune checkpoint inhibitor is an anti-PD1 antibody, anti-PD-L1 antibody, anti-CTLA4 antibody, or a variant or functional fragment thereof. In some embodiments, the anti-PD1 antibody is selected from pidilizumab, BMS-936559, nivolumab, pembrolizumab, or a variant or functional fragment thereof. In some embodiments, the anti-PD-L1 antibody is selected from atezolizumab, avelumab, durvalumab, MDX-1105, or a variant or functional fragment thereof. In some embodiments, the immunotherapy agent is an engineered cell, for instance a CAR-T cell or a T cell engineered to express a specific αβ or γδ TCR.

In some embodiments, a greater reduction in volume of a urothelial or kidney cancer is observed in the subject upon administration of the immunotherapy (e.g. immune checkpoint inhibitor) and the ETBR antagonist as compared to the reduction in volume of a urothelial or kidney cancer upon individual administration of the ETBR antagonist, absent the immunotherapy (e.g. immune checkpoint inhibitor) or the immunotherapy (e.g. immune checkpoint inhibitor) absent the ETBR antagonist. In some embodiments, at least a 1-fold or 2-fold reduction in volume of the urothelial or kidney cancer is observed in the subject upon administration of the immunotherapy (e.g. immune checkpoint inhibitor) and the ETBR antagonist as compared to the reduction in volume of a urothelial or kidney cancer upon individual administration of an ETBR antagonist, absent an immunotherapy (e.g. immune checkpoint inhibitor) or an immunotherapy (e.g. immune checkpoint inhibitor) absent an ETBR antagonist. In some embodiments, extended survival of the subject is observed upon administration of immunotherapy (e.g. immune checkpoint inhibitor) and ETBR antagonist as compared to the survival of the subject upon individual administration of the ETBR antagonist, absent the immunotherapy (e.g. immune checkpoint inhibitor) or the immunotherapy (e.g. immune checkpoint inhibitor) absent the ETBR antagonist. In some embodiments, survival of the subject is extended by at least 1 month, 3 months, 6 months, or 1 year upon administration of the immune checkpoint inhibitor and the ETBR antagonist as compared to the extended survival upon individual administration of the ETBR antagonist, absent the immune checkpoint inhibitor or the immune checkpoint inhibitor absent the ETBR antagonist. In some embodiments, the ETBR antagonist and the additional therapeutic agent are administered sequentially or simultaneously. In some embodiments, the ETBR antagonist is administered at 2, 3, 4, or 5 times the frequency of the additional therapeutic agent. In some embodiments, the ETBR antagonist is administered 3 times about every 2-3 weeks and the additional therapeutic agent is administered 1 time about every 2-3 weeks. In some embodiments, the ETBR antagonist is administered 3 times about every 21 days and the additional therapeutic agent is administered 1 time about every 21 days. In some embodiments, administering of the ETBR antagonist provided herein or the additional therapeutic agent provided herein is performed orally, intravenously, intravesically, intrathecally, intracavernously, intramuscularly, topically, via inhalation, rectally, intradermally, or any combination thereof.

In some embodiments, the subject has at least one of: hematuria, pain during urination, a burning sensation during urination, frequent urination, urgency to urinate, inability to pass urine, unilateral back pain, or a combination thereof. In some embodiments, the subject has kidney cancer. In some embodiments, the subject has a urothelial cancer. In some embodiments, the urothelial cancer is bladder cancer, ureter cancer, renal pelvic cancer, or any combination thereof. In some embodiments, the urothelial cancer is bladder cancer. In some embodiments, bladder cancer is urothelial carcinoma, squamous cell carcinoma, adenocarcinoma, small cell carcinoma, sarcoma, and any combination thereof. In some embodiments, the cancer is a refractory cancer, or resistant to immunotherapy.

Provided herein, in certain embodiments, are methods of treating urothelial or kidney cancer in a subject in need thereof comprising administering to said subject (a) an endothelin B receptor (ETBR) antagonist; and (b) an immunotherapy, for instance an immune checkpoint inhibitor, wherein said administering is effective to treat said urothelial or kidney cancer in said subject. In some embodiments, the ETBR antagonist is BQ-788, A192621, A-308165, IRL-1038, IRL-2500, RO-468443, BQ-017, or a structural analog thereof. In some embodiments, the ETBR antagonist is BQ-788 or a structural analog thereof. In some embodiments, the ETBR antagonist is:

Formula (1)

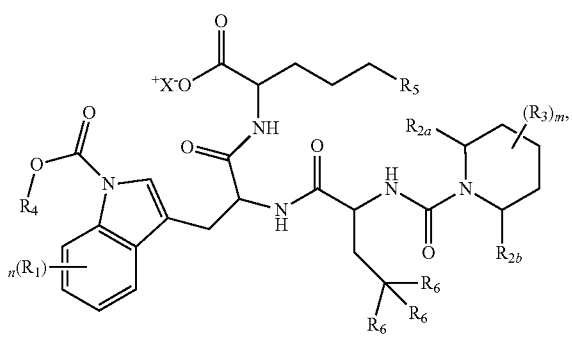

a stereoisomer thereof, or a pharmaceutically acceptable salt thereof, wherein: n is an integer from 0-4; m is an integer from 0-3; X is a positively charged counterion; $R_1$ and $R_3$ are independently —H, -D, —$CH_3$, —$CH_2D$, —$CHD_2$, or —$CD_3$; $R_{2a}$, $R_{2b}$, $R_4$, $R_5$, and $R_6$ are independently —$CH_3$, —$CH_2D$, —$CHD_2$, or —$CD_3$; and at least one of $R_1$, $R_{2a}$, $R_{2b}$, and $R_3$ comprises deuterium. In some embodiments, m is 0, n is 0, and $R_{2a}$ and $R_{2b}$ are —$CH_2D$ in said Formula 1. In some embodiments, the ETBR antagonist is:

Formula (2)

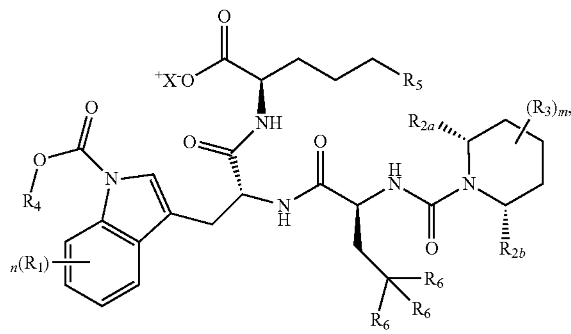

or a pharmaceutically acceptable salt thereof. In some embodiments, the ETBR antagonist is:

Formula (3)

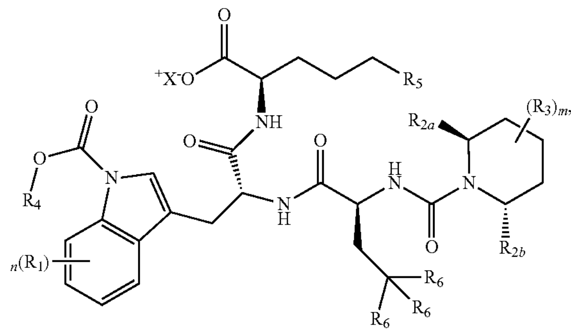

or a pharmaceutically acceptable salt thereof. In some embodiments, the ETBR antagonist is:

Formula (4)

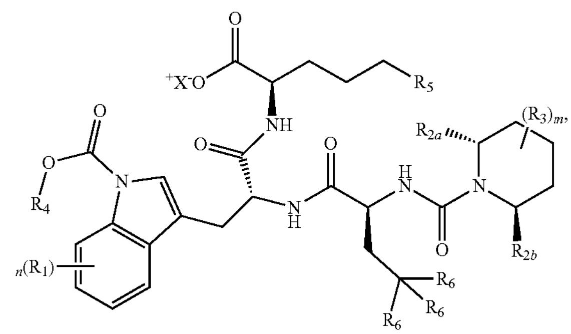

or a pharmaceutically acceptable salt thereof. In some embodiments, the ETBR antagonist is:

Formula (5)

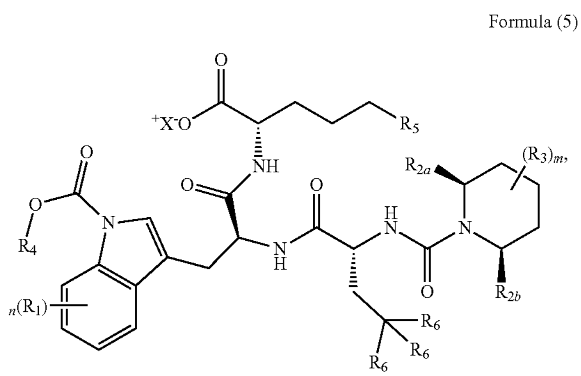

or a pharmaceutically acceptable salt thereof. In some embodiments, the ETBR antagonist is:

Formula (6)

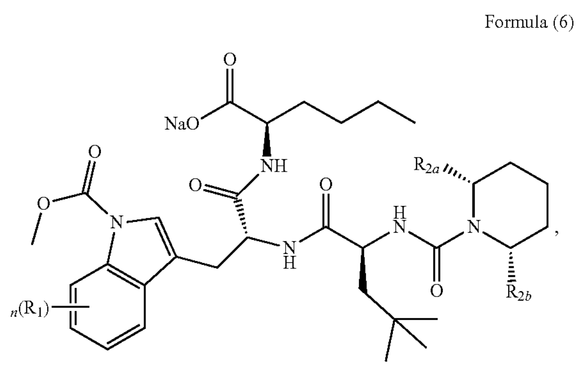

or a pharmaceutically acceptable salt thereof. In some embodiments, n is 0 or 1 in Formula 6. In some embodiments, n is 1, $R_1$ is -D; and $R_{2a}$ and $R_{2b}$ are —$CH_3$ in formula 6. In some embodiments, n is 0, $R_1$ is —H; $R_{2a}$ is —$CH_3$ and $R_{2b}$ is —$CH_2D$ in Formula 6. In some embodiments, n is 0, $R_1$ is —H; $R_{2a}$ is —$CH_2D$ and $R_{2b}$ is —$CH_3$ in formula 6. In some embodiments, n is 0, $R_1$ is —H; and $R_{2a}$ and $R_{2b}$ are —$CH_2D$ in formula 6. In some embodiments, n is 1, $R_1$ is -D; and $R_{2a}$ and $R_{2b}$ are —$CH_2D$ in formula 6. In some embodiments, the ETBR antagonist is:

Compound (1)

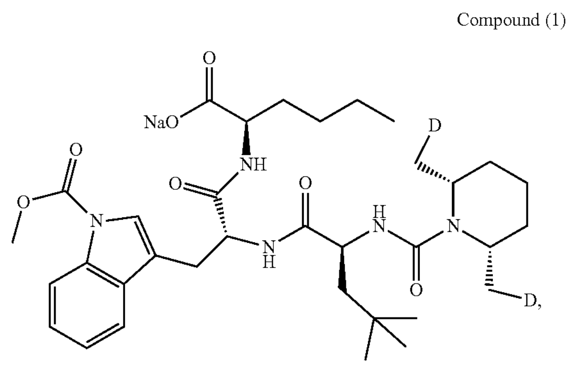

or a pharmaceutically acceptable salt thereof. In some embodiments, the ETBR antagonist is formulated as a controlled or delayed release formulation. In some embodiments, the ETBR antagonist is formulated as nanoparticles.

In some embodiments, the ETBR antagonist for use in a method described herein is a deuterated BQ-788 analog. In some embodiments, the ETBR antagonist is a non-deuterated BQ-788 analog. In some embodiments, a greater reduction in volume of a urothelial or kidney cancer is observed in a subject upon administration of said immune checkpoint inhibitor and the ETBR antagonist as compared to the reduction in volume of the urothelial or kidney cancer upon individual administration of the ETBR antagonist, absent the immune checkpoint inhibitor or the immune checkpoint inhibitor absent the ETBR antagonist. In some embodiments, an at least 1-fold or 2-fold reduction in volume of the urothelial or kidney cancer is observed in the subject upon administration of the immune checkpoint inhibitor and the ETBR antagonist as compared to the reduction in volume of the urothelial or kidney cancer upon individual administration of the ETBR antagonist, absent the immune checkpoint inhibitor or the immune checkpoint inhibitor absent the ETBR antagonist. In some embodiments, extended survival of the subject is observed upon administration of the immune checkpoint inhibitor and the ETBR antagonist as compared to the survival of the subject upon individual administration of the ETBR antagonist, absent the immune checkpoint inhibitor or the immune checkpoint inhibitor absent the ETBR antagonist. In some embodiments, extended survival of the subject is extended by at least 1 month, 3 months, 6 months, or 1 year upon administration of the immune checkpoint inhibitor and the ETBR antagonist as compared to the extended survival upon individual administration of the ETBR antagonist, absent the immune checkpoint inhibitor or the immune checkpoint inhibitor absent the ETBR antagonist. In some embodiments, the method further comprises administering to the subject an additional therapeutic agent. In some embodiments, the additional therapeutic agent is an anti-oncologic, an anti-bacterial, an anti-viral, or an anti-microbial. In some embodiments, the additional therapeutic agent is an anti-oncologic. In some embodiments, the anti-oncologic is selected from a bRAF inhibitor, a caspase-8 inhibitor, an endothelin A receptor (ETAR) antagonist, niacinamide, a chemotherapeutic agent, or any combination thereof. In some embodiments, a) and b) are administered sequentially. In some embodiments, a) and b) are administered simultaneously. In some embodiments, the ETBR antagonist is administered at 2, 3, 4, or 5 times the frequency of the immune checkpoint inhibitor. In some embodiments, the ETBR antagonist is administered 3 times about every 2-3 weeks and the additional therapeutic agent is administered 1 time about every 2-3 weeks. In some embodiments, the ETBR antagonist is administered 3 times about every 21 days and the additional therapeutic agent is administered 1 time about every 21 days. In some embodiments, the administering is orally, intravenously, intravesically, intrathecally, intracavernously, intramuscularly, topically, via inhalation, rectally, intradermally, or any combination thereof.

In some embodiments, the subject has at least one of: hematuria, pain during urination, a burning sensation during urination, frequent urination, urgency to urinate, inability to pass urine, unilateral back pain, or a combination thereof. In some embodiments, the subject has kidney cancer. In some embodiments, the subject has a urothelial cancer. In some embodiments, the urothelial cancer is bladder cancer, ureter cancer, renal pelvic cancer, or any combination thereof. In some embodiments, the urothelial cancer is bladder cancer. In some embodiments, bladder cancer is urothelial carcinoma, squamous cell carcinoma, adenocarcinoma, small cell carcinoma, sarcoma, and any combination thereof. In some embodiments, the cancer is a refractory cancer, or resistant to immunotherapy.

Provided herein, in certain embodiments, are methods of forming a tertiary lymphoid organ (TLO) within a urothelial or kidney cancer in a subject in need thereof. In some embodiments, provided herein are methods of forming a tertiary lymphoid organ (TLO) within a urothelial or kidney cancer in a subject in need thereof, comprising administering to said subject an ETBR antagonist. In some embodiments, the ETBR antagonist is BQ-788, A192621, A-308165, IRL-1038, IRL-2500, RO-468443, BQ-017, or a structural analog thereof. In some embodiments, the ETBR antagonist is BQ-788 or a structural analog thereof. In some embodiments, the ETBR antagonist is:

Formula (1)

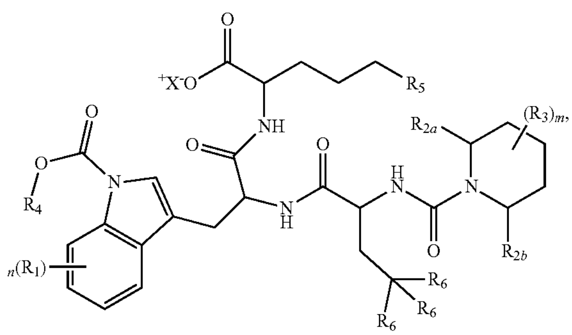

a stereoisomer thereof, or a pharmaceutically acceptable salt thereof, wherein: n is an integer from 0-4; m is an integer from 0-3; X is a positively charged counterion; $R_1$ and $R_3$ are independently —H, -D, —$CH_3$, —$CH_2D$, —$CHD_2$, or —$CD_3$; $R_{2a}$, $R_{2b}$, $R_4$, $R_5$, and $R_6$ are independently —$CH_3$, —$CH_2D$, —$CHD_2$, or —$CD_3$; and at least one of $R_1$, $R_{2a}$, $R_{2b}$, and $R_3$ comprises deuterium. In some embodiments, m is 0, n is 0, and $R_{2a}$ and $R_{2b}$ are —$CH_2D$ in said Formula 1. In some embodiments, the ETBR antagonist of Formula I is:

Formula (2)

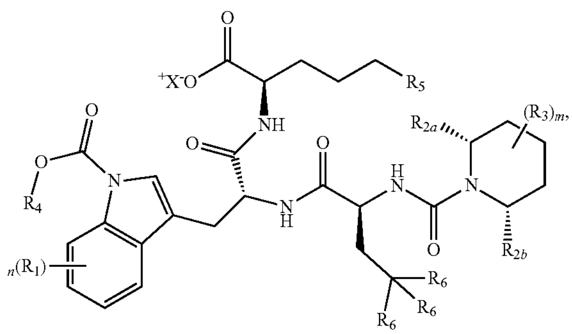

or a pharmaceutically acceptable salt thereof. In some embodiments, the ETBR antagonist is:

Formula (3)

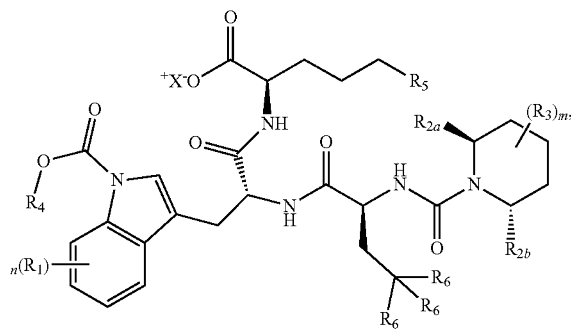

or a pharmaceutically acceptable salt thereof. In some embodiments, the ETBR antagonist of Formula I is:

Formula (4)

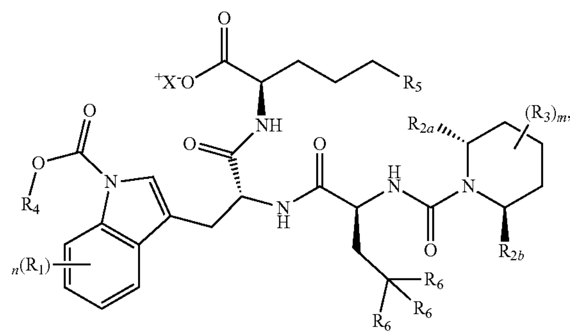

or a pharmaceutically acceptable salt thereof. In some embodiments, the ETBR antagonist of Formula I is:

Formula (5)

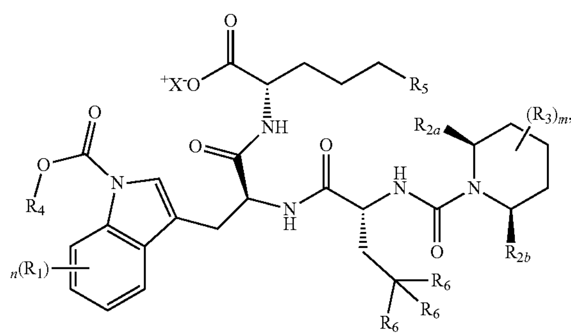

or a pharmaceutically acceptable salt thereof. In some embodiments, the ETBR antagonist of Formula I is:

Formula (6)

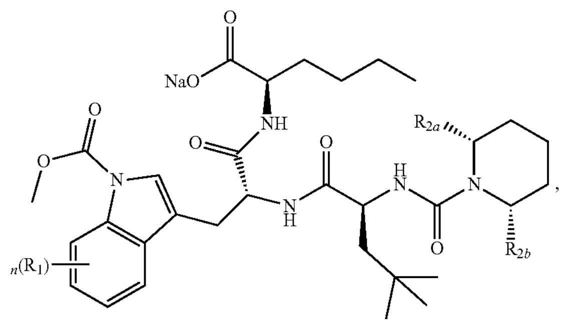

or a pharmaceutically acceptable salt thereof. In some embodiments, n is 0 or 1 in Formula 6. In some embodiments, n is 1, $R_1$ is -D; and $R_{2a}$ and $R_{2b}$ are —$CH_3$ in Formula 6. In some embodiments, n is 0, $R_1$ is —H; $R_{2a}$ is —$CH_3$ and $R_{2b}$ is —$CH_2D$ in Formula 6. In some embodiments, n is 0, $R_1$ is —H; $R_{2a}$ is —$CH_2D$ and $R_{2b}$ is —$CH_3$ in formula 6. In some embodiments, n is 0, $R_1$ is —H; and $R_{2a}$ and $R_{2b}$ are —$CH_2D$ in Formula 6. In some embodiments, n is 1, $R_1$ is -D; and $R_{2a}$ and $R_{2b}$ are —$CH_2D$ in Formula 6. In some embodiments, the ETBR antagonist is:

Compound (1)

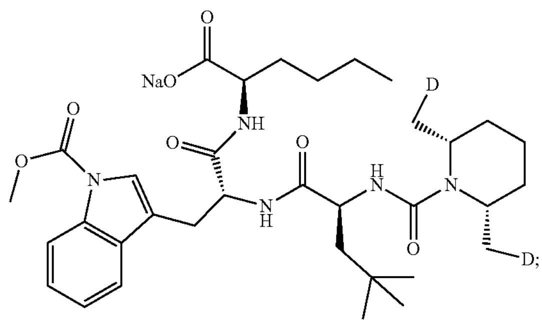

or a pharmaceutically acceptable salt thereof.

In some embodiments, the ETBR antagonist for use in a method described herein is formulated as a controlled, or delayed release formulation. In some embodiments, the ETBR antagonist is formulated as nanoparticles. In some embodiments, the ETBR antagonist is a non-deuterated BQ-788 analog. In some embodiments, the ETBR antagonist is a deuterated BQ-788 analog.

In some embodiments, the method further comprises administering to the subject an additional therapeutic agent. In some embodiments, the additional therapeutic agent is an anti-oncologic therapeutic agent or an anti-bacterial or an antimicrobial therapeutic agent. In some embodiments, the additional therapeutic agent is an anti-oncologic therapeutic agent. In some embodiments, the anti-oncologic agent is selected from a bRAF inhibitor, an immune checkpoint inhibitor, a caspase-8 inhibitor, an ETAR antagonist, niacinamide, a chemotherapeutic agent, or any combination thereof. In some embodiments, the anti-oncologic agent is an immune checkpoint inhibitor. In some embodiments, the immune checkpoint inhibitor is selected from at least one anti-PD1 antibody, at least one anti-PD-L1 antibody, at least one anti-CTLA4 antibody, or any combination thereof. In some embodiments, the at least one anti-PD1 antibody is selected from pidilizumab, BMS-936559, nivolumab, pembrolizumab, or any combination thereof. In some embodiments, the at least one anti-PD-L1 antibody is selected from atezolizumab, avelumab, durvalumab, MDX-1105, or any combination thereof.

In some embodiments, the ETBR antagonist is administered 2, 3, 4, or 5 times the frequency of the additional therapeutic agent. In some embodiments, the ETBR antagonist is administered 3 times every 2-3 weeks and the additional therapeutic agent is administered 1 time about every 2-3 weeks. In some embodiments, the ETBR antagonist is administered 3 times about every 21 days and the additional therapeutic agent is administered 1 time about every 21 days. In some embodiments, the ETBR antagonist is administered orally, intravenously, intravesically, intrathecally, intracavernously, intramuscularly, topically, via inhalation, rectally, intradermally, or any combination thereof.

In some embodiments, the tertiary lymphoid organ is formed within or adjacent to the urothelial or kidney cancer. In some embodiments, the tertiary lymphoid organ is formed within or adjacent to said kidney cancer. In some embodiments, the tertiary lymphoid organ is formed within or adjacent to the urothelial cancer. In some embodiments, the urothelial cancer is bladder cancer, ureter cancer, renal pelvic cancer, or any combination thereof. In some embodiments, the urothelial cancer is bladder cancer. In some embodiments, the bladder cancer is urothelial carcinoma, squamous cell carcinoma, adenocarcinoma, small cell carcinoma, sarcoma, or any combination thereof. In some embodiments, the subject is a human. In some embodiments, the subject is resistant to an immunotherapy before the treatment. In some embodiments, the administration restores Tumor Infiltrating Lymphocytes (TILs) to a microenvironment of said urothelial or kidney cancer.

In some embodiments, provided herein are methods for treating urothelial or kidney cancer in a subject in need thereof. In some embodiments, provided herein are methods for treating urothelial or kidney cancer in a subject in need thereof, comprising administering to said subject an endothelin B receptor (ETBR) antagonist, wherein said administering is effective to treat said urothelial or kidney cancer, and wherein said ETBR antagonist is Compound (1)

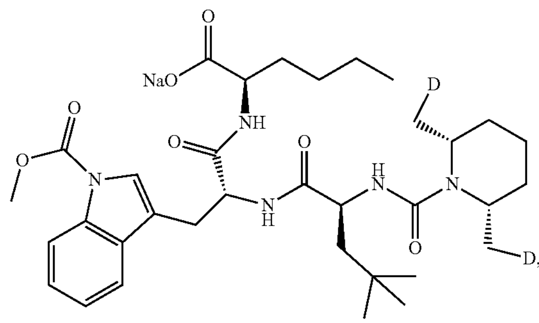

or a pharmaceutically acceptable salt thereof. In some embodiments, the ETBR antagonist is formulated as a controlled, or delayed release formulation. In some embodiments, the ETBR antagonist is formulated as nanoparticles. In some embodiments, the method further comprises administering to the subject an additional therapeutic agent. In some embodiments, the additional therapeutic agent is an anti-oncologic, an anti-bacterial, an anti-viral, or an antimicrobial agent. In some embodiments, the additional therapeutic agent is an anti-oncologic agent. In some embodiments, the anti-oncologic agent is selected from a bRAF inhibitor, an immune checkpoint inhibitor, a caspase-8 inhibitor, an endothelin A receptor (ETAR) antagonist, niacinamide, a chemotherapeutic agent, or any combination thereof. In some embodiments, the anti-oncologic agent is an immune checkpoint inhibitor. In some embodiments, the immune checkpoint inhibitor is an anti-PD1 antibody, anti-PD-L1 antibody, anti-CTLA4 antibody, or a variant or functional fragment thereof. In some embodiments, the anti-PD1 antibody is selected from pidilizumab, BMS-936559, nivolumab, pembrolizumab, or a variant or functional fragment thereof. In some embodiments, the anti-PD-L1 antibody is selected from atezolizumab, avelumab, durvalumab, MDX-1105, or a variant or functional fragment thereof. In some embodiments, greater reduction in volume of the urothelial or kidney cancer is observed in the subject upon administration of the immune checkpoint inhibitor and the ETBR antagonist as compared to the reduction in volume of the urothelial or kidney cancer upon individual administration of the ETBR antagonist, absent the immune checkpoint inhibitor or the immune checkpoint inhibitor absent the ETBR antagonist. In some embodiments, an at least 1-fold or 2-fold reduction in volume of the urothelial or kidney cancer is observed in the subject upon administration of the immune checkpoint inhibitor and the ETBR antagonist as compared to the reduction in volume of the urothelial or kidney cancer upon individual administration of the ETBR antagonist, absent the immune checkpoint inhibitor or the immune checkpoint inhibitor absent the ETBR antagonist. In some embodiments, extended survival of the subject is observed upon administration of the immune checkpoint inhibitor and the ETBR antagonist as compared to the survival of the subject upon individual administration of the ETBR antagonist, absent the immune checkpoint inhibitor or the immune checkpoint inhibitor absent the ETBR antagonist. In some embodiments, survival of the subject is extended by at least 1 month, 3 months, 6 months, or 1 year upon administration of the immune checkpoint inhibitor and the ETBR antagonist as compared to the extended survival upon individual administration of the ETBR antagonist, absent the immune checkpoint inhibitor or the immune checkpoint inhibitor absent the ETBR antagonist. In some embodiments, the ETBR antagonist and the additional therapeutic agent are administered sequentially or simultaneously. In some embodiments, the ETBR antagonist is administered at 2, 3, 4, or 5 times the frequency of the additional therapeutic agent. In some embodiments, the ETBR antagonist is administered 3 times about every 2-3 weeks and the additional therapeutic agent is administered 1 time about every 2-3 weeks. In some embodiments, the ETBR antagonist is administered 3 times about every 21 days and the additional therapeutic agent is administered 1 time about every 21 days. In some embodiments, the ETBR antagonist is administered is orally, intravenously, intravesically, intrathecally, intracavernously, intramuscularly, topically, via inhalation, rectally, intradermally, or any combination thereof. In some embodiments, the subject has at least one of: hematuria, pain during urination, a burning sensation during urination, frequent urination, urgency to urinate, inability to pass urine, unilateral back pain, or a combination thereof. In some embodiments, the subject has kidney cancer. In some embodiments, the subject has a urothelial cancer. In some embodiments, urothelial cancer is bladder cancer, ureter cancer, renal pelvic cancer, and any combination thereof. In some embodiments, the urothelial cancer is bladder cancer. In some embodiments, bladder cancer is urothelial carcinoma, squamous cell carcinoma, adenocarcinoma, small cell carcinoma, sarcoma, and any combination thereof. In some embodiments, the subject is resistant to immunotherapy.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 9A is an image of the control treated tumor cells. FIG. 9B is an image of the tumor cells treated with anti-PD1 and dabrafenib. FIG. 9C is an image of the tumor cells treated with anti-PD1 and BQ-788-B (ENB-003). FIG. 9D is an image of the tumor cells treated with anti-PD1 and BQ-788-B (ENB-003). FIG. 9E is a high magnification image of TLO formation. The combination of BQ-788-B (Compound 1) and an immune checkpoint inhibitor eradicated the tumors in 21 days, promoted robust infiltration by CD8+ lymphocytes (TILs), and induced tertiary lymphoid organ (TLO) formation.

FIG. 10 illustrates intratumoral TLO formation induced by the combination of the immune checkpoint inhibitor, an anti-PD1 antibody, and the specifically deuterated ETBR antagonist BQ-788-B (Compound 1). Histological examination of V600E+ melanoma tumor cells implanted into C57BL/6 mice 21 days after treatment as indicated in FIG. 8 with BQ-788-B (Compound 1) and anti-PD1 combination therapy. The staining of CD8+, CD4+ and Treg (FoxP3) lymphocytes indicates that the combination therapy promotes strong mobilization of lymphocytes to the tumor, which is associated with tumor eradication and positive patient outcomes.

FIG. 11 illustrates intratumoral (internal) TLO formation associated with treatment with the specifically deuterated compound BQ-788-B (Compound 1). The tables summarize results obtained with combination therapies (two- and three-part), TLO formation and efficacy for tumor eradication. The data indicate that (i) internal TLO formation is associated with tumor reduction; and (ii) the combination immune checkpoint inhibitors and BQ-788-B (COMPOUND 1) was most frequently associated with intratumoral TLO formation and tumor reduction.

FIG. 13 illustrates diffuse CD8+ TIL staining resulting from the combination of the specifically deuterated compound BQ-788-B (Compound 1) at 0.6 μg in with an immune checkpoint inhibitor (e.g., anti-CTLA antibody, anti-PD-L1 antibody, or anti-PD1 antibody) and dabrafenib. Histological examination of V600E+ melanoma tumor cells implanted into C57BL/6 mice 21 days after treatment as indicated in FIG. 8 with the respective combination therapy. The diffuse distribution of CD8+ TIL staining (dark punctate staining in "D+P+B (0.6 μg)") appears to be associated with higher efficacy as compared to those with peripheral distribution of TILs (see "D+P+B (4.0 μg)" and "D+P+B (100 μg)").

FIG. 20 illustrates intratumoral TLO formation following the combination of an ETBR antagonist (deuterated BQ-788) and an immune checkpoint inhibitor (an anti-PD1 antibody). The staining of CD8+, CD4+ and Treg (FoxP3) lymphocytes indicates that the combination therapy promotes strong mobilization of lymphocytes to the tumor, which is associated with tumor eradication and positive patient outcomes. Histological examination of V600E+ melanoma tumor cells implanted into C57BL/6 mice 21 days after treatment with the combination therapy.

DETAILED DESCRIPTION

Figure 1:
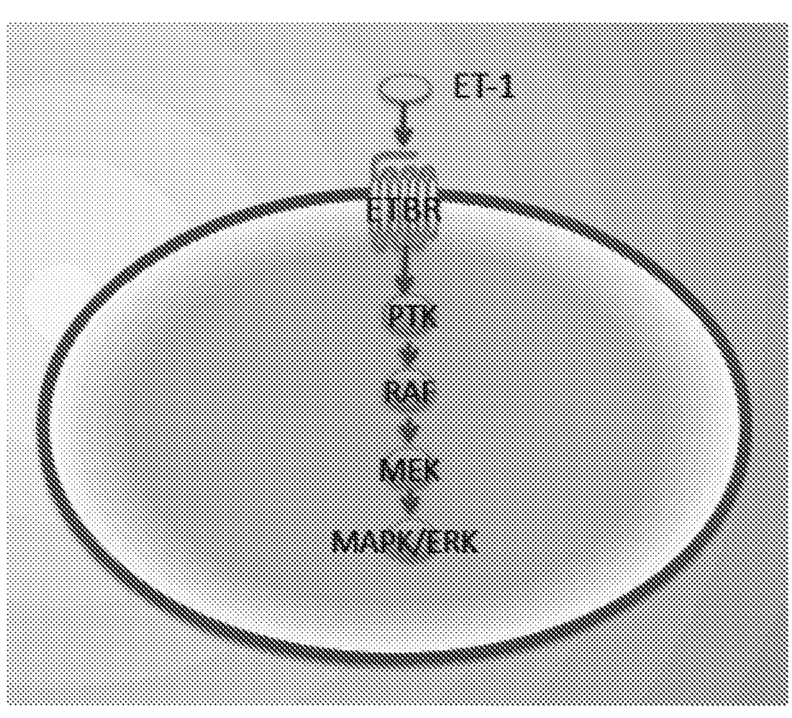
FIG. 1 illustrates an endothelin B receptor (ETBR) cell signal pathway. ETBR is a seven transmembrane G-protein coupled receptor (GPCR). Endothelin-1 (ET-1) is the ligand for the ETBR. Binding of ET-1 to the receptor results in the activation of a number of downstream kinases, including PTK, RAF, MEK, MAPK/ERK.

Disclosed herein, in certain embodiments, are ETBR antagonist compounds, and compositions useful for the treatment of an urothelial or kidney cancer. As described herein, ETBR antagonists are surprisingly advantageous for treating a urothelial or kidney cancer. Also surprisingly advantageous is a combination therapy of ETBR antagonists provided herein and additional therapeutic agents for the treatment of an urothelial or kidney cancer. In some embodiments, the ETBR antagonist compounds described herein are deuterated ETBR antagonists. In some embodiments, deuterated ETBR antagonists disclosed herein exhibit significantly improved biologic activity relative to a non-deuterated parent compound. In some embodiments, the use of the deuterated ETBR antagonists disclosed herein results in at least one of increased stability, prolonged serum bioavailability, prolonged ETBR target engagement, or any combination thereof, relative to a non-deuterated parent compound. In some embodiments, the subject treated is resistant to an immunotherapy. In some embodiments, the methods disclosed herein restore Tumor Infiltrating Lymphocytes (TILs) and/or induce intratumoral tertiary lymphoid organ (TLO) formation in a tumor microenvironment.

Provided herein are also methods of treatment of urothelial, bladder, or kidney cancers in an individual in need thereof, comprising administering an ETBR antagonist and an additional therapeutic agent. Formation of a TLO in a subject is beneficial for the treatment of an urothelial or a kidney cancer. In embodiments described herein, one or more of these conditions is treated in a subject by forming TLOs in the subject. In some embodiments, TLOs are formed by administering an ETBR antagonist. In some embodiments, TLOs are formed by administering an ETBR antagonist in combination with one or more additional therapeutic agents. In some embodiments, the methods disclosed herein effectuate at least one of (a) enhancement or stimulation of tumor infiltrating lymphocytes (TILs), (b) increased tumor associated macrophages (TAMs), (c.) enhancement or stimulation of tertiary lymphoid organ (TLO) formation or (d.) a combination thereof, thereby treating at least one symptom of the urothelial, bladder, or kidney cancer.

Also disclosed herein are methods of treating an urothelial or kidney cancer in a subject in need thereof, comprising administering to the subject a combination of least one ETBR antagonist, and at least one additional anti-oncologic therapeutic agent, administered either at the same time or at different times. In some embodiments, the ETBR antagonist is a deuterated ETBR antagonist. In some embodiments, the at least one anti-oncologic agent is selected from a bRAF inhibitor, an immune checkpoint inhibitor, a caspase-8 inhibitor, an ETAR antagonist, niacinamide, a chemotherapeutic agent such as, e.g., a taxane, a kinase inhibitor, or other receptor antagonist or combination thereof. In some embodiments, the at least one anti-oncologic agent is an immune checkpoint inhibitor. In some embodiments, the immune checkpoint inhibitor is an anti-PD1 antibody or an anti-PD-L1 antibody. In some embodiments, the anti-PD1 antibody is nivolumab, pembrolizumab, pidilizumab, cemiplimab, or any combination thereof. In some embodiments, the anti-PD-L1 antibody is atezolizumab, MDX-1105, avelumab, durvalumab, or any combination thereof. In some embodiments, the ETBR antagonist and the anti-oncologic agent (e.g., an immune checkpoint inhibitor such as anti-CTLA, anti-PDL1, or anti-PD1 antibody) are administered at the same time (e.g., simultaneously). In some embodiments, the specifically deuterated ETBR antagonist and the anti-oncologic agent (e.g., an immune checkpoint inhibitor such as an anti-CTLA, anti-PDL1, or anti-PD1 antibody) are administered at different times. In some embodiments, the specifically deuterated ETBR antagonist and the anti-oncologic agent (e.g., an immune checkpoint inhibitor such as an anti-CTLA antibody, an anti-PDL1 antibody, and an anti-PD1 antibody) are administered simultaneously. In some embodiments, the ETBR antagonist is administered once weekly, biweekly, monthly, or bimonthly. In some embodiments, the anti-oncologic agent (e.g., the immune checkpoint inhibitor such as an anti-CTLA, anti-PDL1, and anti-PD1 antibody) is administered once weekly, biweekly, monthly, or bimonthly. In some embodiments, the ETBR antagonist is administered 2, 3, 4, or 5 times frequently as the additional anti-oncologic agent. In some embodiments, the deuterated ETBR antagonist is administered 3 times during 2-3 weeks (e.g., 21 days) while the additional anti-oncologic agent is administered 1 time during the 2-3 weeks (e.g., the 21 days). In some embodiments, the combination comprises an effective amount of the at least one deuterated ETBR antagonist and an effective amount of the at least one anti-oncologic agent. In some embodiments, the combination includes a pharmaceutically acceptable carrier, for example DMSO. In some embodiments, the ETBR antagonist is in separate unit dosage form from the anti-oncologic agent, for example, a first container that comprises the at least one specifically deuterated ETBR antagonist, and a second container that comprises the at least one anti-oncologic agent. In some embodiments, the ETBR antagonists and anti-oncologic therapeutic agents disclosed herein are in a controlled-release delivery system. In some embodiments, the controlled release delivery system comprises at least one of: (1) a biocompatible polymer, (2) a liposome preparation; (3) a DMSO solution, or a combination thereof.

DEFINITIONS

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges is also encompassed within the invention, subject to any specifically excluded limit in the stated range. Where the stated range includes one or both of the limits, ranges excluding either both of those included limits are also included in the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "combination therapy" refers to both concurrent administration (administration of two or more therapeutic agents at the same time) and time varied administration (administration of one or more therapeutic agents at a time different from that of the administration of an additional therapeutic agent or agents). In some embodiments, the therapeutic agents are present in the patient to some extent, for example at effective amounts, at the same time. In some embodiments, one or more of the compounds described herein, are administered in combination with at least one additional bioactive agent, especially including an anticancer agent. In some embodiments, the combination therapy of compounds results in synergistic activity, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure, are set forth hereinabove.

The term "anti-oncologic agent" is used to describe an anti-cancer agent. These agents include, for example, everolimus, niacinamide, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bc1-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts. In some embodiments, sodium and potassium salts are suitable neutralization salts of the phosphates.

The term "effective" is used to describe an amount of a compound, composition or component which, when used within the context of its intended use, effects an intended result. The term "effective" subsumes all other effective amount or effective concentration terms, which are otherwise described or used in the present application.

The term "therapeutically effective amount" refers to that amount which is sufficient to effect treatment, as defined herein, when administered to a mammal in need of such treatment.

The term "patient" or "subject" is used throughout the specification to describe an animal, for example a human, or a domesticated animal, to whom treatment, including prophylactic treatment, with the compositions according to the present disclosure is provided. For treatment of those conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term. Activation of the ETBR by endothelins such as ET-1 and ET-3, results in a variety of molecular events that promote melanoma invasion and metastasis. Without being bound by any particular theory, it is hypothesized that while the majority of melanomas express ETBR, a subset of these also expresses the ETBR activator ET-1 and/or ET-3. It is this subset that is therefore most likely dependent upon ETBR activation for viability, invasive potential and metastatic potential. Thus, this subset of patients is most likely to respond to ETBR blockade. Furthermore, this subset of patients is least likely to response to immune based therapy.

Endothelin Family Antagonists

The Endothelin B receptor (ETBR) pathway (FIG. 1) plays a significant role in the metastatic spread of melanoma, and therefore, is a target for therapeutic intervention. The Endothelin B receptor is a 7 transmembrane G-protein coupled receptor (GPCR). It is expressed at very low levels in normal melanocytes, but is upregulated during melanoma development and progression. RAF and MEK kinases, current melanoma drug targets, are activated by the deuterated ETBR. The specific deuterated ETBR compounds are beneficial because, as compared to nondeuterated ETBR compounds, there is an improvement in one or more pharmaceutical properties (e.g. efficacy, solubility)

Figure 2:
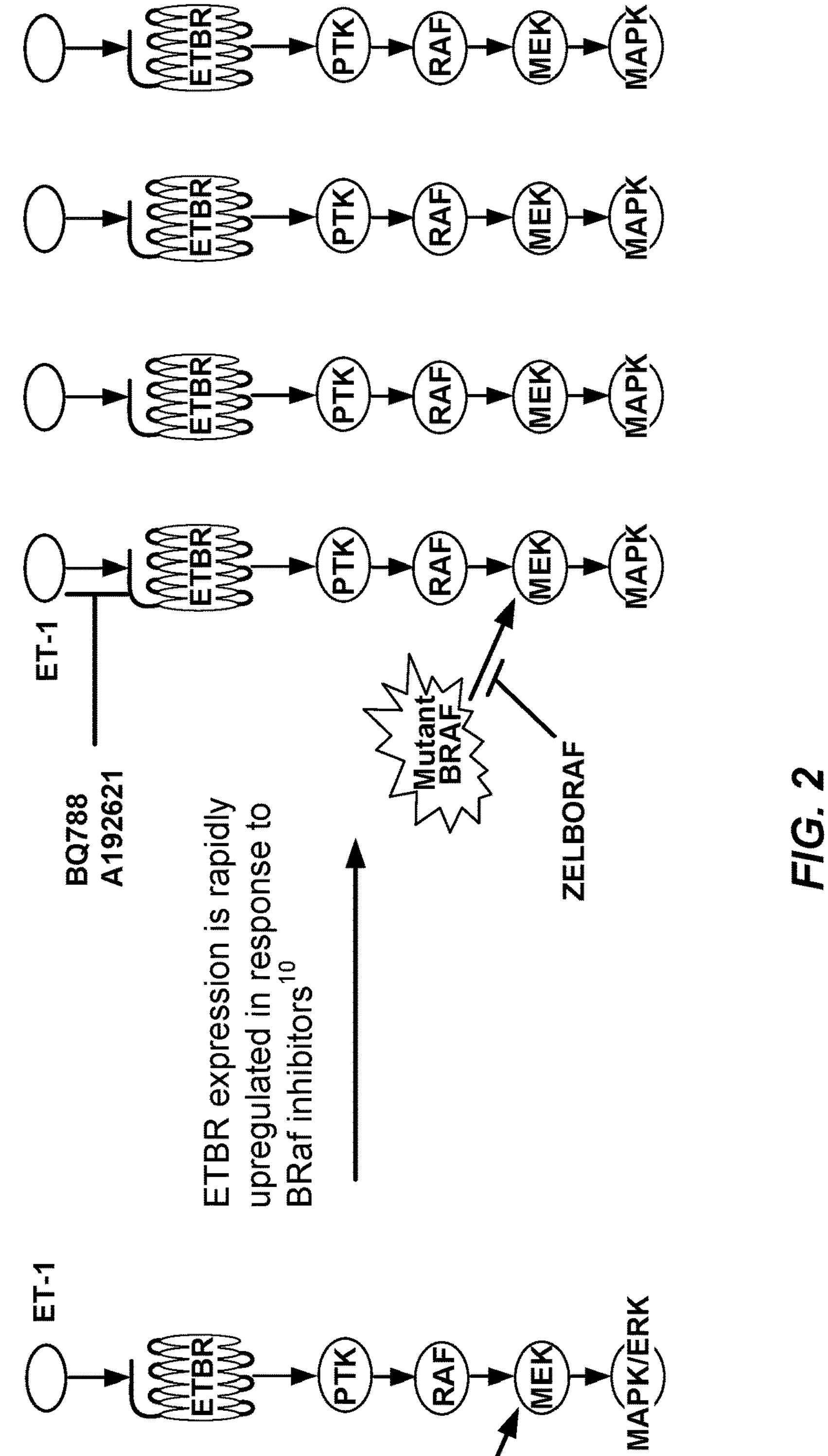
FIG. 2 illustrates drug resistance to bRAF inhibitors due to ETBR upregulation. Upregulation of ETBR allows melanoma cells to bypass the block to MAPK/ERK activation. ETBR antagonists, including specifically deuterated ETBR antagonists as described herein, block ET-1 binding.
Figure 3:
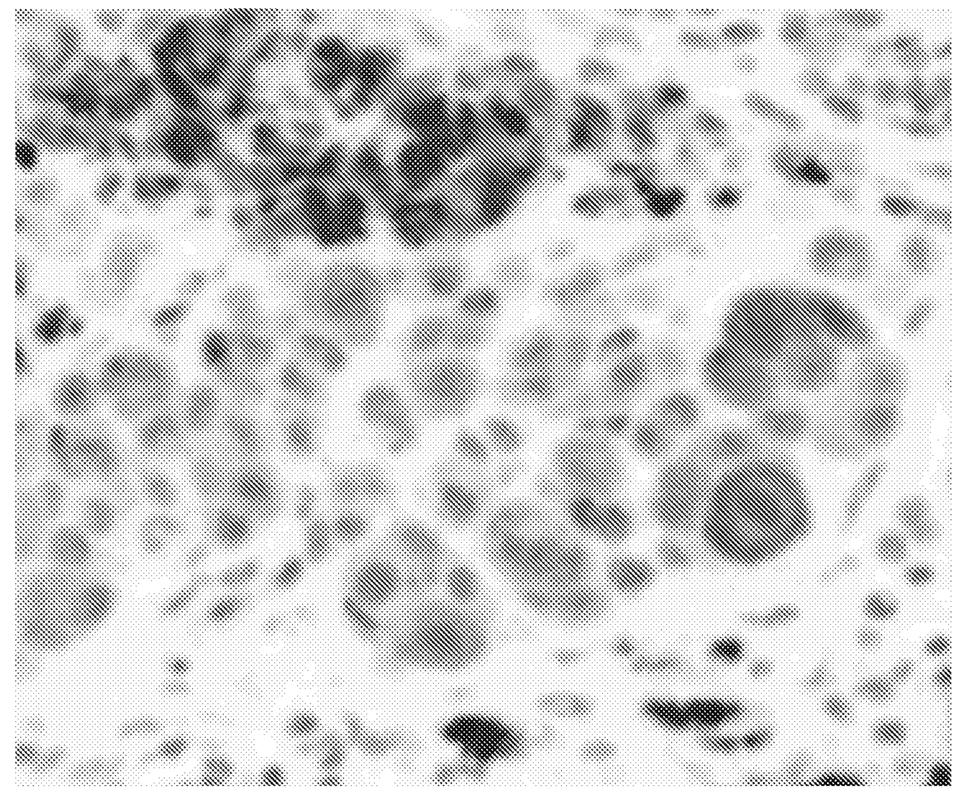
FIG. 3 illustrates ET-1 expression by advanced melanomas. ET-1 is the ligand that activates the ETBR, which results in the proliferation, metastasis, and angiogenesis of melanoma cells. The tissue section is from a human invasive melanoma specimen stained with an ET-1 specific label. The photograph indicates that the melanoma is positive for ET-1. Invasive and metastatic melanomas produce ET-1.

Endothelin-1 (ET-1) (and Endothelin-3, not shown) is a ligand that activates the ETBR (FIG. 2). ET-1 activation of ETBR causes melanoma cells to proliferate, metastasize and generate their own blood supply. As shown in FIG. 3, pigmented invasive melanomas and metastatic melanomas are observed to produce ET-1 (FIG. 3).

Provided herein, in certain embodiments, are methods of treating a urothelial cancer, bladder cancer, ureter cancer, renal pelvic cancer, or any combination thereof in an individual in need thereof, comprising administering to the individual an antagonist to a member of an endothelin family. The endothelin family can comprise peptides, ET-1, ET-2, and ET-3. Endothelin family antagonists include, for example, Formula 1, Formula 2, Formula 3, Formula 4, Formula 5, Formula 6, Compound 1, BQ-788, BQ-788-A, BQ-788-B, and/or BQ-788-C. In some embodiments, an endothelin family antagonist, such as Formula 1, Formula 2, Formula 3, Formula 4, Formula 5, Formula 6, Compound 1, BQ-788, BQ-788-A, BQ-788-B, and/or BQ-788-C is utilized for the treatment of urothelial carcinoma, squamous cell carcinoma, adenocarcinoma, small cell carcinoma, sarcoma, and any combination thereof.

Endothelin-1 (ET-1) is a 21 amino acid peptide that is produced by the vascular endothelium. It is a potent vasoconstrictor that binds to smooth muscle endothelin receptors, of which there are two subtypes: ETA and ETB receptors. These receptors are coupled to a G-protein, and receptor activation leads to the formation of IP3, which causes the release of calcium by the sarcoplasmic reticulum and increased smooth muscle contraction and vasoconstriction. There are also ETB receptors located on the endothelium that stimulate the formation of nitric oxide, which produces vasodilation in the absence of smooth muscle ETA and ETB receptor activation. This receptor distribution helps to explain the phenomenon that ET-1 administration causes transient vasodilation (initial endothelial ETB activation) and hypotension, followed by prolonged vasoconstriction (smooth muscle ETA and ETB activation) and hypertension. ETA is more abundant in a smooth muscle layer as compared to ETB.

ET-1 and ET-2 bind to a G-protein coupled receptor, ETAR and ETBR. Endothelin members can be expressed on various organs such as the brain, kidney, lung, liver, and heart. In some embodiments, the endothelin member that is antagonized is in a brain, pial artery, intra-cerebral, kidney, renal vein, renal artery, arcuate artery, resistance vessel, lung, pulmonary artery, liver, portal vein, heart, aorta, coronary artery, or any combination thereof.

In some embodiments, the endothelin family antagonist is cyclic pentapeptide BQ-123 (D-Asp-L-Pro-D-Val-L-Leu-D-Trp-). BQ-123 is derived from peptides isolated from *Streptomyces misakiensis*, a highly selective competitive ETA antagonist with low nanomolar affinity for the receptor. In some embodiments, the endothelin family antagonist is FR 139317 (N-[(hexahydro-1-azepinyl) carbonyl]L-Leu[1-Me] D-Trp-3 [2-pyridyl]-D-Ala), a linear tripeptide. In some embodiments, BQ-123 and FR 139317 are ETA selective (e.g., have higher affinity for ETA than for other endothelin receptors) in certain mammalian (such as human and/or rodent) ET receptors. In some embodiments, BQ-123 and FR 139317 can also be used to antagonize a receptor other than ETA. In some embodiments, the endothelin family antagonist is TAK-044.

In some embodiments, the endothelin family antagonist is a dual endothelin A and endothelin B receptor antagonist. In some embodiments, the dual antagonist is any one of: bosentan, macitentan, tezosentan, which affect both endothelin A and B receptors.

In some embodiments, the endothelin family antagonist is a selective ETA receptor antagonist. In some embodiments, the ETA receptor antagonist is any one of: sitaxentan, ambrisentan, atrasentan, BQ-123, zibotentan, which affect endothelin A receptors. In some embodiments, the endothelin family antagonist is ambrisentan, which is a selective ETA receptor antagonist.

In some embodiments, the endothelin family antagonist is a selective ETB receptor antagonist. In some embodiments, the selective ETB receptor antagonist is any one of: BQ-788 and/or A192621. In some embodiments, BQ788 (N-[([2R, 6S]-2,6-dimethyl-1-piperidinyl) carbonyl]-4-methyl-L-leucyl-N-[(1R)-1-carboxylatopentyl]-1-[methoxycarbonyl]-D-tryptophanamide) and any derivatives thereof are utilized as an endothelin family antagonist. BQ788 is a modified tripeptide developed by structure-activity analysis and is a selective competitive ETB antagonist.

In some embodiments, when an endothelin family antagonist is administered as a peptide, it is administered intraarterially. As such, it may be metabolized or excreted over comparatively short periods of time as compared to a comparable antagonist absent the intraarterial introduction. In some embodiments, the peptide may be soluble and may not bind plasma proteins.

Deuterated Compounds (Specific)

In some embodiments, the ETBR antagonist is a specifically deuterated ETBR antagonists. In some embodiments, the specifically deuterated ETBR antagonist is a deuterated form of BQ-788 as described herein. In some embodiments, the ETBR antagonist is administered in a composition further comprising a pharmaceutically acceptable carrier. In some embodiments, the ETBR antagonist is administered in a composition, comprising an effective amount of at least one specifically deuterated ETBR antagonist, e.g., a deuterated form of BQ-788 as described herein, and a pharmaceutically acceptable carrier. In some embodiments, the pharmaceutical composition as described herein is in unit dosage form configured for administration one or more times, for example, one or more times per day, per week, or per month.

In some embodiments, the specifically deuterated ETBR antagonist is a compound of the Formula (1) below:

Formula (1)

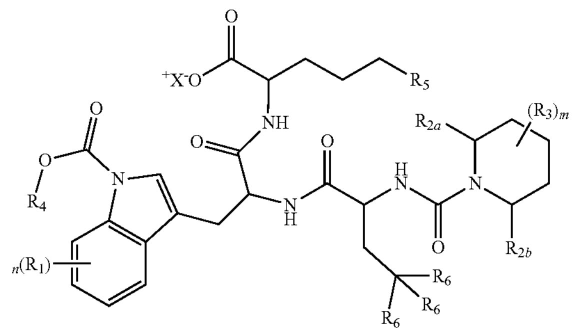

wherein n is an integer from 0-5;

m is an integer from 0-3;

X is a positively charged counterion;

$R_1$ and $R_3$ are independently —H, -D, —$CH_3$, —$CH_2D$, —$CHD_2$, or —$CD_3$;

$R_{2a}$, $R_{2b}$, $R_4$, $R_5$, and $R_6$ are independently —$CH_3$, —$CH_2D$, —$CHD_2$, or —$CD_3$; and at least one of $R_1$, $R_2$, or $R_3$ comprises deuterium.

In some embodiments, the specifically deuterated ETBR antagonist of formula (1) comprises 1-8 deuterium atoms. In specific embodiments, the specifically deuterated ETBR antagonist of formula (1) comprises 1, 2, or 3 deuterium atoms.

In some embodiments, the specifically deuterated ETBR antagonist of Formula I is a compound of the Formula (2) below:

Formula (2)

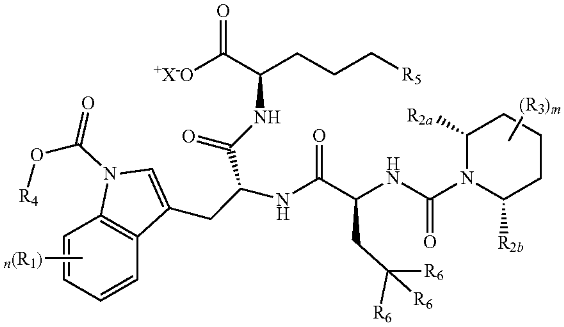

In some embodiments, the specifically deuterated ETBR antagonist of Formula I is a compound of the Formula (3) below:

Formula (3)

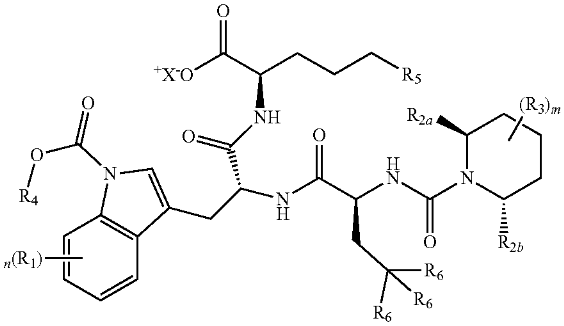

In some embodiments, the specifically deuterated ETBR antagonist of Formula I is a compound of the Formula (4) below:

Formula (4)

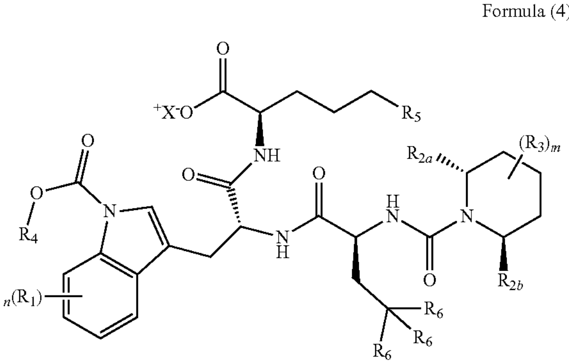

In some embodiments, the specifically deuterated ETBR antagonist of Formula I is a compound of the Formula (5) below:

Formula (5)

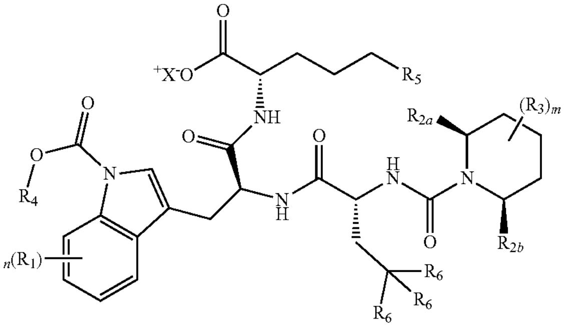

In some embodiments, the specifically deuterated ETBR antagonist of Formula I is a compound of the formula (6) below:

Formula (6)

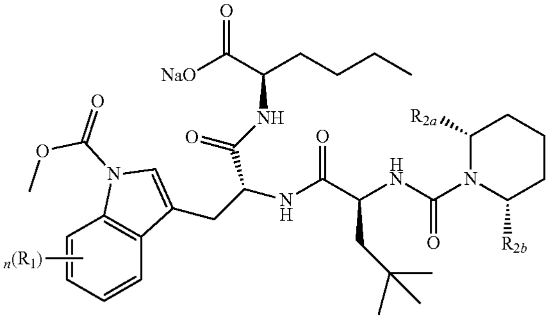

In some embodiments, the specifically deuterated ETBR antagonist of formula (6), n is 0 or 1.

In some embodiments of the specifically deuterated ETBR antagonist of formula (6), n is 1 and $R_1$ is -D.

In some embodiments of the specifically deuterated ETBR antagonist of formula (6), n is 1, $R_1$ is -D; and $R_{2a}$ and $R_{2b}$ are —$CH_3$.

In some embodiments of the specifically deuterated ETBR antagonist of formula (6), n is 0, $R_1$ is —H; $R_{2a}$ is —$CH_3$ and $R_{2b}$ is —$CH_2D$.

In some embodiments of the specifically deuterated ETBR antagonist of formula (6), n is 0, $R_1$ is —H; $R_{2a}$ is —$CH_2D$ and $R_{2b}$ is —$CH_3$.

In some embodiments of the specifically deuterated ETBR antagonist of formula (6), n is 0, $R_1$ is —H; and $R_{2a}$ and $R_{2b}$ are —$CH_2D$.

In some embodiments of the specifically deuterated ETBR antagonist of formula (6), n is 1, $R_1$ is -D; and $R_{2a}$ and $R_{2b}$ are —$CH_2D$.

In some embodiments, the specifically deuterated ETBR antagonist is at least one of BQ-788-A, BQ-788-B (Compound 1), BQ-788-C, or a combination thereof, including analogs, derivatives, polymorphs, prodrugs, and salts thereof, including fluorinated analogues. For example, the specifically deuterated ETBR antagonist can be a fluorinated analog of BQ-788-A, BQ-788-B (Compound 1), or BQ-788-C.

BQ-788-A is a specifically deuterated ETBR antagonist depicted below:

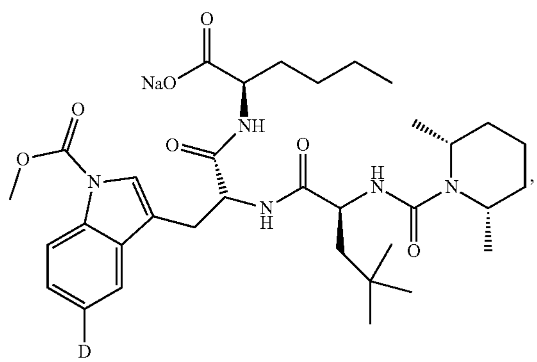

a stereoisomer thereof, or a pharmaceutically acceptable salt thereof.

BQ-788-B (Compound 1) is a specifically deuterated ETBR antagonist depicted below:

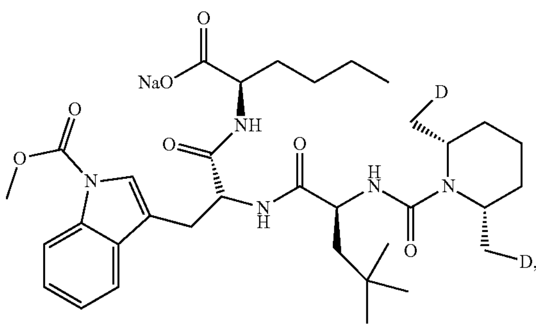

a stereoisomer thereof, or a pharmaceutically acceptable salt thereof.

BQ-788-C is a specifically deuterated ETBR antagonist depicted below:

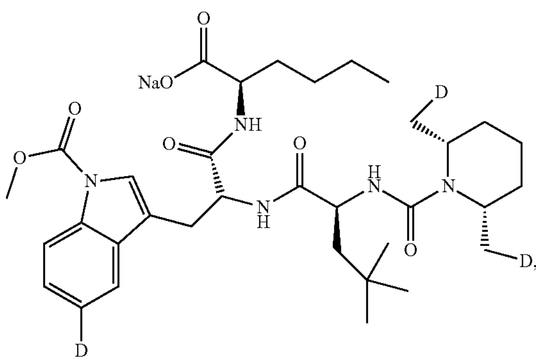

a stereoisomer thereof, or a pharmaceutically acceptable salt thereof.

In some embodiments, the ETBR antagonist is a compound is of Formula (7):

Formula (7)

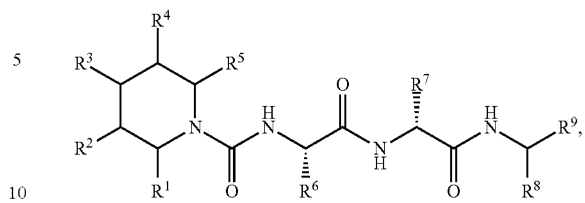

a stereoisomer thereof, or a pharmaceutically acceptable salt thereof, wherein:

each of $R^1$, $R^2$, $R^3$, $R^4$, or $R^5$ is independently hydrogen, halogen, hydroxyl, deuterium, halogen, hydroxy, amino, nitro, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ haloalkykl, optionally substituted aryl, or optionally substituted heteroaryl, optionally wherein one or more of the carbons in the piperidinyl ring can be a heteroatom selected from O, N, or S, or wherein the piperidinyl ring may contain one or more double bonds;

$R^6$ is optionally substituted $C_1$-$C_8$ alkyl, optionally substituted $C_2$-$C_8$ alkenyl, optionally substituted $C_2$-$C_8$ alkynyl, optionally substituted $C_3$-$C_8$-cycloalkyl, optionally substituted $C_1$-$C_8$ alkoxy, optionally substituted $C_1$-$C_8$ haloalkykl, optionally substituted aryl, or optionally substituted heteroaryl, wherein $R^6$ optionally comprises deuterium;

$R^7$ is optionally substituted cycloalkyl, optionally substituted heterocycloalkyl, optionally substituted aryl, optionally substituted heteroaryl, optionally substituted polycyclic ring system, optionally substituted bicyclic, optionally substituted heterobicyclic, wherein $R^7$ optionally comprises deuterium;

$R^8$ and $R^9$ are independently optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ haloalkyl, optionally substituted aryl, optionally substituted heteroaryl, or —COOR', or $R^8$ and $R^9$ may be taken together to form a optionally substituted cycloalkyl, optionally substituted cycloalkyl heterocycloalkyl, optionally substituted aryl, optionally substituted heteroaryl, or optionally substituted polycyclic ring system, wherein $R^8$ or $R^9$ each optionally comprises deuterium;

R' is hydrogen, hydroxy, or $C_1$-$C_8$ alkyl; and wherein at least one of $R^1$, $R^2$, $R^3$, $R^4$, $R^5$, $R^6$, $R^7$, $R^8$, or $R^9$ is deuterium.

In some embodiments, the ETBR antagonist is a compound of Formula (8):

Formula (8)

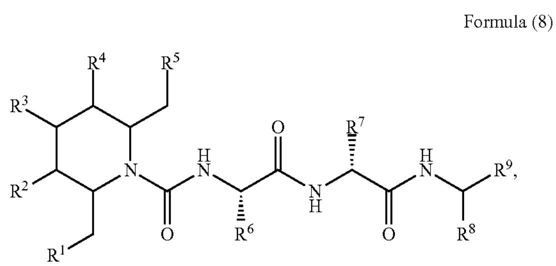

a stereoisomer thereof, or a pharmaceutically acceptable salt thereof, wherein:

each of $R^2$, $R^3$, or $R^4$ is independently hydrogen, deuterium, halogen, hydroxy, amino, nitro, $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ haloalkykl, aryl, or heteroaryl;

$R^6$ is $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ haloalkykl, aryl, or heteroaryl, wherein $R^6$ optionally comprises deuterium;

$R^7$ is substituted or unsubstituted cycloalkyl, substituted or unsubstituted heterocycloalkyl, substituted or unsubstituted aryl, substituted or unsubstituted heteroaryl, or a substituted or unsubstituted polycyclic ring system, wherein $R^7$ optionally comprises deuterium;

$R^8$ and $R^9$ are independently $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, heteroaryl, or —COOR', or $R^8$ and $R^9$ may be taken together to form a substituted or unsubstituted cycloalkyl, substituted or unsubstituted cycloalkyl heterocycloalkyl, substituted or unsubstituted aryl, substituted or unsubstituted heteroaryl, or substituted or unsubstituted polycyclic ring system, wherein $R^8$ or $R^9$ each optionally comprises deuterium;

R' is hydrogen, hydroxy, or $C_1$-$C_8$ alkyl; and wherein at least one of $R^1$, $R^2$, $R^3$, $R^4$, $R^5$, $R^6$, $R^7$, $R^8$, or $R^9$ is deuterium.

In some embodiments, the ETBR antagonist is a compound of Formula (9):

Formula (9)

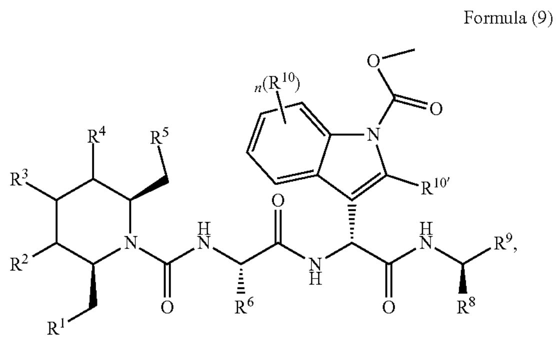

a stereoisomer thereof, or a pharmaceutically acceptable salt thereof, wherein:

each of $R^1$ $R^2$, $R^3$, $R^4$, or $R^5$ is independently hydrogen, deuterium, halogen, hydroxy, amino, nitro, $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ haloalkyl, aryl, or heteroaryl;

$R^6$ is $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, or heteroaryl, wherein $R^6$ optionally comprises deuterium;

$R^8$ and $R^9$ are independently $C_1$-$C_8$ alkyl, $C_2$-$C_8$ alkenyl, $C_2$-$C_8$ alkynyl, $C_3$-$C_8$ cycloalkyl, $R^8$ and $R^9$ are independently $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, heteroaryl, or —COOR', or $R^8$ and R' may be taken together to form a substituted or unsubstituted cycloalkyl, substituted or unsubstituted cycloalkyl heterocycloalkyl, substituted or unsubstituted aryl, substituted or unsubstituted heteroaryl, or substituted or unsubstituted polycyclic ring system, wherein $R^8$ or $R^9$ each optionally comprises deuterium;

$R^{10}$ and $R^{10'}$ are independently hydrogen, deuterium, halogen, hydroxy, amino, nitro, $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, or heteroaryl;

n is an integer from 0-4; and wherein at least one of $R^1$, $R^2$, $R^3$, $R^4$, $R^5$, $R^6$, $R^7$, $R^8$, $R^9$, $R^{10}$ or $R^{10'}$ is deuterium.

Pharmaceutical Compositions

Provided herein are methods of treating a urothelial or a kidney cancer, comprising administering a pharmaceutical composition comprising at least one ETBR antagonist, e.g., BQ-788 or a deuterated form of BQ-788 as described herein, and a pharmaceutically acceptable carrier.

In some embodiments, a pharmaceutical composition disclosed herein is formulated in a unit dosage form, including any desired carrier or excipient, and configured for administration via any desired route, e.g., oral, intravenous, subcutaneous, intramuscular, intraperitoneal, parenteral, intranasal, intracranial.

In some embodiments, a pharmaceutical composition disclosed herein is useful for the treatment of ETBR-related cancer in a patient. In some embodiments, the cancer is a solid tumor. In some embodiments, the cancer is at least one of bladder cancer, urothelial cancer, kidney cancer, breast cancer, melanoma, SCC, glioblastoma, ovarian cancer, pancreatic cancer, or a combination thereof. In some embodiments, a pharmaceutical composition disclosed herein is utilized to treat a bladder cancer such as urothelial carcinoma, squamous cell carcinoma, adenocarcinoma, small cell carcinoma, sarcoma, and any combination thereof.

In some embodiments, a pharmaceutical composition disclosed herein is administered in combination with an additional therapeutic agent. In some embodiments, the pharmaceutical composition is administered in combination with an anti-cancer agent. In some embodiments, the anti-cancer agent is an immune checkpoint inhibitor.

In some embodiments, a pharmaceutical composition disclosed herein is formulated in a conventional manner using one or more pharmaceutically acceptable carriers. In some embodiments, a composition as described herein is administered in a controlled-release formulation.

In some embodiments, a pharmaceutical composition disclosed herein comprises a pharmaceutically acceptable carrier. In some embodiments, the pharmaceutically acceptable carrier includes, but is not limited to, dimethyl sulfoxide (DMSO), soybean oil as a carrier, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat, or a combination thereof.

In some embodiments, a pharmaceutical composition disclosed herein comprises at least one of soybean oil, dimethyl sulfoxide (DMSO), hydrogel, or a combination thereof. Any of the embodiments described herein can be a single-component oil phase formulation, as described above, wherein each active ingredient can be at any of the dosages or concentrations described herein. The single-component oil phase can be a fixed oil, such as soybean oil. For example, the formulation comprises about 0.1 mg to about 5.0 mg of each active ingredient in 1 mL of the single-component oil (i.e., about 0.5 mg/mL, about 1 mg/mL, or about 1.5 mg/ml of each active ingredient in the single-component oil). The single-component oil phase formulation can be prepared by adding each active ingredient (e.g., about 1 mg to about 50 mg of each of the active ingredient (s)) to about 10 mL of the single-component oil solution.

In some embodiments, a pharmaceutical composition disclosed herein comprises a DMSO, e.g., in a DMSO solution that is about 5% to about 100% DMSO (e.g., about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 30% to about 95%, about 45% to about 95%, about 75% to about 95%, about 30% to about 90%, about 45% to about 90%, about 75% to about 90%, about 30% to about 85%, about 45% to about 85%, or about 75% to about 85%). For example, a pharmaceutical composition disclosed herein comprises about 0.1 mg to about 5.0 mg of each active ingredient in 1 mL of DMSO (i.e., about 0.5 mg/mL, about 1 mg/mL, or about 1.5 mg/mL of each active ingredient in DMSO). The DMSO pharmaceutical compositions can be prepared by adding each active ingredient (e.g., about 1 mg to about 50 mg of each of the active ingredient(s)) to about 10 mL of the DMSO solution. For example, the DMSO is a DMSO solution comprising about 5% to about 100% DMSO, about 25% to about 100% DMSO, about 50% to about 100% DMSO, about 75% to about 100% DMSO, about 5% to about 75% DMSO, about 25% to about 75% DMSO, about 50% to about 75% DMSO, about 5% to about 50% DMSO, about 25% to about 50% DMSO, or about 5% to about 25% DMSO.

In some embodiments, the ETBR antagonist (e.g., BQ-788, BQ-017, A192621, a deuterated or fluorinated analog thereof, or combinations thereof) or the ETAR antagonist (e.g., BQ123) is administered as a controlled release subcutaneous or intramuscular dosage formulation comprising a uniform dispersion of an in a biocompatible delivery system whereby following administration the deuterated ETBR and ETAR antagonists are released slowly and simultaneously from the formulation into the systemic circulation.

In some embodiments, a pharmaceutical composition disclosed herein is formulated into a controlled release delivery system comprising at least one biocompatible polymer. In some embodiments, the active compounds are prepared with carriers that will protect the compound against rapid elimination from the body, such as a controlled release formulation, including implants, hydrogels, thermo-sensitive hydrogels, and microencapsulated delivery systems. Biodegradable, biocompatible polymers can be used, such as ethylene vinyl acetate, acrylates, polycarboxylic acids, polyanhydrides, polyglycolic acid, collagen, polyorthoesters, and polylactic acid. In some embodiments, the biocompatible polymer is at least one of a poly(lactide), poly(glycolide), poly(lactide-co-glycolide), poly(lactic acid), poly (glycolic acid), poly(lactic acid-co-glycolic acid), polycaprolactone, polycarbonate, polyesteramide, polyanhydride, poly(amino acid), polyorthoester, polycyanoacrylate, poly(p-dioxanone), poly(alkylene oxalate), biodegradable polyurethane, blend, or a copolymer thereof.

In some embodiments, a pharmaceutical composition disclosed herein comprises a pharmaceutically acceptable carrier. In some embodiments, the pharmaceutically acceptable carrier comprises or is a liposome. For example, the pharmaceutical composition or formulation may comprise a liposome having an interior volume comprising an ETBR antagonist. In some embodiments, the liposome is configured to effectuate the controlled release of the ETBR antagonist, e.g., rapid release, extended release, or a combination thereof.

In some embodiments, the liposome is configured to effectuate the controlled release of the pharmaceutical compositions. In some embodiments, the liposome is configured to effectuate rapid release of the pharmaceutical compositions. In other embodiments, the liposome is configured or formulated to effectuate extended release the pharmaceutical compositions. In some embodiments, the liposome is configured to result in both the rapid and extended release of pharmaceutical compositions.

In some embodiments, the liposome is configured to effectuate the controlled release of the ETBR antagonist or the caspase-8 inhibitor or a combination thereof. In some embodiments, the liposome is configured to effectuate rapid release of the ETBR antagonist or the caspase-8 inhibitor or a combination thereof. In other embodiments, the liposome is configured or formulated to effectuate extended release the ETBR antagonist or the caspase-8 inhibitor or a combination thereof. In some embodiments, the liposome is configured to result in both the rapid and extended release of the ETBR antagonist or the caspase-8 inhibitor or a combination thereof.

In some embodiments, the pharmaceutically acceptable carrier is a liposomal suspension. In some embodiments, the liposome suspension is prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

In some embodiments, a pharmaceutical composition disclosed herein comprises a liposome having an interior volume comprising an ETBR antagonist or a caspase-8 inhibitor or a combination thereof, and an effective amount of at least one of an ETAR antagonist, an anti-PD1 antibody, a bRAF inhibitor, niacinamide or a combination thereof. In some embodiments, the liposome comprises at least one of a neutral lipid, a basic (having a net positive charge) lipid, an acidic (having a net negative charge) lipid, cholesterol, or a combination thereof. In some embodiments, the liposome further comprises a polymeric component. In some embodiments, the interior volume of the liposome is at least partially aqueous and comprises a specifically deuterated ETBR antagonist.

In some embodiments, a pharmaceutical composition disclosed herein comprises a liposomal delivery system, e.g., at least one of a phosphatidylethanolamine (PE) such as dipalmitoyl PE (DPPE), and partially unsaturated phosphatidylcholine (PC), such as egg PC (EPC) or SPC, fully unsaturated PC such as HSPC, PG, phosphatidylserine (PS), phosphatidylinositol (PI) or a combination thereof. In some embodiments, the phospholipid is at least one of a partially unsaturated PG, dipalmitoylphosphatidylglycerol (DPPG), cholesterol, DSPE-PEG2000, polysorbate-80 or combination thereof. In some embodiments, the liposomal delivery system is a controlled release system, e.g., at least one of rapid release, extended release, rapid and extended release, delayed release, sustained release, slow release, and combinations thereof.

In some embodiments, a pharmaceutical composition disclosed herein comprises a pharmaceutically acceptable salt. In some embodiments, the pharmaceutically acceptable salt is an acid or base addition salt of a compound described herein. In some embodiments, the acids used to prepare the pharmaceutically acceptable acid addition salts of the aforementioned base compounds are those which form non-toxic acid addition salts, i.e., salts containing pharmacologically acceptable anions, such as the hydrochloride, hydrobromide, hydroiodide, nitrate, sulfate, bisulfate, bitartrate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others. In some embodiments, pharmaceutically acceptable base addition salts may are used to produce pharmaceutically acceptable salt forms of the compounds or derivatives according to the present disclosure. In some embodiments, the chemical bases used as reagents to prepare pharmaceutically acceptable base salts of the present compounds that are acidic in nature are those that form nontoxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

In some embodiments, a pharmaceutical composition disclosed herein is formulated as an oral composition. In some embodiments, oral compositions include an inert diluent or an edible carrier. In some embodiments, they are enclosed in gelatin capsules or compressed into tablets. In some embodiments, for the purpose of oral therapeutic administration, the active compound or its prodrug derivative is incorporated with excipients and used in the form of tablets, troches, or capsules. In some embodiments, pharmaceutically compatible binding agents, and/or adjuvant materials are included as part of the composition. In some embodiments, the tablets, pills, capsules, troches and the like contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In some embodiments, the dosage unit form is a capsule. In some embodiments, the dosage unit formulated as a capsule comprises a liquid carrier such as a fatty oil. In some embodiments, the dosage unit formulated as a capsule comprises various other materials which modify the physical form of the dosage unit, for example, coatings of sugar, shellac, or enteric agents.

In some embodiments, a pharmaceutical composition disclosed herein comprises an elixir, suspension, syrup, wafer, chewing gum or the like. In some embodiments, the syrup comprises, in addition to the active compounds, sucrose as a sweetening agent and certain preservatives, dyes and colorings and flavors.

In some embodiments, a pharmaceutical composition disclosed herein comprises a solution or suspension used for parenteral, intradermal, subcutaneous, intravenous, intramuscular, or topical application. In some embodiments, the solution or suspension used for parenteral, intradermal, subcutaneous, intravenous, intramuscular, or topical application comprises the following components: a sterile diluent such as water for injection, saline solution, fixed oils (e.g., soybean oil), polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. In some embodiments, carriers for intravenous administration are physiological saline or phosphate buffered saline (PBS).

Combination Therapy

Disclosed herein, in certain embodiments, are methods of treating an urothelial cancer, bladder cancer, ureter cancer, renal pelvic cancer, kidney cancer or any combination thereof in an individual in need thereof, comprising administering to the individual a combination comprising an ETBR antagonist as described herein. Also disclosed herein, in certain embodiments, are methods of treating an urothelial cancer, bladder cancer, ureter cancer, renal pelvic cancer, kidney cancer or any combination thereof in an individual in need thereof, comprising administering to the individual a combination comprising an ETBR antagonist as described herein and an additional therapeutic agent. In some embodiments, the additional therapeutic agent is an anti-oncologic agent. In some embodiments, the anti-oncologic agent is an immune checkpoint inhibitor, e.g., an anti-PD1 antibody or anti-PD-L1 antibody. In some embodiments, the combination comprises an amount of an immune checkpoint inhibitor and a synergistically effective amount of an ETBR antagonist or a specifically deuterated ETBR antagonist, such as BQ-788. In some embodiments, the immune checkpoint inhibitor is an anti-PD1 antibody.

In some embodiments, an ETBR antagonist is administered 2, 3, 4, or 5 times as frequently as the additional anti-oncologic agent. In some embodiments, the ETBR antagonist is administered 3 times during 1-3 weeks (e.g, about 2-3 weeks or about 21 days) while the additional anti-oncologic agent is administered 1 time during the 1-3 weeks (e.g., about 2-3 weeks or about 21 days).

In some embodiments, the ETBR antagonist is BQ-788, A192621, A-308165, IRL-1038, IRL-2500, RO-468443, BQ-017, or a structural analog thereof and the immune checkpoint inhibitor is an anti-PD-1 agent or an anti-CTLA4 agent. In some embodiments, the ETBR antagonist is BQ-788 or any modified versions thereof (e.g., a deuterated BQ-788, such as BQ-788A, BQ-788 B, and BQ-788C) and the anti-oncologic agent is an anti-PD1 antibody, anti-PD-L1 antibody, anti-CTLA4 antibody, or any combination thereof.

In some embodiments, the combination of the ETBR antagonist and the anti-oncologic agent results in a synergistic effect in that the combination achieves at least one of: a greater therapeutic effect (i.e., more efficacious) than the additive therapeutic effect obtained by administration of the constituent ingredients alone, a greater therapeutic effect than achieved by administration of a higher dose of the constituent ingredients alone, a similar or greater therapeutic effect but with a decrease in adverse events or side effects relative to that observed by administration of the constituent ingredients alone (i.e., improved therapeutic window), or increased duration of effects, or a similar or greater therapeutic effect at a smaller dose of one or both of the constituent ingredients or a combination thereof. In some embodiments, the synergistic effect is increased survival time, increased tumor stability or volume reduction, or increased anti-tumor activity as compared to single agent therapy alone.

In some embodiments, the combination of the ETBR antagonist and the anti-oncologic agent yields improved anti-tumor results as compared to single agent therapy alone. For example, the combination of the ETBR antagonist and the anti-oncologic agent increases anti-tumor activity, increased survival, or increased tumor stability as compared to either agent alone. In some embodiments, tumor reduction is at least 1-fold, 2-fold, 3-fold, 4-fold, 5-fold, 6-fold, 7-fold, 8-fold, 9-fold, or up to 10-fold greater as compared to administration of an ETBR antagonist alone or the anti-oncologic agent alone, such as a checkpoint inhibitor. In some embodiments, survival is at least 1-fold, 2-fold, 3-fold, 4-fold, 5-fold, 6-fold, 7-fold, 8-fold, 9-fold, or up to 10-fold greater as compared to administration of an ETBR antagonist alone or the anti-oncologic agent alone, such as a checkpoint inhibitor. In some embodiments, survival is increased from about 1 week, 1 month, 2 months, 3 months, 4 months, 5 months, 6 months, 7 months, 8 months, 1 year, 2 years, 3 years, 4 years, 5 years, 10 years, 15 years, 20 years, or up to about 30 years more as compared to administration of an ETBR antagonist alone or the anti-oncologic agent alone, such as a checkpoint inhibitor.

In some embodiments, the individual has undergone a prior cancer treatment. In some embodiments, the individual is resistant to immunotherapy prior to being administered the ETBR antagonist. For example, the subject may be resistant to immunotherapy and receive a compound, such as an ETBR antagonist, as part of a combination therapy with any number of additional therapeutic agents. In some embodiments, the ETBR antagonist is administered in combination with an anti-oncologic agent, an anti-bacterial agent, an anti-microbial agent, or any combination thereof. In some embodiments, the ETBR antagonist is administered with an anti-oncologic agent. In some embodiments, the ETBR antagonist is administered with an anti-bacterial agent. In some embodiments, the ETBR antagonist is administered with an anti-microbial agent. In some embodiments, the ETBR antagonist is administered with an immune checkpoint inhibitor. In some embodiments, the method further comprises: surgery, chemotherapy, or radiation therapy.

In some embodiments, the anti-oncologic agent is an immunosuppressive agent, or an immunostimulatory agent. In some embodiments, the immunostimulant is a vaccine, colony stimulating agent, interferon, interleukin, virus, antigen, co-stimulatory agent, immunogenicity agent, immunomodulator, or immunotherapeutic agent. In some embodiments, the immunostimulant is a cytokine such as an interleukin.

In some embodiments, an antibiotic is administered as part of a combination therapy. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a $3^{rd}$ or $4^{th}$ generation, can be cephalosporin or a quinolone. Exemplary antibiotics are doxorubicin, bleomycin, dactinomycin, daunorubicin, mithramycin, mitomycin, mytomycin C, and daunomycin to name a few.

In some embodiments, an anti-fungal is administered as part of a combination therapy. Antifungals can be drugs that can kill or prevent the growth of fungi. In some embodiments, the target of the antifungal agents is sterol biosynthesis, DNA biosynthesis, or β-glucan biosynthesis. In some embodiments, the antifungal is a folate synthesis inhibitor or a nucleic acid cross-linking agent. In some embodiments, the folate synthesis inhibitor is a sulpha based drug. In some embodiments, the folate synthesis inhibitor is an agent that inhibits a fungal synthesis of folate or a competitive inhibitor. In some embodiments, the sulpha based drug, or folate synthesis inhibitor, is methotrexate or sulfamethaxazole. In some embodiments, the antifungal is a nucleic acid cross-linking agent. In some embodiments, the cross-linking agent inhibits a DNA or RNA process in fungi. In some embodiments, an antifungal agent is from a class of polyene, azole, allylamine, or echinocandin. In some embodiments, a polyene antifungal is amphotericin B, candicidin, filipin, hamycin, natamycin, nystatin, or rimocidin. In some embodiments, the antifungal is from an azole family. In some embodiments, the azole antifungal inhibits lanosterol 14 α-demethylase. In some embodiments the azole antifungal is an imidazole such as bifonazole, butoconazole, clotrimazole, econazole, fenticonazole, isoconazole, ketoconazole, luliconazole, miconazole, omoconazole, oxiconazole, sertaconazole, sulcoazole, or tioconazole. In some embodiments, the azole antifungal is a triazole such as albaconazole, efinaconazole, epoxiconazole, fluconazole, isavuvonazole, itraconazole, posaconazole, propiconazole, ravuconazole, terconazole, or voriconazole. In some embodiments an azole is a thiazole such as abafungin. In some embodiments, the antifungal is an allylamine such as amorolfin, butenafine, naftifine, or terbinafine. In some embodiments, the antifungal is an echinocandin such as anidulafungin, caspofungin, or micafungin. In some embodiments, the antifungal is an aurone, benzoic acid, ciclopirox, flucytosine, griseofulvin, haloprogin, tolnaftate, undecylenic acid, cystal violet or balsam of Peru. A person of skill in the art can appropriately determine which known antifungal medication to apply based on the fungus infecting the individual.

In some embodiments, an anti-viral agent may be administered as part of a treatment regime. In some embodiments, a herpes virus prophylaxis is administered to a subject in need thereof as part of a treatment regime. In some embodiments, the herpes virus prophylaxis is valacyclovir (Valtrex). Valtrex can be used orally to prevent the occurrence of herpes virus infections in subjects with positive HSV serology.

In some embodiments, the anti-oncologic agent is a bRaf inhibitor, an immune checkpoint inhibitor, a caspase-8 inhibitor, an ETAR antagonist, niacinamide, a chemotherapeutic agent such as, e.g., a taxane, a kinase inhibitor, or other receptor antagonist or combination thereof.

In some embodiments, the at least one anti-oncologic agent is an immune checkpoint inhibitor. In some embodiments, the immune checkpoint inhibitor is an anti-PD1 antibody or an anti-PD-L1 antibody. In some embodiments, the anti-PD1 antibody is at least one of nivolumab, pembrolizumab, pidilizumab, or any combination thereof. In some embodiments, the anti-PD-L1 antibody is atezolizumab, MDX-1105, avelumab, durvalumab, or any combination thereof. In some embodiments, the immune checkpoint target is PD-1, CTLA-4, ADORA2A, CD276, VTCN1, BTLA, IDO1, KIR3DL1, LAG3, HAVCR2, VISTA, CD244, AAVS1, CCR5, LAIR1, TIGIT, or any combination thereof.

In some embodiments, the bRAF inhibitor is at least one of dabrafenib, sorafenib, vemurafenib, or any other bRAF inhibitor known or that becomes known to one skilled in the art.

In some embodiments, caspase-8 is a downstream effector of the ETBR, and caspase-8 inhibitors block molecular events that promote invasion and metastasis that are triggered as a result of ETBR activation. As such, caspase-8 inhibitors can be classified as a caspase-8 antagonist or an antagonist/inhibitor of ETBR signaling. In some embodiments, the caspase-8 inhibitor peptide has a sequence of Ac-AAVALLPAVLLAALAPIETD-CHO, which is commercially available from EMD Millipore (Billerica, MA 01821, USA).

In some embodiments, the anti-oncologic agent is an alkylating agent. An alkylating agent can alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. In some embodiments, other cytotoxic/anti-neoplastic agents are utilized. In some embodiments, the cytotoxic/antineoplastic agents are antimetabolites for tumor cells, e.g., cytosine arabinoside, fluorouracil, methotrexate, mercaptopuirine, azathioprime, and procarbazine. In some embodiments, the agent is a mitotic inhibitor (e.g., vinca alkaloids). In some embodiments, the agent is vincristine, vinblastine or etoposide. In some embodiments, the anti-oncologic agent comprises taxol and its derivatives, L-asparaginase, anti-tumor antibodies, dacarbazine, azacytidine, amsacrine, melphalan, VM-26, ifosfamide, mitoxantrone, or vindesine.

In some embodiments, the combination is comprised within one or more unit dosage forms. In further embodiments, the combination is administered in separate unit dosage forms, for example, a first container comprising the at least one ETBR antagonist, and a second container comprising the at least one anti-oncologic agent, such as an immune checkpoint inhibitor.

In some embodiments, the combination of the ETBR antagonist and the additional therapeutic agent is administered as a single pharmaceutical composition. In some embodiments, the pharmaceutical composition comprises an effective amount (e.g., a synergistically effective amount) of at least two of an ETBR antagonist, bRaf inhibitor, an immune checkpoint inhibitor, a caspase-8 inhibitor, an ETAR antagonist, niacinamide, a chemotherapeutic agent such as, e.g., a taxane, a kinase inhibitor, or other receptor antagonist or combination thereof.

In some embodiments, the pharmaceutical compositions are delivered intravenously, intramuscularly, subcutaneously, orally, intranasally, sublingually, transdermally, topically, intraperitoneally, parenterally, intranasally, or intracranially. In some embodiments, pharmaceutical compositions provided herein are administered orally, intravenously, intravesically, intrathecally, intracavernously, intramuscularly, topically, via inhalation, rectally, intradermally, or any combination thereof.

In some embodiments, the additional anti-oncologic agent is at least one of apx005m, ipilimumab, vemurafenib, dacabazine, nivolumab, pembrolizumab, niacinamide, interleukin-2, DEDN6526, Talimogene laherparepvec, tumor infiltrating lymphocytes, an anti-angiogenic agent, adriamycin, camptothecin, carboplatin, cisplatin, daunorubicin, doxorubicin, alpha, beta, or gamma interferon, irinotecan, docetaxel, paclitaxel, topotecan, atrasentan, tezosentan, bosentan, sitaxsentan, enrasentan, zibotentan, Ro468443, TBC10950, TBC10894, A192621, A308165, SB209670, SB17242, A182086, (s)-Lu302872, J-104132, TAK-044, Sarafotoxin 56c, IRL2500, RES7011, Aselacins A, B, and C, Ro470203, Ro462005, sulfamethoxazole, cochinmicin I, II, and III, L749329, L571281, L754142, J104132, CGS27830, PD142893, PD143296, PD145065, PD156252, PD159020, PD160672, PD160874, TM-ET-1, IRL3630, Ro485695, L75037, LU224332, PD142893, LU302872, PD145065, Ro610612, SB217242, or combinations thereof. In some embodiments, the additional anti-oncologic agent is a RAF kinase antagonist, a MEK antagonist or a combination thereof. In some embodiments, the anti-oncologic agent is at least one of an IDO inhibitor, HDAC inhibitor, DNMT inhibitor, adenosine receptor inhibitor, CXCR4/CXCL12 axis inhibitor or a combination thereof. In some embodiments, the DNMT inhibitor is vidaza. In some embodiments, the HDAC inhibitor is at least one of entinostat, mocetinostat, inostat, romidepsin, ACY-241, farydak or a combination thereof. In some embodiments, the adenosine receptor inhibitor is at least one of CPI-444 (V81444), PBF-509, MEDI9447, MK-3814, AZD4635, BMS-986179 or a combination thereof. In some embodiments, the CXCR4/CXCL12 axis inhibitor is at least one of ulocuplumab, BL-8040, PF-06747143, POL6326, plerixafor, ALX-0651, LY2510924, AMD11070, X4P-001, Q122, USL311, burixafor hyrobromid, CX-01, CTCE 9908, GMI-1359 or a combination thereof. In some embodiments, the anti-oncologic agent is an anti-angiogenic agent selected from thalidomide, marimastat, COL-3, BMS275291, squalamine, 2-ME, SU6668, neovastat, Medi522, EMD121974, CAI, celecoxib, interleukin-12, IM862, TNP470, avastin, gleevac, herceptin, or a combination thereof. In some embodiments, the anti-oncologic agent is a cell CDK4/6 cycle inhibitor, for example, ribociclib, palbociclib, milciclib, voruciclib, abemaciclib, flavopiridol or a combination thereof.

In some embodiments, the anti-oncologic agent comprises an immunotherapy agent or an immune based therapy. In some embodiments, the immune based therapy includes at least one of an immune checkpoint inhibitor (e.g., an anti-PD-1 antibody), a cancer vaccine, a Chimeric Antigen Receptor Cell (CAR) therapy, an engineered T cell receptor (TCR) therapy, or a combination thereof. In some embodiments, the immunotherapy agent comprises a Chimeric Antigen Receptor Cell (CAR) therapy. In some embodiments, the CAR therapy comprises administering immune effector cells (e.g., T cells, NK cells) engineered to express a CAR that binds to a tumor antigen to treat cancer associated with expression of said tumor antigen. In some embodiments, the CAR comprises an antigen binding domain (e.g., an antibody, antibody fragment, or extracellular single-chain variable fragment (scFv)) that binds to a tumor antigen, a transmembrane domain, and an intracellular signaling domain (e.g., an intracellular signaling domain comprising a costimulatory domain and/or a primary signaling domain). In some embodiments, the tumor antigen is associated with urothelial or kidney cancer. In some embodiments, the tumor antigen is carbonic anhydrase IX (CAIX) or Prostate stem cell antigen (PSCA). In some embodiments, the immune based therapy comprises administering T cells or NK cells, for example, expressing knocked-in genes of interest (e.g., genes encoding neoantigen-targeting TCRs). In some embodiments, the immune based therapy comprises administering T cells or NK cells, for example, knocked out for specific antigen genes (e.g., PD-1).

In some embodiments, the combination of the ETBR antagonist and the additional therapeutic agent is administered in separate pharmaceutical compositions.

In some embodiments, the method comprises administering: (a) a first composition comprising an effective amount of an ETBR antagonist and a pharmaceutically acceptable carrier or excipient; and (b) a second composition comprising an effective amount of at least one additional anti-oncologic agent, and a pharmaceutically acceptable carrier or excipient, wherein the administering demonstrates synergistic anti-cancer activity. In some embodiments, the ETBR antagonist is a deuterated BQ-788 as described herein.

In some embodiments, the physiologic role of the ETBR is to clear excess levels of endothelin-1 (ET-1), from the circulation. Without being bound by any particular theory, it is hypothesized that administering an ETBR antagonist prevents ET-1 clearance and elevates serum ET-1 levels. Elevated serum levels of ET-1 are associated with a variety of adverse effects due to its activation of the Endothelin A receptor (ETAR) including, hypertension, pulmonary hypertension and renal vasoconstriction. In some embodiments, in order to minimize the unwanted effect of ETAR activation, the description provides pharmaceutical compositions and methods for combination therapy (in a single dosage form or separate dosage forms administered approximately contemporaneously) of an ETBR antagonist with an ETAR antagonist. The ETAR antagonist acts synergistically to enhance the beneficial effects of an ETBR antagonist while minimizing adverse events or side effects. It was also surprising that an effective amount (e.g., a synergistically effective amount) of niacinamide was effective at synergistically minimizing adverse events or side effects, such as weight loss, from the specifically deuterated ETBR antagonist. The formulations as described herein are useful for the treatment of cancer in a patient, for example, breast cancer, bladder cancer, urothelial cancer, renal pelvic cancer, kidney cancer, melanoma, SCC, glioblastoma; solid tumors or a combination thereof.

In some embodiments, the ETAR antagonist is BQ123. BQ123 (2-[(3R,6R,9S,12R,15S)-6-(1H-indol-3-ylmethyl)-9-(2-methylpropyl)-2,5,8,11,14-pentaoxo-12-propan-2-yl-1,4,7,10,13-pentazabicyclo[13.3.0]octadecan-3-yl]acetic acid or cyclo(D-Trp-D-Asp-Pro-D-Val-Leu)) is a selective ETAR antagonist. (Ishikawa et al., (1992). "Cyclic pentapeptide endothelin antagonists with high ETA selectivity. Potency- and solubility-enhancing modifications." Journal of Medicinal Chemistry 35 (11): 1239-42, which is incorporated herein by reference). BQ123 is available commercially from, e.g., ABI Chem (ACIL9EDH).

In some embodiments, the method comprises administering an effective amount of an ETBR antagonist in combination with an effective amount of an ETAR antagonist, and a pharmaceutically acceptable carrier. In some embodiments, the effective amount of an ETAR antagonist is a synergistically effective amount. In some embodiments, the ETBR antagonist is at least one of a deuterated form of BQ-788, A192621, or a combination thereof, including analogs, derivatives, polymorphs, prodrugs, and salts thereof. In some embodiments, the ETAR antagonist is BQ123, including analogs, derivatives, polymorphs, prodrugs, and salts thereof.

In some embodiments, a dosage of the ETBR antagonist is about 0.1 μg to about 500 mg (e.g., about 100 μg to about 4000 μg) and/or a concentration of the ETBR antagonist is about 0.01 μg/mL to about 1000 mg/mL of the composition (e.g., about 0.1 mg/mL to about 5 mg/mL).

In some embodiments, a dosage of the ETAR antagonist is about 0.1 μg to about 500 mg (e.g., about 100 μg to about 4000 μg) and/or a concentration of the ETAR antagonist is about 0.01 μg/mL to about 1000 mg/mL of the composition (e.g., about 0.1 mg/mL to about 5 mg/mL).

In some embodiments, a dosage of the anti-PD1 antibody is about 0.1 μg to about 500 mg (e.g., about 100 μg to about 4000 μg) and/or a concentration of the anti-PD1 antibody is about 0.01 μg/mL to about 1000 mg/mL of the composition (e.g., about 0.1 mg/mL to about 5 mg/mL).

In some embodiments, a dosage of the bRAF inhibitor is about 0.1 μg to about 500 mg (e.g., about 100 μg to about 4000 μg) and/or a concentration of the bRAF inhibitor is about 0.01 μg/mL to about 1000 mg/mL of the composition (e.g., about 0.1 mg/mL to about 5 mg/mL).

In some embodiments, a dosage of the niacinamide is about 0.1 μg to about 500 mg (e.g., about 100 μg to about 4000 μg) and/or a concentration of the niacinamide is about 0.01 μg/mL to about 1000 mg/mL of the composition (e.g., about 0.1 mg/mL to about 5 mg/mL).

In some embodiments, a dosage of the caspase-8 inhibitor is about 0.1 μg to about 500 mg (e.g., about 100 μg to about 4000 μg or about 1 μg to about 4000 μg) and/or a concentration of the caspase-8 inhibitor is about 0.01 μg/mL to about 1000 mg/mL of the composition (e.g., about 0.1 mg/mL to about 5 mg/mL).

In some embodiments, the concentration of the at least one specifically deuterated ETBR antagonist, and/or the at least one anti-oncologic agent can independently be about 0.01 μg/mL to about 1000 mg/mL, about 0.01 μg/mL to about 750 mg/mL, about 0.01 μg/mL to about 500 mg/mL, about 0.01 μg/mL to about 300 mg/mL, about 0.01 μg/mL to about 150 mg/mL, about 0.01 μg/mL to about 100 mg/mL, about 0.01 μg/mL to about 50 mg/mL, about 0.01 μg/mL to about 25 mg/mL, about 0.01 μg/mL to about 10 mg/mL, about 0.01 μg/mL to about 1.0 mg/mL, about 0.01 μg/mL to about 0.1 μg/mL, about 0.1 μg/mL to about 750 mg/mL, about 0.1 μg/mL to about 500 mg/mL, about 0.1 μg/mL to about 300 mg/mL, about 0.1 μg/mL to about 150 mg/mL, about 0.1 μg/mL to about 100 mg/mL, about 0.1 μg/mL to about 50 mg/mL, about 0.1 μg/mL to about 25 mg/mL, about 0.1 μg/mL to about 10 mg/mL, about 0.1 μg/mL to about 1.0 mg/mL, about 1.0 μg/mL to about 750 mg/mL, about 1.0 μg/mL to about 500 mg/mL, about 1.0 μg/mL to about 300 mg/mL, about 1.0 μg/mL to about 150 mg/mL, about 1.0 μg/mL to about 100 mg/mL, about 1.0 μg/mL to about 50 mg/mL, about 1.0 μg/mL to about 25 mg/mL, about 1.0 μg/mL to about 10 mg/mL, about 10 μg/mL to about 750 mg/mL, about 10 μg/mL to about 500 mg/mL, about 10 μg/mL to about 300 mg/mL, about 10 μg/mL to about 150 mg/mL, about 10 μg/mL to about 100 mg/mL, about 10 μg/mL to about 50 mg/mL, about 10 μg/mL to about 25 mg/mL, about 25 μg/mL to about 750 mg/mL, about 25 μg/mL to about 500 mg/mL, about 25 μg/mL to about 300 mg/mL, about 25 μg/mL to about 150 mg/mL, about 25 μg/mL to about 100 mg/mL, about 25 μg/mL to about 50 mg/mL, about 50 μg/mL to about 750 mg/mL, about 50 μg/mL to about 500 mg/mL, about 50 μg/mL to about 300 mg/mL, about 50 μg/mL to about 150 mg/mL, about 50 μg/mL to about 100 mg/mL, about 100 μg/mL to about 750 mg/mL, about 100 μg/mL to about 500 mg/mL, about 100 μg/mL to about 300 mg/mL, about 100 μg/mL to about 150 mg/mL, about 150 μg/mL to about 750 mg/mL, about 150 μg/mL to about 500 mg/mL, about 150 μg/mL to about 300 mg/mL, about 300 μg/mL to about 750 mg/mL, about 300 μg/mL to about 500 mg/mL, or about 500 μg/mL to about 750 mg/mL.

In some embodiments, the dosage of the at least one specifically deuterated ETBR antagonist, and/or at least one anti-oncologic agent can independently be about 0.1 μg to about 5000 μg, about 0.1 μg to about 4500 μg, about 0.1 μg to about 4000 μg, about 0.1 μg to about 3500 μg, about 0.1 μg to about 3000 μg, about 0.1 μg to about 2500 μg, about 0.1 μg to about 2000 μg, about 0.1 μg to about 1500 μg, about 0.1 μg to about 1000 μg, about 0.1 μg to about 500 μg, about 1.0 μg to about 5000 μg, about 1.0 μg to about 4500 μg, about 1.0 μg to about 4000 μg, about 1.0 μg to about 3500 μg, about 1.0 μg to about 3000 μg, about 1.0 μg to about 2500 μg, about 1.0 μg to about 2000 μg, about 1.0 μg to about 1500 μg, about 1.0 g to about 1000 μg, about 1.0 μg to about 500 μg, about 100 μg to about 5000 μg, about 100 μg to about 4500 μg, about 100 μg to about 4000 μg, about 100 μg to about 3500 μg, about 100 μg to about 3000 μg, about 100 μg to about 2500 μg, about 100 μg to about 2000 μg, about 100 μg to about 1500 μg, about 100 μg to about 1000 μg, about 100 μg to about 500 μg, about 250 μg to about 5000 μg, about 250 μg to about 4500 μg, about 250 μg to about 4000 μg, about 250 μg to about 3500 μg, about 250 μg to about 3000 μg, about 250 μg to about 2500 μg, about 250 μg to about 2000 μg, about 250 μg to about 1500 μg, about 250 μg to about 1000 μg, about 250 μg to about 500 μg, about 500 μg to about 5000 μg, about 500 μg to about 4500 μg, about 500 μg to about 4000 μg, about 500 μg to about 3500 μg, about 500 μg to about 3000 μg, about 500 μg to about 2500 μg, about 500 μg to about 2000 μg, about 500 μg to about 1500 μg, about 500 μg to about 1000 μg, about 750 μg to about 5000 μg, about 750 μg to about 4500 μg, about 750 μg to about 4000 μg, about 750 μg to about 3500 μg, about 750 μg to about 3000 μg, about 750 μg to about 2500 μg, about 750 μg to about 2000 μg, about 75 μg to about 1500 μg, about 750 μg to about 1000 μg, about 1500 μg to about 5000 μg, about 1500 μg to about 4500 μg, about 1500 μg to about 4000 μg, about 1500 μg to about 3500 μg, about 1500 μg to about 3000 μg, about 1500 μg to about 2500 μg, about 1500 μg to about 2000 μg, about 2000 μg to about 5000 μg, about 2000 μg to about 4500 μg, about 2000 μg to about 4000 μg, about 2000 μg to about 3500 μg, about 2000 μg to about 3000 μg, about 2000 μg to about 2500 μg, about 2500 μg to about 5000 μg, about 2500 μg to about 4500 μg, about 2500 μg to about 4000 μg, about 2500 μg to about 3500 μg, about 2500 μg to about 3000 μg, about 3000 μg to about 5000 μg, about 3000 μg to about 4500 μg, about 3500 μg to about 4000 μg, about 3500 μg to about 5000 μg, about 3500 μg to about 4500 μg, about 3500 μg to about 4000 μg, about 4000 μg to about 5000 μg, about 4000 μg to about 4500 μg, or about 4500 μg to about 5000 μg.

In some embodiments, a dosage of the anti-PD1 antibody is about 0.1 mg/kg to about 9.0 mg/kg. For example, the dosage of the anti-PD1 antibody is about 0.1 mg/kg to about 9.0 mg/kg, about 0.1 mg/kg to about 8.0 mg/kg, about 0.1 mg/kg to about 7.0 mg/kg, about 0.1 mg/kg to about 6.0 mg/kg, about 0.1 mg/kg to about 5.0 mg/kg, about 0.1 mg/kg to about 4.0 mg/kg, about 0.1 mg/kg to about 3.0 mg/kg, about 0.1 mg/kg to about 2.0 mg/kg, about 0.1 mg/kg to about 1.0 mg/kg, about 1.0 mg/kg to about 9.0 mg/kg, about 1.0 mg/kg to about 8.0 mg/kg, about 1.0 mg/kg to about 7.0 mg/kg, about 1.0 mg/kg to about 6.0 mg/kg, about 1.0 mg/kg to about 5.0 mg/kg, about 1.0 mg/kg to about 4.0 mg/kg, about 1.0 mg/kg to about 3.0 mg/kg, about 1.0 mg/kg to about 2.0 mg/kg, about 2.0 mg/kg to about 9.0 mg/kg, about 2.0 mg/kg to about 8.0 mg/kg, about 2.0 mg/kg to about 7.0 mg/kg, about 2.0 mg/kg to about 6.0 mg/kg, about 2.0 mg/kg to about 5.0 mg/kg, about 2.0 mg/kg to about 4.0 mg/kg, about 2.0 mg/kg to about 3.0 mg/kg, about 3.0 mg/kg to about 9.0 mg/kg, about 3.0 mg/kg to about 8.0 mg/kg, about 3.0 mg/kg to about 7.0 mg/kg, about 3.0 mg/kg to about 6.0 mg/kg, about 3.0 mg/kg to about 5.0 mg/kg, about 3.0 mg/kg to about 4.0 mg/kg, about 4.0 mg/kg to about 9.0 mg/kg, about 4.0 mg/kg to about 8.0 mg/kg, about 4.0 mg/kg to about 7.0 mg/kg, about 4.0 mg/kg to about 6.0 mg/kg, about 4.0 mg/kg to about 5.0 mg/kg, about 5.0 mg/kg to about 9.0 mg/kg, about 5.0 mg/kg to about 8.0 mg/kg, about 5.0 mg/kg to about 7.0 mg/kg, about 5.0 mg/kg to about 6.0 mg/kg, about 6.0 mg/kg to about 9.0 mg/kg, about 6.0 mg/kg to about 8.0 mg/kg, about 6.0 mg/kg to about 7.0 mg/kg, about 7.0 mg/kg to about 9.0 mg/kg, about 7.0 mg/kg to about 8.0 mg/kg, or about 8.0 mg/kg to about 9.0 mg/kg.

In some embodiments, a dosage of the bRAF inhibitor is about 1 mg to about 1500 mg. For example, the dosage of the bRAF inhibitor about 1 mg to about 1500 mg, about 1 mg to about 1250 mg, about 1 mg to about 1000 mg, about 1 mg to about 750 mg, about 1 mg to about 500 mg, about 1 mg to about 250 mg, about 250 mg to about 1500 mg, about 250 mg to about 1250 mg, about 250 mg to about 1000 mg, about 250 mg to about 750 mg, about 250 mg to about 500 mg, about 500 mg to about 1500 mg, about 500 mg to about 1250 mg, about 500 mg to about 1000 mg, about 500 mg to about 750 mg, about 750 mg to about 1500 mg, about 750 mg to about 1250 mg, about 750 mg to about 1000 mg, about 1000 mg to about 1500 mg, about 1000 mg to about 1250 mg, or about 1250 mg to about 1500 mg.

In some embodiments, a dosage of the niacinamide is about 1 mg to about 3000 mg. For example, the dosage of the niacinamide is about 1 mg to about 3000 mg, about 1 mg to about 2750 mg, about 1 mg to about 2500 mg, about 1 mg to about 2250 mg, about 1 mg to about 2000 mg, about 1 mg to about 1750 mg, about 1 mg to about 1500 mg, about 1 mg to about 1250 mg, about 1 mg to about 1000 mg, about 1 mg to about 750 mg, about 1 mg to about 500 mg, about 1 mg to about 250 mg, about 250 mg to about 3000 mg, about 250 mg to about 2750 mg, about 250 mg to about 2500 mg, about 250 mg to about 2250 mg, about 250 mg to about 2000 mg, about 250 mg to about 1750 mg, about 250 mg to about 1500 mg, about 250 mg to about 1250 mg, about 250 mg to about 1000 mg, about 250 mg to about 750 mg, about 250 mg to about 500 mg, about 500 mg to about 3000 mg, about 500 mg to about 2750 mg, about 500 mg to about 2500 mg, about 500 mg to about 2250 mg, about 500 mg to about 2000 mg, about 500 mg to about 1750 mg, about 500 mg to about 1500 mg, about 500 mg to about 1250 mg, about 500 mg to about 1000 mg, about 500 mg to about 750 mg, about 750 mg to about 3000 mg, about 750 mg to about 2750 mg, about 750 mg to about 2500 mg, about 750 mg to about 2250 mg, about 750 mg to about 2000 mg, about 750 mg to about 1750 mg, about 750 mg to about 1500 mg, about 750 mg to about 1250 mg, about 750 mg to about 1000 mg, about 1000 mg to about 3000 mg, about 1000 mg to about 2750 mg, about 1000 mg to about 2500 mg, about 1000 mg to about 2250 mg, about 1000 mg to about 2000 mg, about 1000 mg to about 1750 mg, about 1000 mg to about 1500 mg, about 100 mg to about 1250 mg, about 1250 mg to about 3000 mg, about 1250 mg to about 2750 mg, about 1250 mg to about 2500 mg, about 1250 mg to about 2250 mg, about 1250 mg to about 2000 mg, about 1250 mg to about 1750 mg, about 1250 mg to about 1500 mg, about 1500 mg to about 3000 mg, about 1500 mg to about 2750 mg, about 1500 mg to about 2500 mg, about 1500 mg to about 2250 mg, about 1500 mg to about 2000 mg, about 1500 mg to about 1750 mg, about 1750 mg to about 3000 mg, about 1750 mg to about 2750 mg, about 1750 mg to about 2500 mg, about 1750 mg to about 2250 mg, about 1750 mg to about 2000 mg, about 2000 mg to about 3000 mg, about 2000 mg to about 2750 mg, about 2000 mg to about 2500 mg, about 2000 mg to about 2250 mg, about 2250 mg to about 3000 mg, about 2250 mg to about 2750 mg, about 2250 mg to about 2500 mg, about 2500 mg to about 3000 mg, about 2500 mg to about 2750 mg, or about 2750 mg to about 3000 mg.

Routes of Administration

Disclosed herein, in certain embodiments, are routes of administration for the pharmaceutical compositions disclosed herein. In some embodiments, a pharmaceutical composition disclosed herein is administered in single or divided doses by the oral, parenteral or topical routes. In some embodiments, administration of the pharmaceutical composition ranges from continuous (e.g., intravenous drip) to several oral administrations per day (for example, Q.O.D. or Q.I.D.). In some embodiments, administration of the pharmaceutical composition comprises oral, topical, parenteral, intramuscular, intravenous, sub-cutaneous, transdermal (which may include a penetration enhancement agent), buccal, sublingual or suppository administration. In some embodiments, enteric coated oral tablets are administered to enhance bioavailability of the pharmaceutical composition from an oral route of administration. The most effective dosage form will depend upon the pharmacokinetics of the particular agent(s) chosen as well as the severity of disease in the patient. In some embodiments, the compounds disclosed herein are administered as sprays, mists, or aerosols for intra-nasal, intra-tracheal or pulmonary administration. In some embodiments, the pharmaceutical compositions are administered in immediate release, intermediate release or sustained or controlled release forms. In some embodiments, sustained or controlled release forms are administered orally. In some embodiments, sustained or controlled release forms are administered in suppository and transdermal or other topical forms. In some embodiments, pharmaceutical compositions provided herein are administered locally. In some embodiments, a local administration comprises an intravesicular administration. In other embodiments, a local administration comprises a direct injection at the disease site. In some embodiments, a local administration comprises using a catheter or a tubing that is inserted into a bladder area. In some embodiments, intramuscular injections in liposomal form are used to control or sustain the release of the compound at an injection site.

In some embodiments, a pharmaceutical composition described herein is administered orally, parenterally, by inhalation spray, topically, rectally, nasally, buccally, vaginally or via an implanted reservoir. In some embodiments, an administration of the pharmaceutical composition is orally, intravenously, intravesically, intrathecally, intracavernously, intramuscularly, topically, via inhalation, rectally, intradermally, or any combination thereof. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the pharmaceutical compositions are administered orally, intraperitoneally or intravenously.

In some embodiments, a compositions described herein is in a sterile injectable form. In some embodiments, the sterile injectable form comprises an aqueous or oleaginous suspension. In some embodiments, the suspension is formulated using suitable dispersing or wetting agents and suspending agents. In some embodiments, the sterile injectable preparation comprises a sterile injectable solution or suspension in a non-toxic parenterally-acceptable diluent, solvent, or suspending medium, for example as a solution in 1,3-butanediol. In some embodiments, the diluent or solvent is water, Ringer's solution, or isotonic sodium chloride solution. In some embodiments, the diluent or solvent is a sterile, fixed oil. In some embodiments, the suspending medium is a bland fixed oil, e.g., synthetic mono- or di-glycerides. In some embodiments, the injectable solution comprises a fatty acid, such as oleic acid and its glyceride derivatives, or a natural pharmaceutically-acceptable oils, such as olive oil, castor oil or soybean oil. In some embodiments the olive oil, castor oil or soybean oil is in its polyoxyethylated versions. In some embodiments, the injectable solution comprises a long-chain alcohol diluent or dispersant, such as Ph. Helv or similar alcohol.

In some embodiments, the pharmaceutical compositions described herein are orally administered in any orally acceptable dosage form (e.g., capsules, tablets, aqueous suspensions and solutions). In some embodiments, the orally acceptable dosage form comprises a carrier (e.g., lactose and corn starch). In some embodiments, the orally acceptable dosage form comprises a lubricating agent (e.g., magnesium stearate). In some embodiments, the orally acceptable dosage form comprises a diluent (e.g., lactose and dried corn starch). In some embodiments, the orally acceptable dosage form comprises an aqueous suspensions, in which the active ingredient is combined with emulsifying and suspending agents. In some embodiments sweetening, flavoring or coloring agents are added to the orally acceptable dosage form.

In some embodiments, the pharmaceutical compositions described herein are administered in the form of suppositories for rectal administration. In some embodiments, a suppository is prepared by mixing the active agent with a suitable non-irritating excipient, which is solid at room temperature but liquid at rectal temperature and therefore will melt in the rectum to release the drug. In some embodiments, the excipient is cocoa butter, beeswax or a polyethylene glycol.

In some embodiments, the pharmaceutical compositions as described herein are administered topically. Suitable topical formulations are readily prepared for each of these areas or organs. In some embodiments, topical application for the lower intestinal tract is effected in a rectal suppository formulation (see above). In some embodiments, topical application for the lower intestinal tract is effected in a suitable enema formulation. In some embodiments, topically-acceptable transdermal patches are used.

In some embodiments, for topical applications, the pharmaceutical compositions are formulated in a suitable ointment containing the active component suspended or dissolved in one or more carriers. In some embodiments, the carrier is mineral oil, liquid petrolatum, DMSO, white petrolatum, propylene glycol, polyoxyethylene, polyoxypropylene compound, emulsifying wax or water. In some embodiments, the compounds are coated onto a stent which is to be surgically implanted into a patient in order to inhibit or reduce the likelihood of occlusion occurring in the stent in the patient.

In some embodiments, the pharmaceutical compositions are formulated in a suitable lotion or cream containing the active components suspended or dissolved in one or more pharmaceutically acceptable carriers. In some embodiment the carrier is mineral oil, sorbitan monostearate, polysorbate 60, cetyl esters wax, cetearyl alcohol, 2-octyldodecanol, benzyl alcohol or water.

In some embodiments, for ophthalmic use, the pharmaceutical compositions are formulated as micronized suspensions in isotonic, pH adjusted sterile saline, or as solutions in isotonic, pH adjusted sterile saline, either with or without a preservative such as benzylalkonium chloride. In some embodiments, for ophthalmic uses, the pharmaceutical compositions are formulated in an ointment such as petrolatum.

In some embodiments, the pharmaceutical compositions described herein are administered by nasal aerosol or inhalation. In some embodiments nasal aerosol or inhalation formulations are prepared as solutions in saline, employing benzyl alcohol or other suitable preservatives, absorption promoters to enhance bioavailability, fluorocarbons, and/or other conventional solubilizing or dispersing agents. In some embodiments, the pharmaceutical compositions comprise liposomes including an effective amount (e.g., a synergistically effective amount) of an ETBR antagonist or a caspase-8 inhibitor or a combination thereof, and/or an effective amount (e.g., a synergistically effective amount) of an ETAR antagonist, an anti-PD1 antibody, a bRAF inhibitor, niacinamide or a combination thereof, wherein the liposome formulation is configured or adapted for intranasal delivery or sublingual delivery. In some embodiments, the liposomes further comprise an additional anti-cancer agent as described above.

In some embodiments, the compositions are formulated to contain between about 0.05 milligram to about 750 milligrams or more, for example about 1 milligram to about 600 milligrams, or about 10 milligrams to about 500 milligrams of active ingredient, alone or in combination with at least one other compound according to the present disclosure. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

In some embodiments, a patient or subject in need of therapy using compounds according to the methods described herein is treated by administering to the patient (subject) an effective amount of the compound according to the present disclosure including pharmaceutically acceptable salts, solvates or polymorphs thereof optionally in a pharmaceutically acceptable carrier or diluent, either alone, or in combination with other known erythopoiesis stimulating agents as otherwise identified herein.

In some embodiments, the compounds or compositions herein are administered orally, parenterally, intradermally, by an injection (intravenously, subcutaneously, or intramuscularly), topically, including transdermally, in liquid, cream, gel, or solid form, or by aerosol form.

In some embodiments, the active ingredients are included in the pharmaceutically acceptable carrier or diluent in an amount sufficient to deliver to a patient a therapeutically effective amount for the desired indication, without causing serious toxic effects in the patient treated. An exemplary dose of the active compound for all of the herein-mentioned conditions is in the range from about 10 ng/kg to 300 ng/kg, about 10 ng/kg to 1 μg/kg, about 1 μg/kg to 10 μg/kg, about 10 μg/kg to 100 μg/kg, about 100 μg/kg to 1000 μg/kg, about 1 mg/kg to 30 mg/kg, about 1 mg/kg to 300 mg/kg, or 0.1 to 100 mg/kg per day, more generally 0.5 to about 25 mg per kilogram body weight of the recipient/patient per day. A typical topical dosage will range from 0.01-5% wt/wt in a suitable carrier.

In some embodiments, the active ingredient herein is conveniently administered in any suitable unit dosage form. In some embodiments, the unit dosage form comprises less than 1 mg, 1 mg to 3000 mg, for example 5 to 500 mg of active ingredient per unit dosage form. In some embodiments, the unit dosage form is formulated for oral dosage and comprises about 25-250 mg of the active ingredient.

In some embodiments, the active ingredient is administered to achieve peak plasma concentrations of the active compound of about 0.00001-30 mM, for example about 0.1-30 μM. In some embodiments, the peak plasma concentrations are achieved by the intravenous injection of a solution or formulation of the active ingredient, optionally in saline, or an aqueous medium or administered as a bolus of the active ingredient. In some embodiments, peak plasma concentrations are achieved by oral administration.

Tertiary Lymphoid Organs (TLOs):

Disclosed herein are methods of forming a tertiary lymphoid organ (TLO) in a subject in need thereof. In some embodiments, disclosed herein are methods of forming a tertiary lymphoid organ (TLO) in a subject in need thereof, comprising administering to the subject a TLO-forming compound. Tertiary lymphoid organs are accumulations of lymphocytes and stromal cells in an organized structure that occur outside of secondary lymphoid organs (SLOs). The tertiary lymphoid organs disclosed herein are formed within (intratumoral) or adjacent (peritumoral) to tumors, or cancers, or at or near sites of inflammation such as chronic inflammation, chronic infection, atherosclerosis, chronic kidney diseases, allograft rejection such as transplanted organs undergoing graft rejection, autoimmune diseases, pathologies, autoimmune diseases such as systemic lupus erythematosus and rheumatoid arthritis, or autoimmune-related diseases. In some embodiments, the TLO is intratumoral. In some embodiments, the TLO is peritumoral. In some embodiments, tertiary lymphoid organ formation accelerates or improves efficacy of a cancer treatment, e.g., reducing a tumor volume or eradicating a tumor, and shortening the treatment time.

Also disclosed herein are methods of forming a tertiary lymphoid organ (TLO) in a subject in need thereof, comprising administering to the subject a TLO-forming compound disclosed herein. In some embodiments, the TLO-forming compound is an ETBR antagonist. In some embodiments, the ETBR antagonist is BQ-788, A192621, A-308165, IRL-1038, IRL-2500, RO-468443, BQ-017, or an analog thereof, or a combination thereof. In some embodiments, the ETBR antagonist is in a form of nanoparticles. In some embodiments, the ETBR antagonist is a non-deuterated BQ-788 analog. In some embodiments, the ETBR antagonist is not BQ-788. In some embodiments, the compound is administered, e.g., at different times, with at least one additional anti-oncologic therapeutic agent such as an immune checkpoint inhibitor, e.g., anti-PD1 antibody, anti-PD-L1 antibody, an anti-PD-1 agent, or any combination thereof. In some embodiments, the compound is in a pharmaceutically acceptable excipient that can comprise dimethyl sulfoxide (DMSO), LYOCELL (reversed cubic phase liquid crystal dispersion), soybean oil, INTRAVAIL (transmucosal absorption enhancement agents), PROTEK (protein stabilization excipients), or hydrogel, or any combination thereof. In some embodiments, tertiary lymphoid organs disclosed herein is formed within or adjacent to peripheral tissues, tumors, or cancers, or at or near sites of inflammation such as chronic inflammation, chronic infection, atherosclerosis, chronic kidney diseases, allograft rejection such as transplanted organs undergoing graft rejection, autoimmune diseases, pathologies, autoimmune diseases such as systemic lupus erythematosus and rheumatoid arthritis, or autoimmune-related diseases. In some embodiments, the TLO-forming compound is an endothelin A receptor (ETAR) antagonist, for example BQ123, BQ-610, A-127722, BSF-208075, BMS-182874, CI 1020, FR 139317, PD 151242, Sitaxsentan, ZD4054, and any combination thereof. In some embodiments, tertiary lymphoid organ formation may not be found in or after a tumor or cancer treatment. In some embodiments, tumor remnants in or after a cancer treatment may not form a tertiary lymphoid organ. In some embodiments, tertiary lymphoid organs form independently from a cancer treatment. In some embodiments, tertiary lymphoid organ formation accelerates or improves efficacy of a cancer treatment, e.g., reducing a tumor volume or eradicating a tumor, and shortening the treatment time.

Provided herein are methods of forming a tertiary lymphoid organ (TLO) within a urothelial or kidney cancer in a subject in need thereof. In some embodiments, methods of forming a tertiary lymphoid organ (TLO) within a urothelial or kidney cancer in a subject in need thereof comprise administering to a subject in need thereof, an ETBR antagonist. The ETBR antagonist can be selected from formula 1-formula 6. In some embodiments, the ETBR antagonist has the structure:

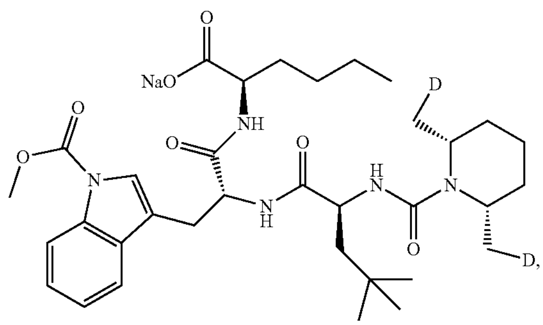

or a pharmaceutically acceptable salt thereof.

In some embodiments, the TLO-forming compound is an ETBR antagonist. In some embodiments, the ETBR antagonist is BQ-788, A192621, A-308165, IRL-1038, IRL-2500, RO-468443, BQ-017, or an analog thereof. In some embodiments, the ETBR antagonist is a compound of Formula (1), Formula (2), Formula (3), Formula (4), Formula (5), Formula (6), Formula (7), Formula (8) or Formula (9). In some embodiments, the ETBR antagonist is a non-deuterated BQ-788 analog. In some embodiments, the ETBR antagonist is not BQ-788.

In some embodiments, the TLO-forming compound is an endothelin A receptor (ETAR) antagonist. In some embodiments, the compound is BQ123, BQ-610, A-127722, BSF-208075, BMS-182874, CI 1020, FR 139317, PD 151242, Sitaxsentan, and/or ZD4054.

In some embodiments, the TLO-forming compound is in the form of nanoparticles. In some embodiments, the TLO-forming compound is in a pharmaceutically acceptable excipient that comprises dimethyl sulfoxide (DMSO), LYOCELL (reversed cubic phase liquid crystal dispersion), soybean oil, INTRAVAIL (transmucosal absorption enhancement agents), PROTEK (protein stabilization excipients), or hydrogel, or any combination thereof. In some embodiments, the TLO-forming compound is BQ-788 and is in the form of nanoparticles.

In some embodiments, the ETBR antagonist is administered by IV. In some embodiments, a composition comprising BQ-788 is administered by IV.

In some embodiments, the ETBR antagonist is administered at a low dose. In some embodiments, the ETBR antagonist is administered at a dose of about 50 μg/day to about 500 μg/day, about 50 μg/day to about 400 μg/day, about 50 μg/day to about 300 μg/day, about 50 μg/day to about 200 μg/day, about 100 μg/day to about 150 μg/day. In some embodiments, the ETBR antagonist is administered 3 days per week (i.e., 1 cycle). In some embodiments, the ETBR antagonist is administered for 6 cycles.

In some embodiments, the TLO-forming compound is administered with at least one additional anti-oncologic therapeutic agent. In some embodiments, the additional anti-oncolytic agent is an immune checkpoint inhibitor. In some embodiments, the immune checkpoint inhibitor is an anti-PD1 antibody. In some embodiments, the immune checkpoint inhibitor is an anti-PD-L1 antibody.

In some embodiments, tertiary lymphoid organ formation is not found in the subject after completion of treatment.

In some embodiments, the method comprises administering BQ-788 and an anti-PD-1 antibody. In some embodiments, the BQ-788 is administered as nanoparticles. In some embodiments, BQ-788 is not deuterated. In some embodiments, BQ-788 is administered as an IV formulation. In some embodiments, the BQ-788 is administered at a dose of between 50 μg and 200 μg/day for 3 days in a week (i.e., 1 cycle). In some embodiments, administration of a cycle of BQ-788 is repeated 1 time, 2 times, 3 times, 4 times, or 5 times.

Dosage Regimens and Dosage Forms

Provided herein, in certain embodiments, are treatment regimens for the treatment of urothelial, bladder, or kidney cancers in an individual in need thereof. In some embodiments, a treatment regimen provided herein comprises administering a dosage pharmaceutical composition comprising an active ingredient disclosed herein (e.g., an ETBR antagonist, an ETAR antagonist, an anti-PD1 antibody, a bRAF inhibitor, niacinamide, or a caspase-8 inhibitor). In some embodiments, the dosage pharmaceutical composition comprises about 100 μg to about 4000 μg of the active ingredient. In some embodiments, the dosage pharmaceutical composition is formulated as a sustained release dosage in which about 50 μg to about 3000 μg of the active ingredient is an initial burst, and in which about 50 μg to about 3000 μg of the active ingredient is a sustained release over 2 hours.

In some embodiments, the treatment regimen comprises administering a dosage pharmaceutical composition comprising a dosage of an ETBR antagonist of about 0.1 mg to about 500 mg (e.g., about 10 mg to about 100 mg), and/or a concentration of an ETBR antagonist of about 0.01 g/mL to about 1000 mg/mL (e.g., about 0.1 mg/mL to about 5 mg/mL).

In some embodiments, the at least one active ingredient is present in any of the dosage formulations described herein (e.g., initial burst, sustained release dosage, etc.) in about 100 μg to about 4000 μg, about 100 μg to about 3750 μg, about 100 μg to about 3500 μg, about 100 μg to about 3250 μg, about 100 μg to about 3000 μg, about 100 μg to about 2750 μg, about 100 μg to about 2500 μg, about 100 μg to about 2250 μg, about 100 μg to about 2000 μg, about 100 μg to about 1750 μg, about 100 μg to about 1500 μg, about 100 μg to about 1250 μg, about 100 μg to about 1000 μg, about 100 μg to about 750 μg, about 100 μg to about 500 μg, about 250 μg to about 4000 μg, about 250 μg to about 3750 μg, about 250 μg to about 3500 μg, about 250 μg to about 3250 μg, about 250 μg to about 3000 μg, about 250 μg to about 2750 μg, about 250 μg to about 2500 μg, about 250 μg to about 2250 μg, about 250 μg to about 2000 μg, about 250 μg to about 1750 μg, about 250 μg to about 1500 μg, about 250 μg to about 1250 μg, about 250 μg to about 1000 μg, about 250 μg to about 750 μg, about 250 μg to about 500 μg, about 500 μg to about 4000 μg, about 500 μg to about 3750 μg, about 500 μg to about 3500 μg, about 500 μg to about 3250 μg, about 500 μg to about 3000 μg, about 500 μg to about 2750 μg, about 500 μg to about 2500 μg, about 500 μg to about 2250 μg, about 500 μg to about 2000 μg, about 500 μg to about 1750 μg, about 500 μg to about 1500 μg, about 500 μg to about 1250 μg, about 500 μg to about 1000 μg, about 500 μg to about 750 μg, about 750 μg to about 4000 μg, about 750 μg to about 3750 μg, about 750 μg to about 3500 μg, about 750 μg to about 3250 μg, about 750 μg to about 3000 μg, about 750 μg to about 2750 μg, about 750 μg to about 2500 μg, about 750 μg to about 2250 μg, about 750 μg to about 2000 μg, about 750 μg to about 1750 μg, about 750 μg to about 1500 μg, about 750 μg to about 1250 μg, about 750 μg to about 1000 μg, about 1000 μg to about 4000 μg, about 1000 μg to about 3750 μg, about 1000 μg to about 3500 μg, about 1000 μg to about 3250 μg, about 1000 μg to about 3000 μg, about 1000 μg to about 2750 μg, about 1000 μg to about 2500 μg, about 1000 μg to about 2250 μg, about 1000 μg to about 2000 μg, about 1000 μg to about 1750 μg, about 1000 μg to about 1500 μg, about 1000 μg to about 1250 μg, about 1250 μg to about 4000 μg, about 1250 μg to about 3750 μg, about 1250 μg to about 3500 μg, about 1250 μg to about 3250 μg, about 1250 μg to about 3000 μg, about 1250 μg to about 2750 μg, about 1250 μg to about 2500 μg, about 1250 μg to about 2250 μg, about 1250 μg to about 2000 μg, about 1250 μg to about 1750 μg, about 1250 μg to about 1500 μg, about 1500 μg to about 4000 μg, about 1500 μg to about 3750 μg, about 1500 μg to about 3500 μg, about 1500 μg to about 3250 μg, about 1500 μg to about 3000 μg, about 1500 μg to about 2750 μg, about 1500 μg to about 2500 μg, about 1500 μg to about 2250 μg, about 1500 μg to about 2000 μg, about 1500 μg to about 1750 μg, about 1750 μg to about 4000 μg, about 1750 μg to about 3750 μg, about 1750 μg to about 3500 μg, about 1750 μg to about 3250 μg, about 1750 μg to about 3000 μg, about 1750 μg to about 2750 μg, about 1750 μg to about 2500 μg, about 1750 μg to about 2250 μg, about 1750 μg to about 2000 μg, about 2000 μg to about 4000 μg, about 2000 μg to about 3750 μg, about 2000 μg to about 3500 μg, about 2000 μg to about 3250 μg, about 2000 μg to about 3000 μg, about 2000 μg to about 2750 μg, about 2000 μg to about 2500 μg, about 2000 μg to about 2250 μg, about 2250 μg to about 4000 μg, about 2250 μg to about 3750 μg, about 2250 μg to about 3500 μg, about 2250 μg to about 3250 μg, about 2250 μg to about 3000 μg, about 2250 μg to about 2750 μg, about 2250 μg to about 2500 μg, about 2500 μg to about 4000 μg, about 2500 μg to about 3750 μg, about 2500 μg to about 3500 μg, about 2500 μg to about 3250 μg, about 2500 μg to about 3000 μg, about 2500 μg to about 2750 μg, about 2750 μg to about 4000 μg, about 2750 μg to about 3750 μg, about 2750 μg to about 3500 μg, about 2750 μg to about 3250 μg, about 2750 μg to about 3000 μg, about 3000 μg to about 4000 μg, about 3000 μg to about 3750 μg, about 3000 μg to about 3500 μg, about 3000 μg to about 3250 μg, about 3250 μg to about 4000 μg, about 3250 μg to about 3750 μg, about 3250 μg to about 3500 μg, about 3500 μg to about 4000 μg, about 3500 μg to about 3750 μg, or about 3750 μg to about 4000 μg.

In some embodiments, the at least one active ingredient is present in about 0.1 mg/mL to about 50 mg/mL, about 0.1 mg/mL to about 25 mg/mL, about 0.1 mg/mL to about 10 mg/mL, about 1 mg/mL to about 50 mg/mL, about 1 mg/mL to about 25 mg/mL, about 1 mg/mL to about 10 mg/mL, about 0.1 mg/mL to about 5.0 mg/mL (e.g., about 0.1 mg/mL to about 4.5 mg/mL, about 0.1 mg/mL to about 4.0 mg/mL, about 0.1 mg/mL to about 3.5 mg/mL, about 0.1 mg/mL to about 3.0 mg/mL, about 0.1 mg/mL to about 2.5 mg/mL, about 0.1 mg/mL to about 2.0 mg/mL, about 0.1 mg/mL to about 1.5 mg/mL, about 0.1 mg/mL to about 1.0 mg/mL, about 0.1 mg/mL to about 0.5 mg/mL, about 0.5 mg/mL to about 4.5 mg/mL, about 0.5 mg/mL to about 4.0 mg/mL, about 0.5 mg/mL to about 3.5 mg/mL, about 0.5 mg/mL to about 3.0 mg/mL, about 0.5 mg/mL to about 2.5 mg/mL, about 0.5 mg/mL to about 2.0 mg/mL, about 0.5 mg/mL to about 1.5 mg/mL, about 0.5 mg/mL to about 1.0 mg/mL, about 1.0 mg/mL to about 4.5 mg/mL, about 1.0 mg/mL to about 4.0 mg/mL, about 1.0 mg/mL to about 3.5 mg/mL, about 1.0 mg/mL to about 3.0 mg/mL, about 1.0 mg/mL to about 2.5 mg/mL, about 1.0 mg/mL to about 2.0 mg/mL, about 1.0 mg/mL to about 1.5 mg/mL, about 1.5 mg/mL to about 4.5 mg/mL, about 1.5 mg/mL to about 4.0 mg/mL, about 1.5 mg/mL to about 3.5 mg/mL, about 1.5 mg/mL to about 3.0 mg/mL, about 1.5 mg/mL to about 2.5 mg/mL, about 1.5 mg/mL to about 2.0 mg/mL, about 2.0 mg/mL to about 4.5 mg/mL, about 2.0 mg/mL to about 4.0 mg/mL, about 2.0 mg/mL to about 3.5 mg/mL, about 2.0 mg/mL to about 3.0 mg/mL, about 2.0 mg/mL to about 2.5 mg/mL, about 2.5 mg/mL to about 4.5 mg/mL, about 2.5 mg/mL to about 4.0 mg/mL, about 2.5 mg/mL to about 3.5 mg/mL, about 2.5 mg/mL to about 3.0 mg/mL, about 3.0 mg/mL to about 4.5 mg/mL, about 3.0 mg/mL to about 4.0 mg/mL, about 3.0 mg/mL to about 3.5 mg/mL, about 3.5 mg/mL to about 4.5 mg/mL, about 3.5 mg/mL to about 4.0 mg/mL, or about 3.5 mg/mL to about 4.5 mg/mL, relative to the pharmaceutical composition).

In some embodiments, the at least one active ingredient is present in about 0.1 μg/mL to about 50 μg/mL, about 0.1 μg/mL to about 25 μg/mL, about 0.1 μg/mL to about 10 μg/mL, about 1 μg/mL to about 50 μg/mL, about 1 μg/mL to about 25 μg/mL, about 1 μg/mL to about 10 μg/mL, about 0.1 μg/mL to about 5.0 μg/mL, e.g., about 1 μg/mL to about 5 μg/mL, about 0.1 μg/mL to about 4.0 μg/mL, about 0.1 μg/mL to about 3.5 μg/mL, about 0.1 μg/mL to about 3.0 μg/mL, about 0.1 μg/mL to about 2.5 μg/mL, about 0.1 μg/mL to about 2.0 μg/mL, about 0.1 μg/mL to about 1.5 μg/mL, about 0.1 μg/mL to about 1.0 μg/mL, about 0.1 μg/mL to about 0.5 μg/mL, about 0.5 μg/mL to about 4.5 μg/mL, about 0.5 μg/mL to about 4.0 μg/mL, about 0.5 μg/mL to about 3.5 μg/mL, about 0.5 μg/mL to about 3.0 μg/mL, about 0.5 μg/mL to about 2.5 μg/mL, about 0.5 μg/mL to about 2.0 μg/mL, about 0.5 μg/mL to about 1.5 μg/mL, about 0.5 μg/mL to about 1.0 μg/mL, about 1.0 μg/mL to about 4.5 μg/mL, about 1.0 μg/mL to about 4.0 μg/mL, about 1.0 μg/mL to about 3.5 μg/mL, about 1.0 g/mL to about 3.0 μg/mL, about 1.0 μg/mL to about 2.5 μg/mL, about 1.0 μg/mL to about 2.0 μg/mL, about 1.0 μg/mL to about 1.5 μg/mL, about 1.5 μg/mL to about 4.5 μg/mL, about 1.5 μg/mL to about 4.0 μg/mL, about 1.5 μg/mL to about 3.5 μg/mL, about 1.5 μg/mL to about 3.0 μg/mL, about 1.5 μg/mL to about 2.5 μg/mL, about 1.5 μg/mL to about 2.0 μg/mL, about 2.0 μg/mL to about 4.5 μg/mL, about 2.0 μg/mL to about 4.0 μg/mL, about 2.0 μg/mL to about 3.5 μg/mL, about 2.0 μg/mL to about 3.0 μg/mL, about 2.0

μg/mL to about 2.5 μg/mL, about 2.5 μg/mL to about 4.5 μg/mL, about 2.5 μg/mL to about 4.0 μg/mL, about 2.5 μg/mL to about 3.5 μg/mL, about 2.5 μg/mL to about 3.0 μg/mL, about 3.0 μg/mL to about 4.5 μg/mL, about 3.0 μg/mL to about 4.0 μg/mL, about 3.0 μg/mL to about 3.5 μg/mL, about 3.5 μg/mL to about 4.5 μg/mL, about 3.5 μg/mL to about 4.0 μg/mL, or about 3.5 μg/mL to about 4.5 μg/mL, relative to the pharmaceutical composition.

Kits

Disclosed herein, in certain embodiments, is a kit for the treatment of urothelial, bladder, or kidney cancers in an individual in need thereof. In certain embodiments, a kit disclosed herein comprises an ETBR antagonist in an amount effective for use in a combination therapy, an immune checkpoint inhibitor, and a pharmaceutically acceptable carrier. In some embodiments, the ETBR antagonist is a specifically deuterated ETBR antagonist, e.g., deuterated BQ-788. In some embodiments, the ETBR antagonist, e.g., deuterated BQ-788, is disposed in a single container with the immune checkpoint inhibitor. In some embodiments, the ETBR antagonist, e.g., deuterated BQ-788, is disposed in a first container, and the immune checkpoint inhibitor is disposed in a second container. In some embodiments, the ETBR antagonist and the immune checkpoint inhibitor are to be administered approximately contemporaneously.

In certain embodiments, a kit disclosed herein comprises an immune checkpoint inhibitor, a synergistically effective amount of BQ-788, and a pharmaceutically acceptable carrier or excipient. In some embodiments, the BQ-788 is a deuterated BQ-788. In some embodiments, the at least one checkpoint inhibitor is an anti-PD1 antibody or an anti-PD-L1 antibody.

EXAMPLES

Example 1. Synthesis of Deuterated ETBR Antagonists

Deuterated ETBR antagonists may be prepared by deuterating known and commercial ETBR antagonists by standard methods and procedures.

Specific deuterated ETBR antagonists may be prepared by the schemes presented below. BQ-788-B (COMPOUND 1) can be prepared by the method demonstrated in FIG. 14.

Figure 14:
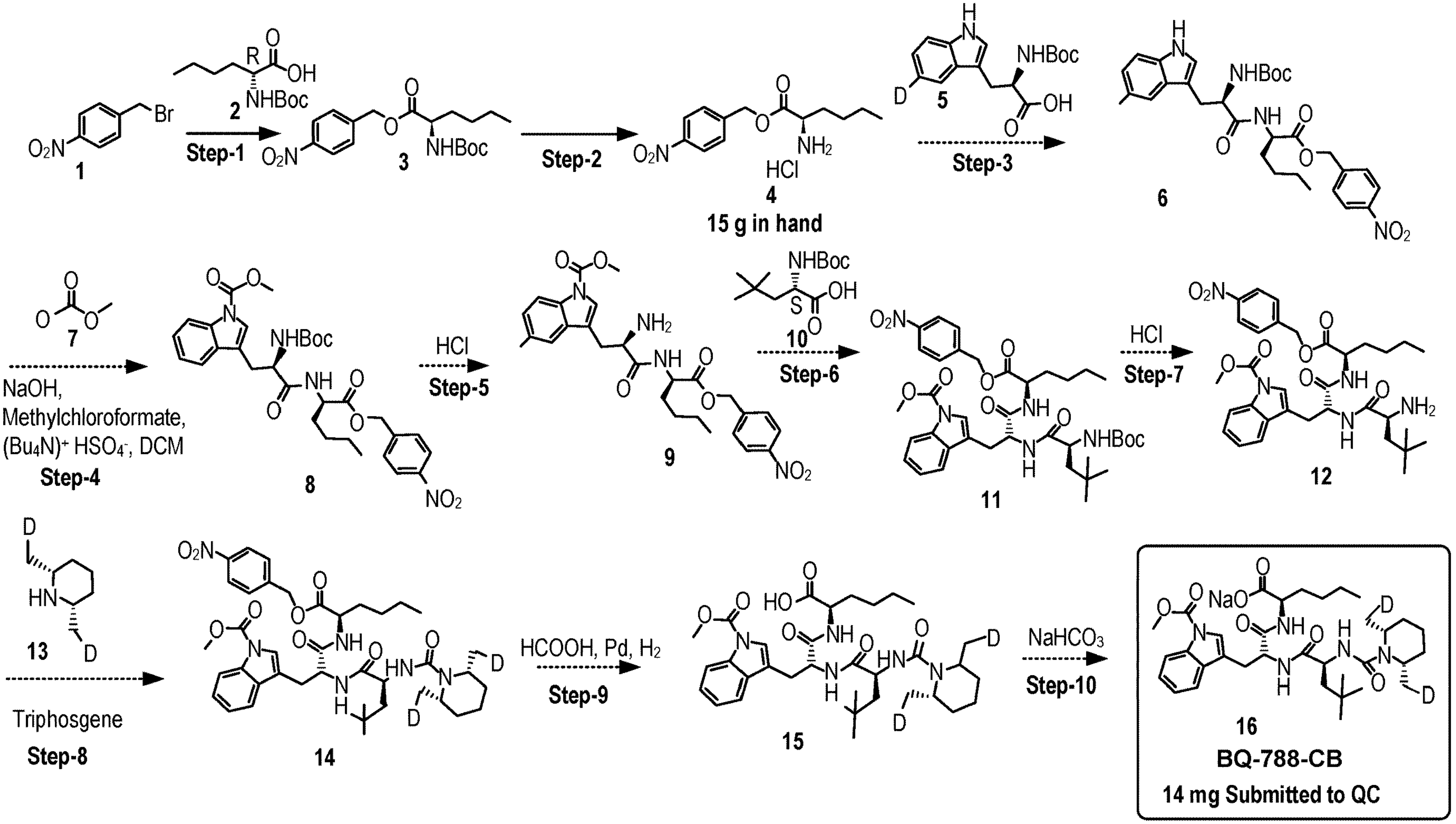
FIG. 14 depicts an exemplary synthetic scheme for preparation of specifically deuterated ETBR antagonists.
Figure 15:
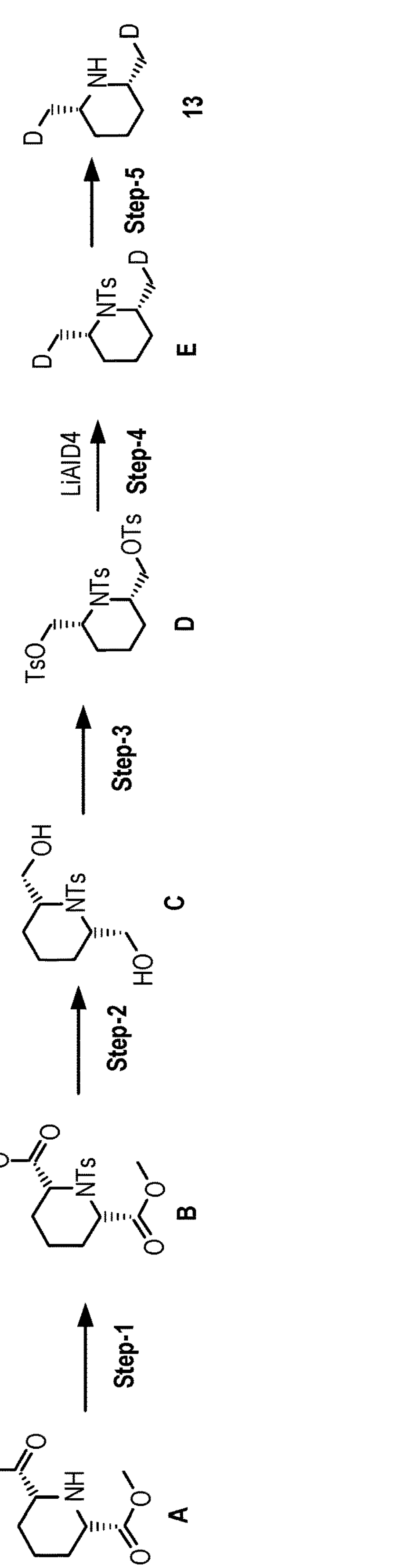
FIG. 15 depicts an exemplary synthetic scheme for preparation of intermediates for synthesis of specifically deuterated ETBR antagonists.

Intermediate 13 of FIG. 14 can be prepared by the following scheme 2 depicted in FIG. 15 (Intermediate 13):

A non-deuterated analog of Intermediate 13 can be prepared by substituting $LiAlH_4$ in place of $LiAlD_4$ in Step 4.

Figure 16:
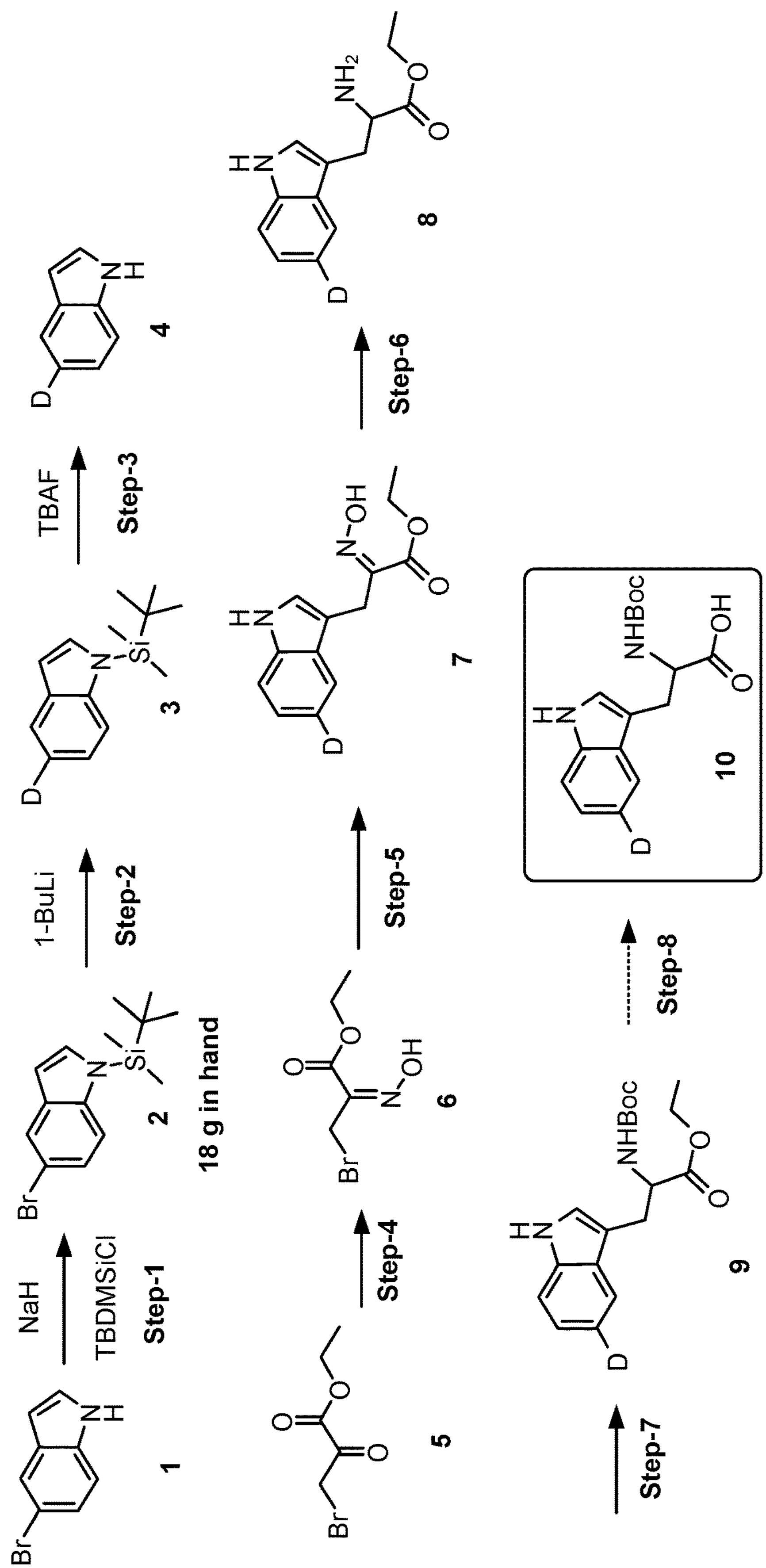
FIG. 16 depicts an exemplary synthetic scheme for preparation of intermediates for synthesis of the specifically deuterated ETBR antagonists BQ-788-A and BQ-788-C.

BQ-788-A and BQ-788-C can be prepared by substituting a deuterated analog of Intermediate 5 in Step 3 of scheme 1. Such an analog can be prepared by the method demonstrated in FIG. 16 (Intermediate 5d) below:

Compound 10 from Scheme 3 is then used in place of Compound 5 in scheme 1. For BQ-788-C Scheme 1 is then followed to completion. For BQ-788-A, the non-deuterated analog of Intermediate 13 of Scheme 1 is used Intermediate 4 of Scheme 3 can be prepared by reacting a bromonated indole with NaBD4 in the presence of a palladium catalyst.

Figure 17:
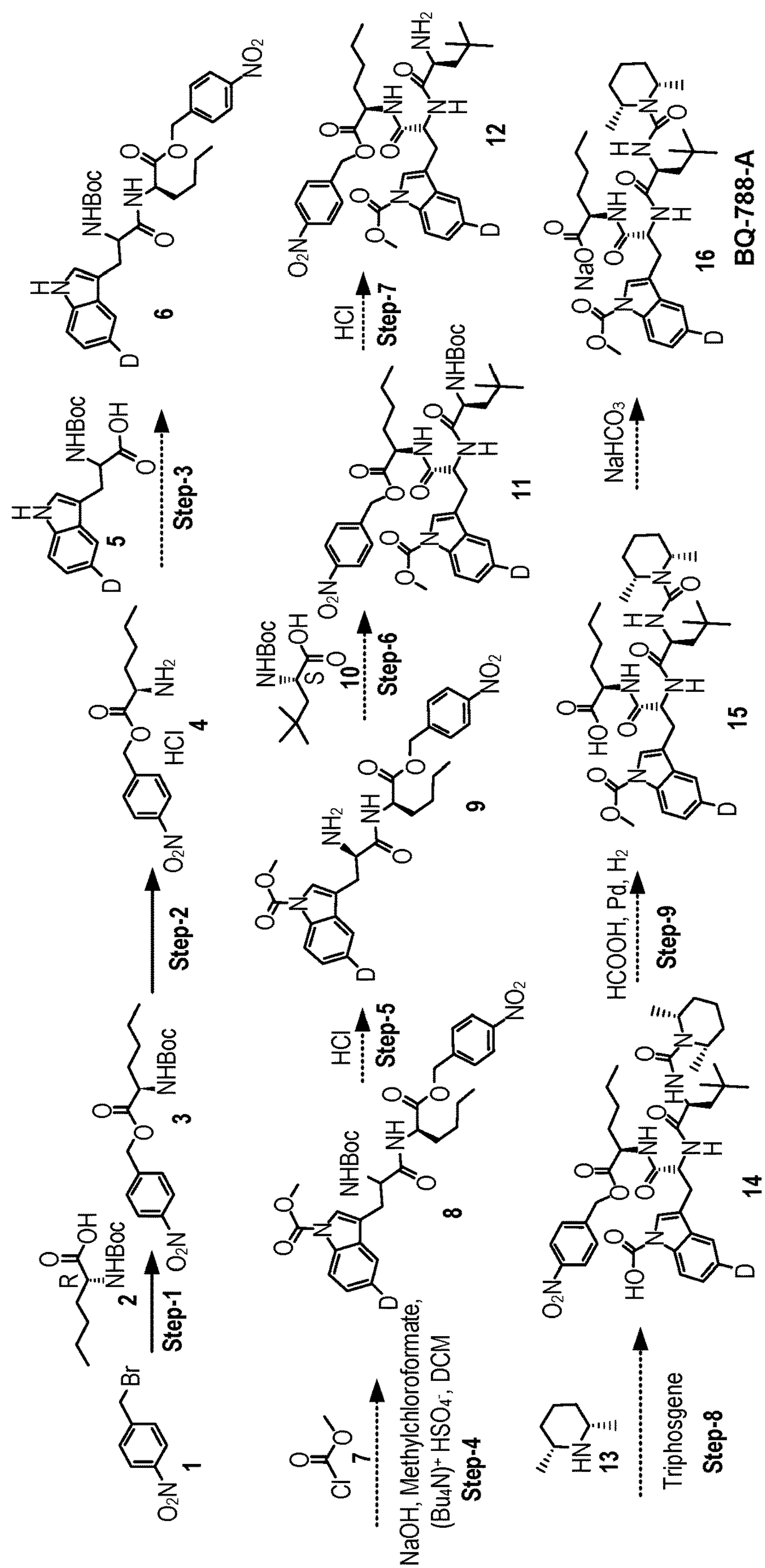
FIG. 17 depicts an exemplary synthetic scheme for preparation of the specifically deuterated ETBR antagonist BQ-788-A.

In an exemplary embodiment, compound BQ-788-A is prepared by the method demonstrated in FIG. 17.

Figure 18:
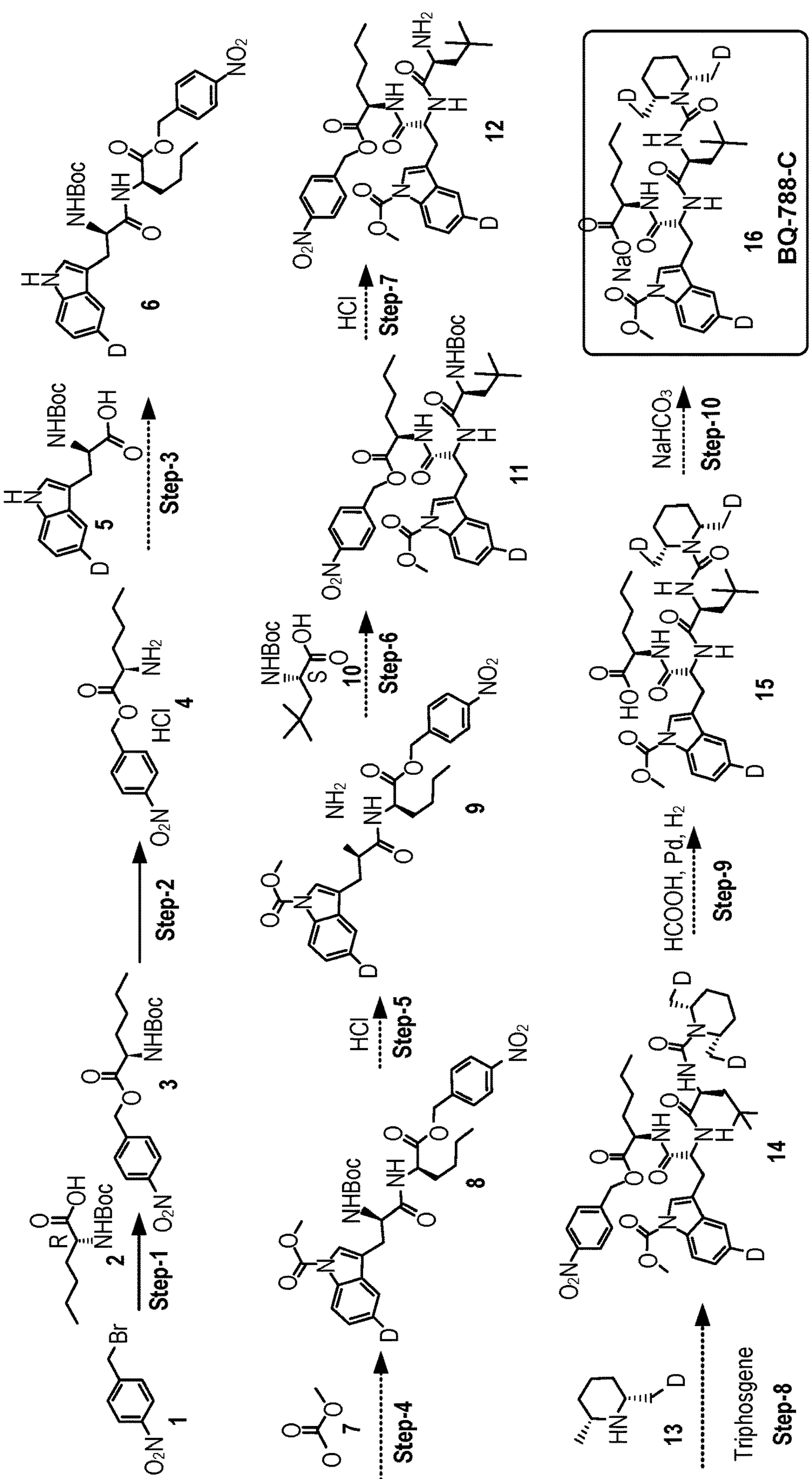
FIG. 18 depicts an exemplary synthetic scheme for preparation of the specifically deuterated ETBR antagonist BQ-788-C.

In addition, compound BQ-788-C can be prepared according to the method demonstrated in FIG. 18.

The number and position of the deuterium atoms is not to be limited by the specific schemes or examples shown herein. The preparation of compounds with more deuterium substitution can be readily extrapolated from the schemes presented here using commonly known starting materials or prepared using standard synthetic methods.

Example 2. Biological Activities of Deuterated ETBR Antagonists

Figure 4A:
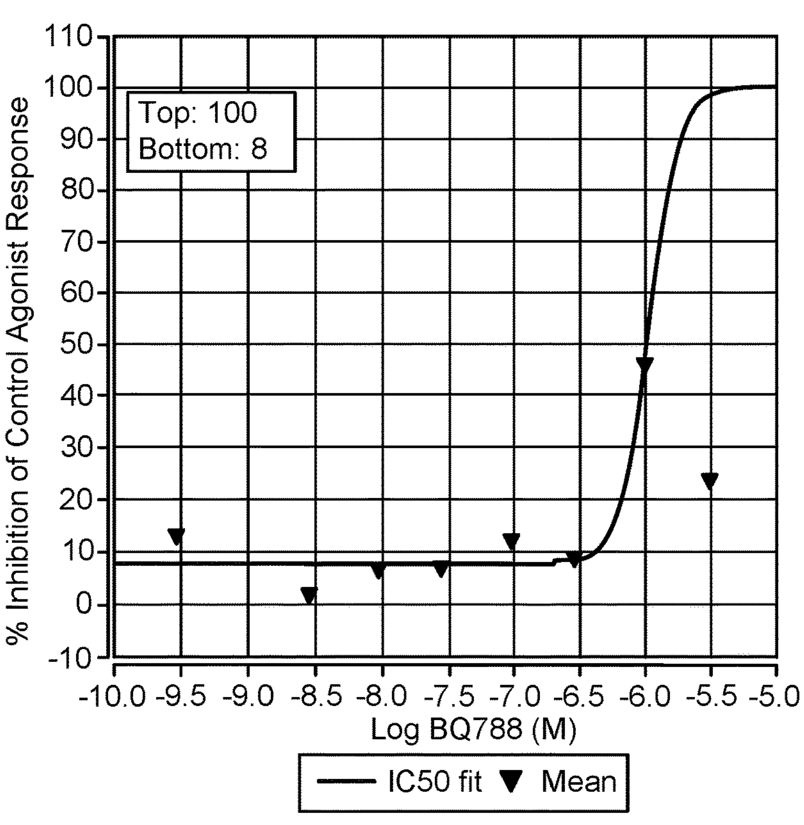
FIGS. 4A and 4B illustrates human ("h") CXCR inhibitory effects for, A) BQ-788 and B) BQ-788-B (Compound 1), a specifically deuterated ETBR antagonist. Cellular agonist effect was calculated as a % of control response to a known reference agonist for CXCR4 (h), and cellular antagonist effect was calculated as a % inhibition of control reference agonist response for CXCR4. Results showing ≥50% inhibition of agonist effect are considered significant while those showing less than 25% inhibition are not considered significant. The IC50 for BQ-788 was greater than about 1.0E-6 M. The IC50 for BQ-788-B (Compound 1) was not calculable.
Figure 4B:
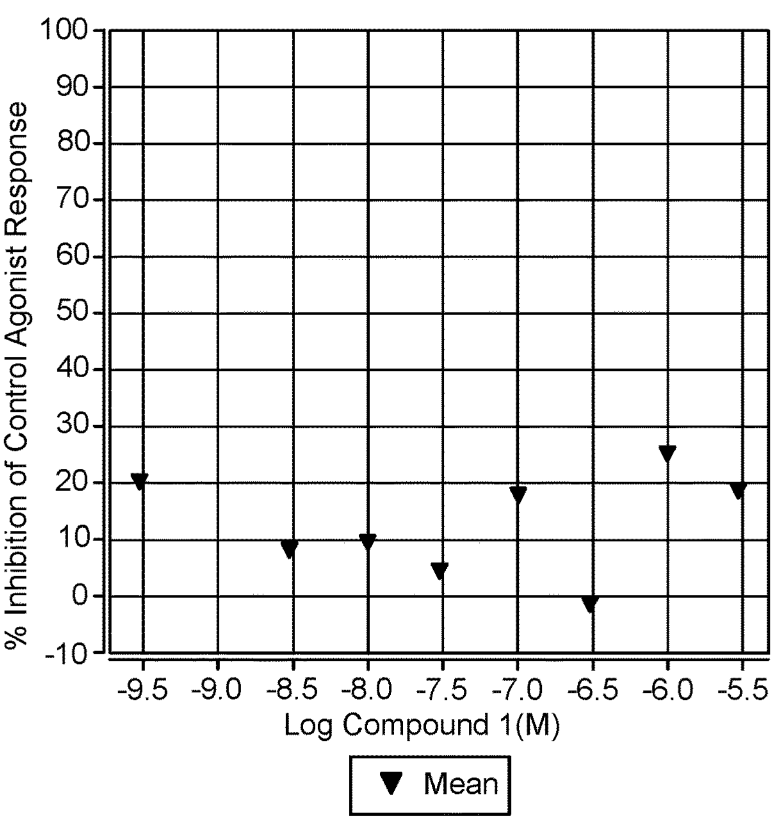

Determination of CXCR4 inhibitory effect. The inhibitory effect on CXCR4 (h) was determined for BQ-788 (FIG. 4A), and BQ-788-B (COMPOUND 1) (FIG. 4B). Cellular agonist effect was calculated as a % of control response to a known reference agonist for CXCR4 (h), and cellular antagonist effect was calculated as a % inhibition of control reference agonist response for CXCR4. Recombinant human CXCR4 was expressed in CHO cells, and stimulated with 1 nM SDF-1α and incubated at 28° C. Dielectric spectroscopy was used to measure impedance of the cells. Results showing ≥50% inhibition of agonist effect are considered significant while those showing less than 25% inhibition are not considered significant. The IC50 for BQ-788 was greater than about 1.0E-6 M. The IC50 for BQ-788-B (COMPOUND 1) was not calculable.

Figure 5A:
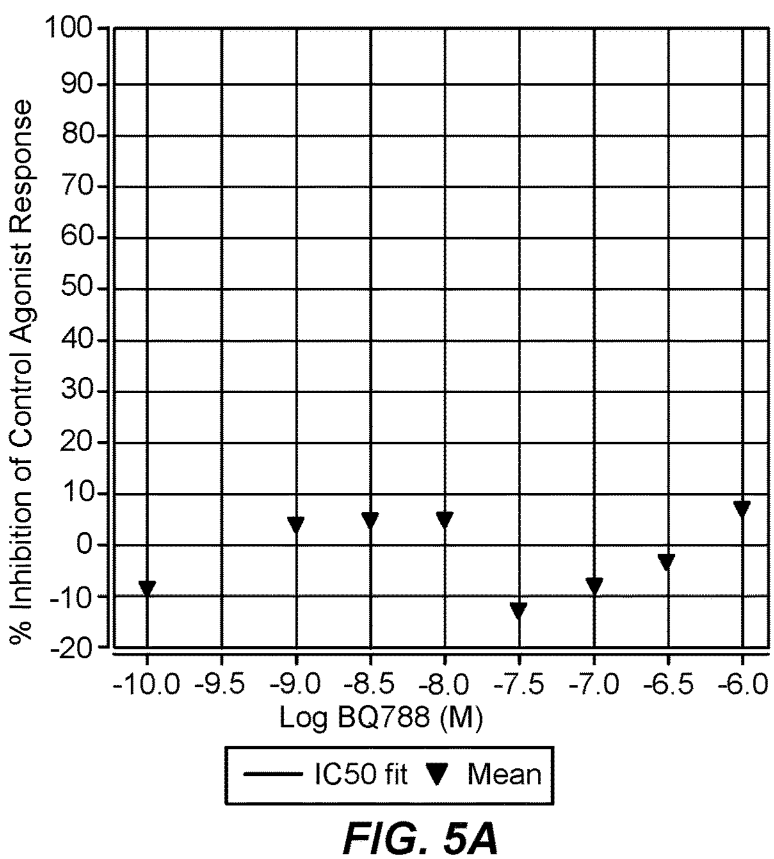
FIGS. 5A and 5B illustrate human ("h") Endothelin receptor type A ("ETA") inhibitory effect for A) BQ-788 and B) BQ-788-B (Compound 1), a specifically deuterated ETBR antagonist. Cellular agonist effect was calculated as a % of control response to a known reference agonist for ETA (h), and cellular antagonist effect was calculated as a % inhibition of control reference agonist response for ETA. Results showing ≥50% inhibition of agonist effect are considered significant while those showing less than 25% inhibition are not considered significant. The IC50 for BQ-788 and BQ-788-B (Compound 1) was not calculable (i.e., the dose-response curve shows less than 25% effect at the highest validated testing concentration).
Figure 5B:
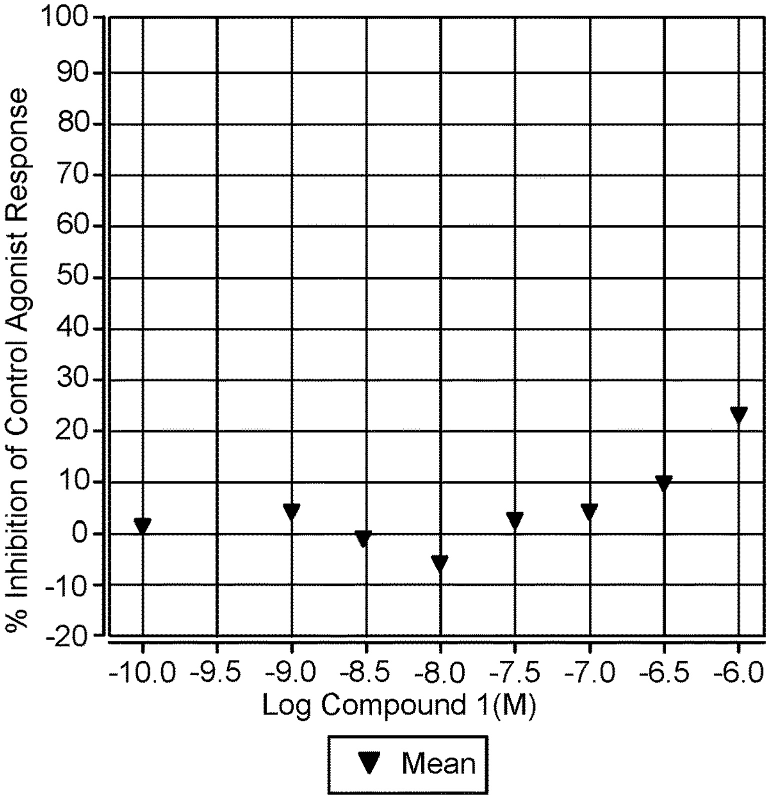

Determination of ETA (h) inhibitory effect for BQ-788 and BQ-788-B (COMPOUND 1). FIGS. 5A and 5B demonstrate the determination of ETA (h) inhibitory effect for, A) BQ-788 and B) BQ-788-B (i.e., "Compound 1"). Cellular agonist effect was calculated as a % of control response to a known reference agonist for ETA (h), and cellular antagonist effect was calculated as a % inhibition of control reference agonist response for ETA. Results showing ≥50% inhibition of agonist effect are considered significant while those showing less than 25% inhibition are not considered significant. The IC50 for BQ-788 and BQ-788-B (COMPOUND 1) was not calculable (i.e., the dose-response curve shows less than 25% effect at the highest validated testing concentration).

Figure 6:
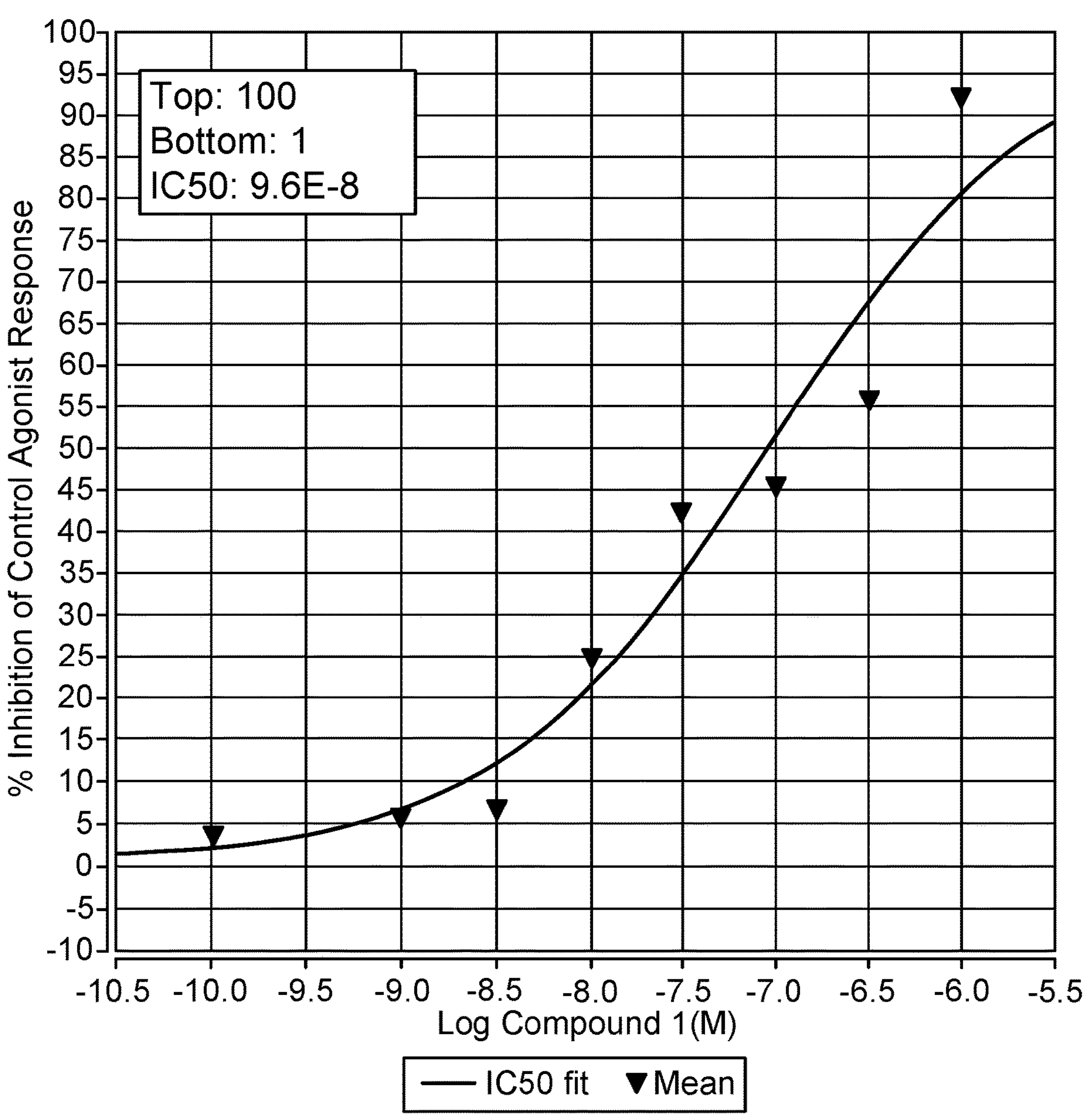
FIG. 6 illustrates the inhibition of melanoma growth and metastasis and induction of apoptosis in melanoma tumor cells following contact with specifically deuterated ETBR antagonists. Cellular agonist effect was calculated as a % of control response to a known reference agonist for human ("h") Endothelin receptor type B ("ETB"), and cellular antagonist effect was calculated as a % inhibition of control reference agonist response for ETB. Results showing ≥50% inhibition of agonist effect are considered significant while those showing less than 25% inhibition are not considered significant. The IC50 for BQ-788 was 5.1E-08 M and the Kd was 1.3E-08; while the IC50 for the specifically deuterated compound is 9.6E-08 M and a Kd of 2.5E-08.

Determination of ETBR inhibitory effect for specifically deuterated ETBR antagonists. FIG. 6 demonstrates that specifically deuterated ETBR antagonists inhibit melanoma growth and metastasis and induce apoptosis in melanoma tumor cells. Cellular agonist effect was calculated as a % of control response to a known reference agonist for ETB (h), and cellular antagonist effect was calculated as a % inhibition of control reference agonist response for ETB. Results showing ≥50% inhibition of agonist effect are considered significant while those showing less than 25% inhibition are not considered significant. The IC50 for a non-deuterated ETBR antagonist was 5.1E08 M and the Kd was 1.3E-08; while the IC50 for specifically deuterated ETBR antagonists were 9.6E-08 M and a Kd of 2.5E-08. Surprisingly, in PK studies in vivo, the specifically deuterated ETBR antagonists demonstrated enhanced biologic activity relative to the non-deuterated counterpart.

Figure 7:
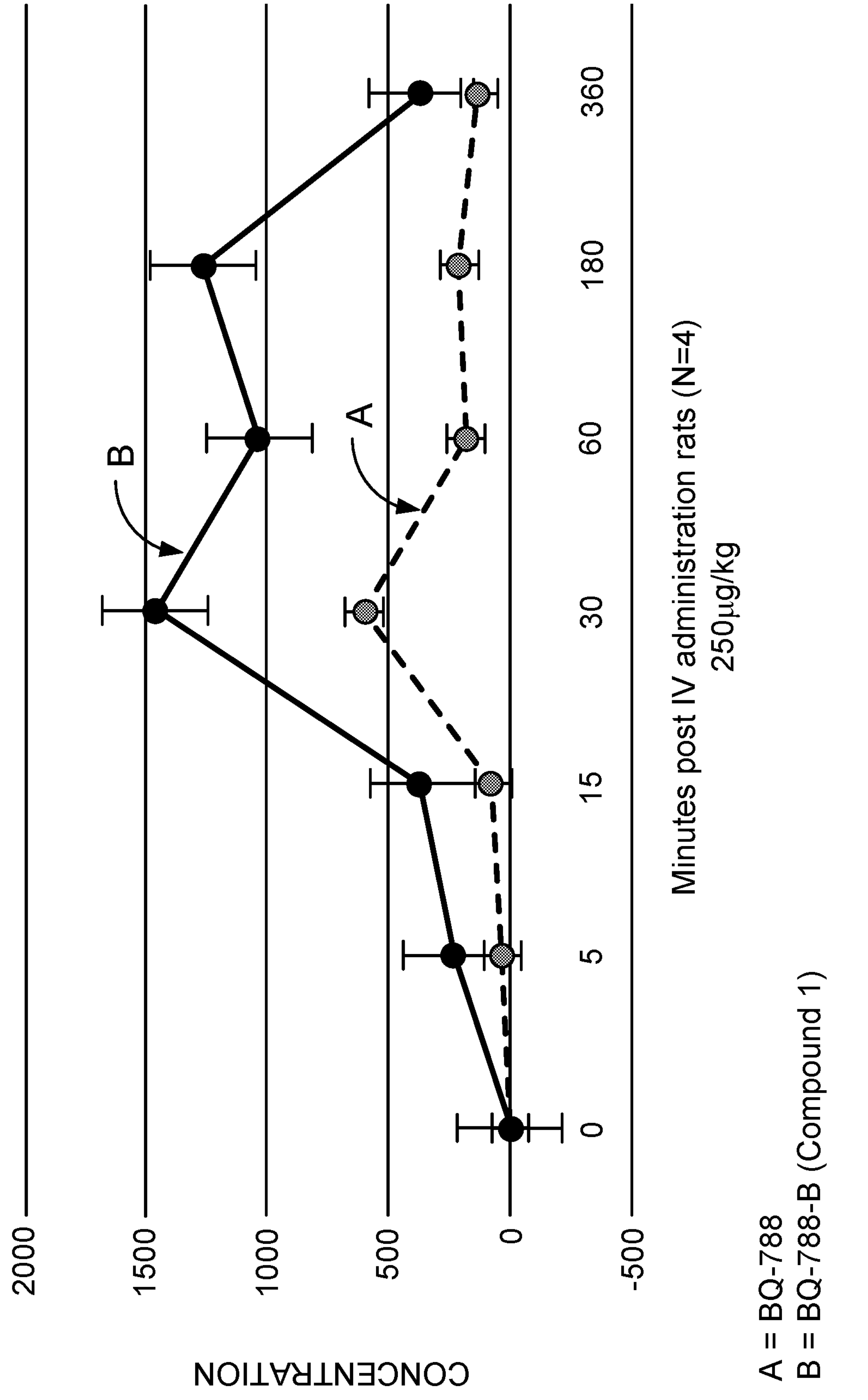
FIG. 7 shows that BQ-788-B (Compound 1), a specifically deuterated ETBR antagonist demonstrates enhanced plasma ET-1 concentration relative to BQ-788. BQ-788-B (Compound 1) demonstrates a prolonged peak out to about 3 hours as compared to BQ-788, which demonstrates a transient peak at about 30 minutes. The IC50 for BQ-788-B (Compound 1) is 9.6E-08 M (MW=665.37). The IC50 for BQ-788 is 5.6E-08 (MW=663.78).

Plasma concentrations of BQ-788 versus BQ-788-B (COMPOUND 1). FIG. 7 illustrates that BQ-788-B (COMPOUND 1) (curve "B"), a deuterated analog of BQ-788, demonstrates enhanced plasma concentrations relative to BQ-788. Briefly, rats (N=4 animals per timepoint) were administered either BQ-788 or the deuterated form, BQ-788-B (COMPOUND 1) at a dose of 250 μg/kg via IV infusion. Plasma samples were collected at various time points and ET-1 ELISA performed. BQ788 and BQ788-B are peptide drugs that are rapidly degraded in plasma and thus drug levels are difficult to detect directly. However, when BQ788 binds ETBR, this results in an increase in plasma concentrations of ET-1, the ligand for ETBR. As such, plasma levels of ET-1 are commonly used as an indirect measure of BQ-788 biologic activity. Significantly, the deuterated compound BQ-788-B (COMPOUND 1) demonstrates an enhanced duration and amplitude of response relative to the undeuterated form as exemplified by the prolonged peak out to about 3 hours as compared to BQ-788, which demonstrates a transient peak at about 30 minutes. The IC50 for BQ-788-B (COMPOUND 1) is 9.6E-08 M (MW=665.37). The IC50 for BQ-788 is 5.6E-08 (MW=663.78).

BQ-788-B (Compound 1) in combination with anti-PD1 demonstrates synergistic results. Dual combination of specifically deuterated compounds and immunotherapeutics (FIG. 8), result in superior efficacy relative combinations with approved cancer drugs. The syngeneic melanoma model V600E+ (BRAF mutated) SM1 tumor model was used in C57BL/6 mice to assess efficacy of deuterated ETBR antagonists in combination with immunotherapeutics ("B+P") as compared to a standard treatment, dabrafenib with anti-PD1 ("D+P"). Previous studies have indicated that V600E+ model demonstrates no efficacy for anti-PD1 as a single agent (and little tumor infiltrating lymphocytes (TILs)). In this study 6-8 week old female C57BL/6 mice were inoculated with SM1 tumor fragments (TME* components present). Dosing was initiated when tumors were 150 mm3. The general dosing schemes were as follows: dabrafenib (30 mg/kg daily by oral gavage), immunotherapeutic 10 mg/kg Q4D IP beginning 2 days after dabrafenib), deuterated ETBR antagonist (4 μg administered QOD IV beginning 2 days after dabrafenib). Tumors were measured three times per week, and the study was terminated after 21 days of dosing and IHC analysis of tumors was performed. The dual combination of the immunotherapeutic and the deuterated ETBR antagonist induced tumor shrinkage below baseline. In stark contrast, a standard combination of dabrafenib and the immunotherapeutic failed to shrink tumors but demonstrated intermediate tumor growth inhibition. IHC analysis of tumors treated with immunotherapeutics and deuterated ETBR antagonists revealed that tumors had been eradicated leaving only residual adipose tissue. In sum, the combination of immunotherapeutic compounds with specifically deuterated ETBR antagonists as described herein provided significant improvement against tumor growth relative to the existing therapeutic paradigm.

Figure 8:
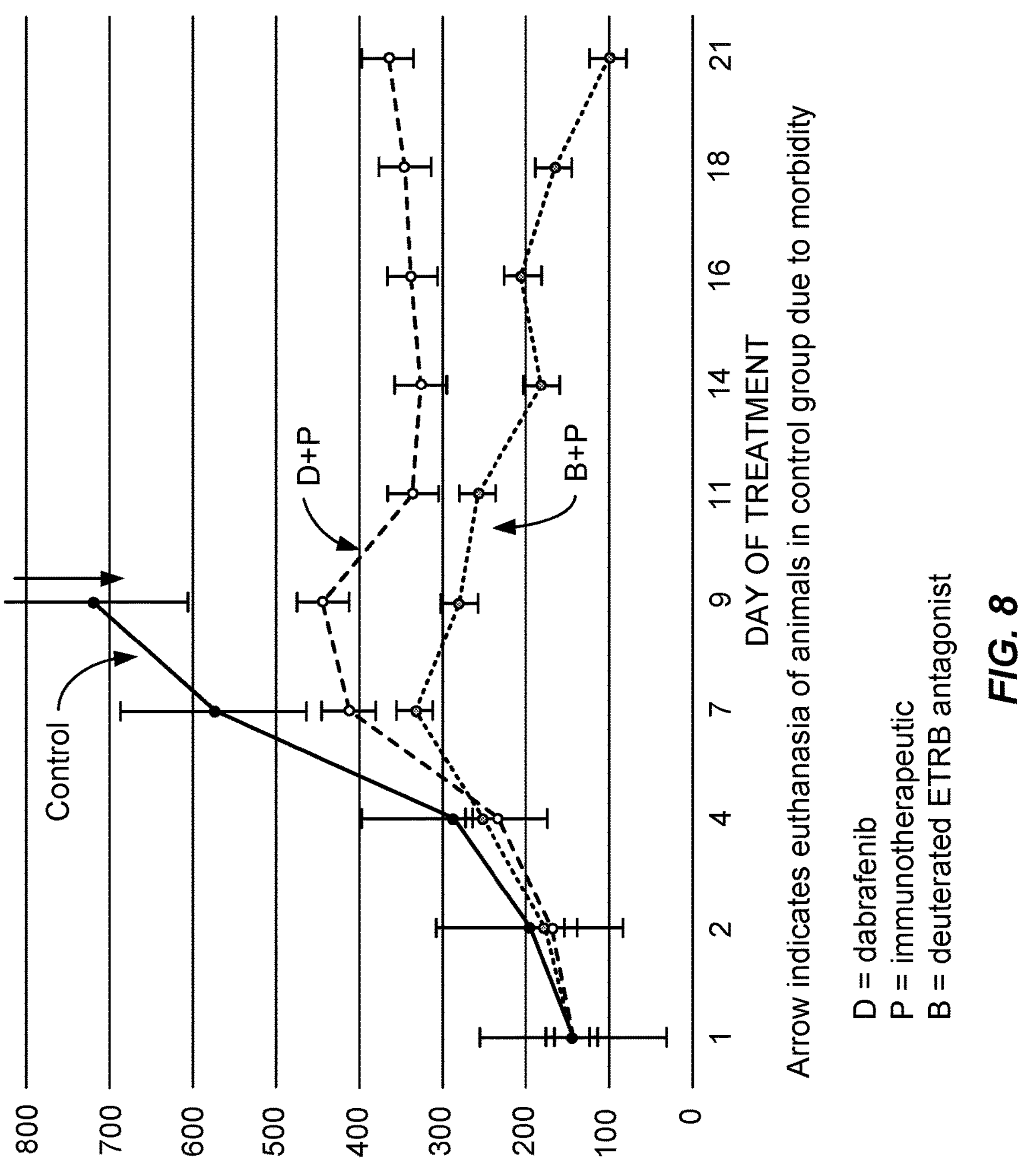
FIG. 8 illustrates superior efficacy from a dual combination of specifically deuterated ETBR antagonists and an immunotherapeutic relative to current standard drug combinations. The syngeneic melanoma model V600E+ (BRAF mutated) SM1 tumor model was used in C57BL/6 mice to assess efficacy of the specific deuterated ETBR antagonist in combination with the immunotherapeutic ("B+P") as compared to a standard of treatment, dabrafenib with anti-PD1 ("D+P").
Figure 9A:
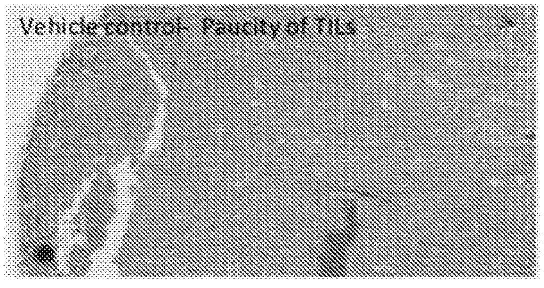
FIGS. 9A-9E illustrates tumor eradication from a dual combination of the specifically deuterated ETBR antagonist BQ-788-B (Compound 1) and immune checkpoint inhibitors (e.g. anti-PD1).
Figure 9B:
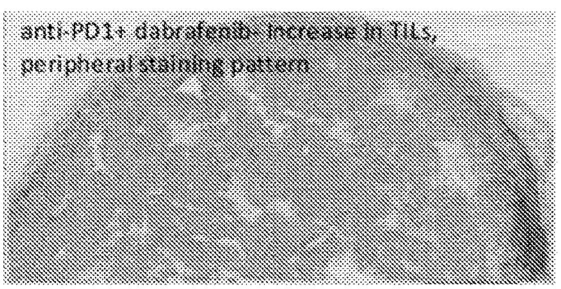
Figure 9C:
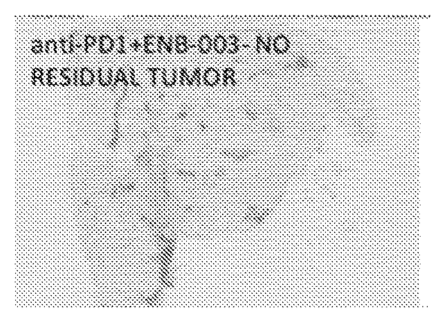
Figure 9D:
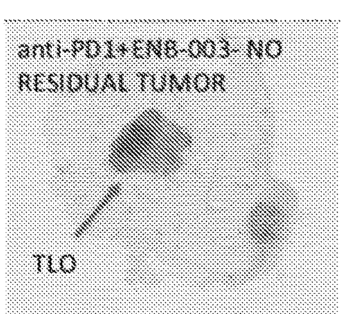
Figure 9E:
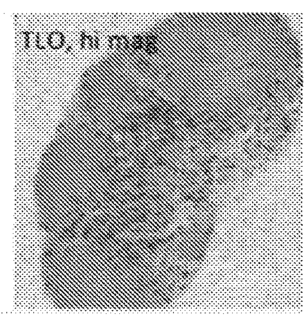

Dual combination BQ-788-B (Compound 1) and immunocheckpoint inhibitors eradicates tumors. FIGS. 9A-9E demonstrate the results of histological examination of V600E+ melanoma tumor cells implanted into C57BL/6 mice 21 days after treatment as indicated in FIG. 8. The specifically deuterated compound BQ-788-B (COMPOUND 1) and immunocheckpoint inhibitors (e.g. anti-PD1, anti-PD1, anti-CTLA) combination therapy eradicated the tumors in 21 days, promoted robust infiltration by CD8+ lymphocytes (TILs), and tertiary lymphoid organ (TLO) formation. FIG. 9A shows images of the control treated tumor cells. FIG. 9B shows images of the tumor cells treated with anti-PD1 and dabrafenib. FIG. 9C shows images of the tumor cells treated with anti-PD1 and BQ-788-B (ENB-003). FIG. 9D shows images of the tumor cells treated with anti-PD1 and BQ-788-B (ENB-003). FIG. 9E shows a high magnification image of the TLO formation of FIG. 9D. TIL infiltration is exemplified by the dark punctate staining. TLOs are functionally equivalent to lymph nodes, produce tumor-specific T- and B-cells, and induce long lasting anti-tumor immunity.

Intratumoral TLO formation induced by combination therapy including anti-PD1 and BQ-788-B (Compound 1). FIG. 10 demonstrates the histological examination of V600E+ melanoma tumor cells implanted into C57BL/6 mice 21 days after treatment as indicated in FIG. 8 with BQ-788-B (COMPOUND 1) and anti-PD1 combination therapy. The staining of CD8+, CD4+ and Treg (FoxP3) lymphocytes (dark punctate staining) indicates that the combination therapy promotes strong mobilization of lymphocytes to the tumor, which is associated with tumor eradication and positive patient outcomes.

Figure 12:
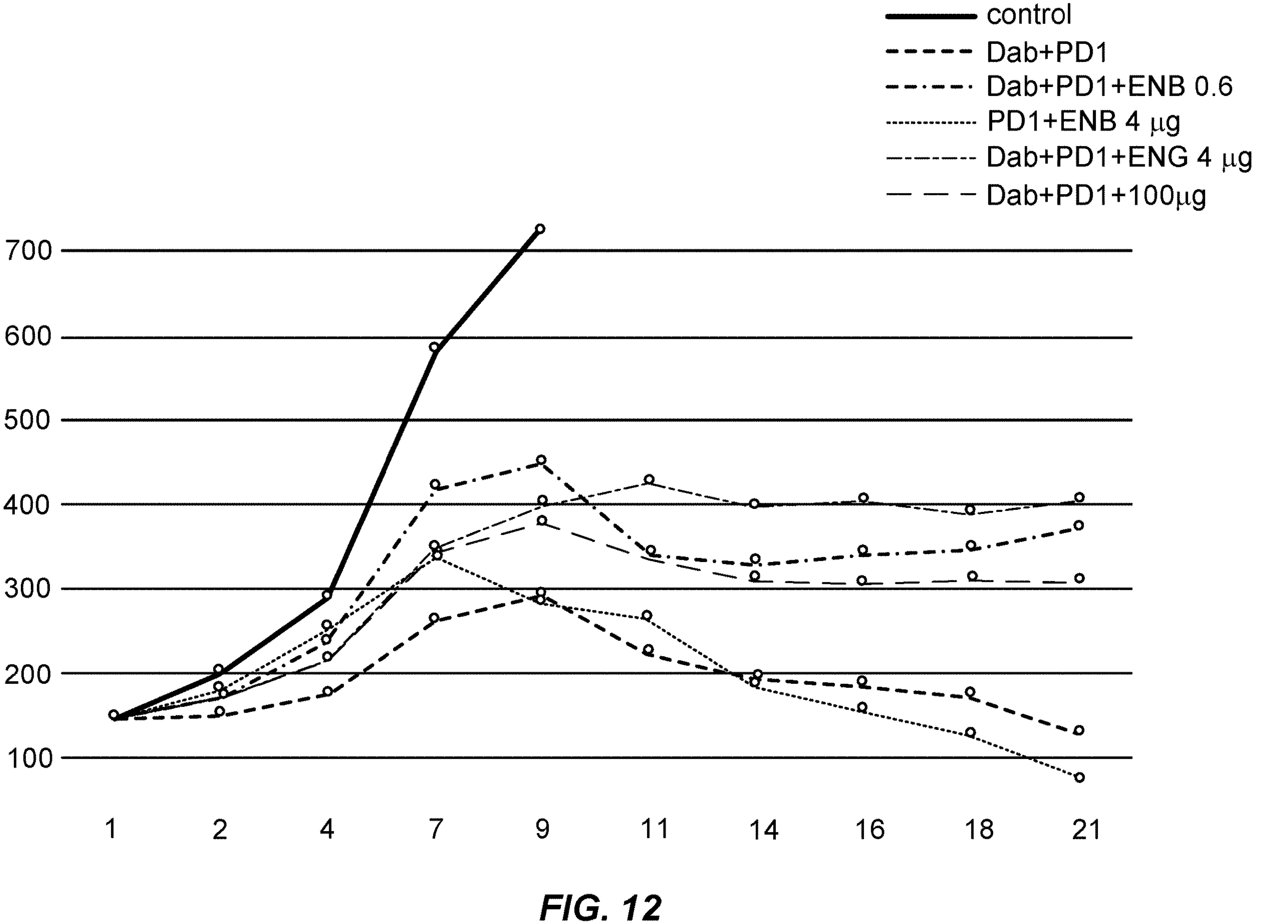
FIG. 12 illustrates how the combination of the specifically deuterated ETBR antagonist BQ-788-B (referred to as "ENB" in the figure) with the immune checkpoint inhibitor, an anti-PD1 antibody (referred to as "PD1" in the figure), restores sensitivity to the anti-PD1 antibody. The addition of dabrafenib to anti-PD1/BQ-788-B combination impairs efficacy, possibly due to dabrafenib's ability to increase Tregs and tumor-associated macrophages (TAMs).

Intratumoral (internal) TLO formation associated with treatment with BQ-788-B (ENB). FIG. 11 provides table summaries of the results obtained with combination therapies (two- and three-part), TLO formation and efficacy for tumor eradication. The model system tested is as described for FIG. 8. The combinations included dabrafenib+anti-PD1 ("D+P"); dabrafenib+anti-PD1+BQ-788-B (COMPOUND 1) at 0.6 μg ("D+P+B (0.6 μg)"); dabrafenib+anti-PD1+BQ-788-B (COMPOUND 1) at 4.0 μg ("D+P+B (4.0 μg)"); dabrafenib+anti-PD1+BQ-788-B (COMPOUND 1) at 100 μg ("D+P+B (100 μg)"); and anti-PD1+BQ-788-B (COMPOUND 1) at (4.0 μg) ("P+B (4.0 μg)"). The data indicate that (i) internal TLO formation is associated with tumor eradication; and (ii) the combination of anti-PD1 antibody and BQ-788-B (COMPOUND 1) was most frequently associated with intratumoral TLO formation and tumor reduction. FIG. 12 presents the efficacy results as a function of tumor volume (mm3). The inclusion of BQ-788-B (ENB) with anti-PD1 is synergistic and appears to help restore sensitivity to anti-PD1. The addition of dabrafenib to anti-PD1/BQ-788-B (ENB) combination impairs efficacy, possibly due to dabrafenib's ability to increase Tregs and tumor-associated macrophages (TAMs).

BQ-788-B (Compound 1) at 0.6 μg in combination with immunocheckpoint inhibitors and dabrafenib promotes diffuse CD8+ TIL staining. FIG. 13 shows demonstrates the histological examination of V600E+ melanoma tumor cells implanted into C57BL/6 mice 21 days after treatment as indicated in FIG. 8 with the respective combination therapy. The diffuse distribution of CD8+ TIL staining (dark punctate staining) appears to be associated with higher efficacy as compared to those with peripheral distribution of TILs.

Thus, specifically deuterated forms of BQ-788 as described herein, e.g., BQ-788-A BQ-788-B (Compound 1), BQ-788-C and others described herein, demonstrate synergistic activity with anti-oncologic agents in a preclinical melanoma model in which anti-PD1 lacks any efficacy as a single agent. Tumor reduction or eradication correlates well with intratumoral TLO formation or neogenesis, and diffuse infiltration pattern of TILs rather than tumor-peripheral TIL distribution. TLO neogenesis has prognostic implications and correlates will with increased patient survival. The dual combination of specifically deuterated ETBR antagonists and anti-oncologic agents is superior to other dual and triple combinations in terms of (i) anti-tumor efficacy; (ii) low anticipated toxicity (based upon established safety profile of parent compound in humans); and (iii) overall treatment cost (relative to triple therapies). In addition, IV administration allows for a 2-3 order of magnitude dose reduction relative to IP or PO administration (e.g. typical doses of 200-600 μg BQ788 vs. 0.6-4.0 μg deuterated BQ-788).

Example 3: Syngeneic Bladder Cancer Model Shows Synergy Between Anti-PD1 and BQ-788-B (Compound 1)

6 week old female C57BL/6 mice, n=5 per group, were implanted with bladder cancer tumor cells, MB49-PDIRA-220 at the right flank. When tumors reached from about 50 $mm^3$-75 $mm^3$ in volume, mice were separated into 4 treatment groups: (1) dosed with 4 μg of BQ-788-B (Compound 1) intravenously on days 1, 3, 5, 8, 10, 12 and 15 and with 100 μg of an anti-PD-1 agent intraperitoneally on days 1, 4, 9 and 13; (2) dosed with 4 μg of BQ-788-B (Compound 1) intravenously on days 1, 3, 5, 8, 10, 12 and 15; (3) dosed with 100 μg of an anti-PD-1 agent intraperitoneally on days 1, 4, 9 and 13; or (4) untreated control. Tumor volume measurements were taken every two days post treatment.

Figure 19:
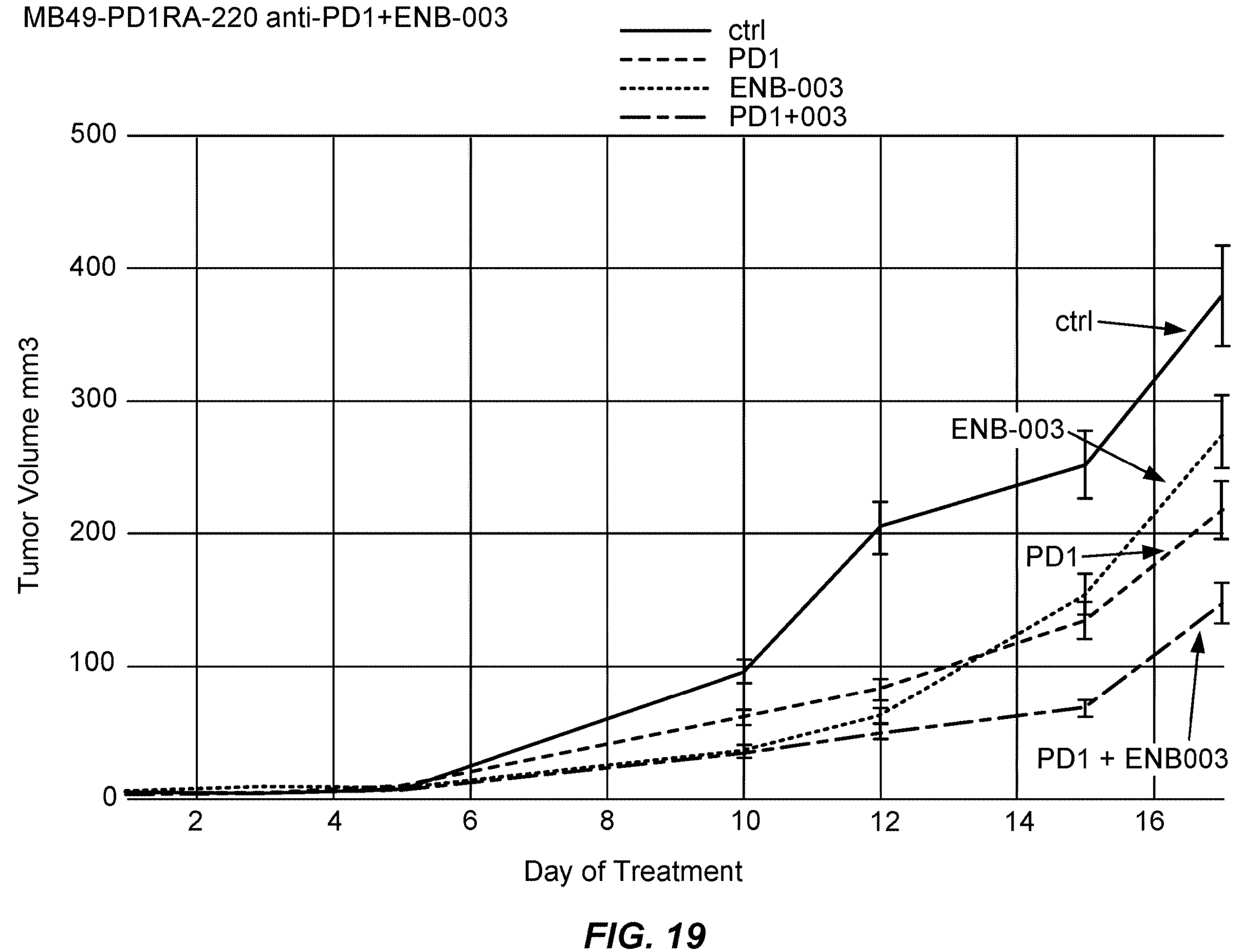
FIG. 19 illustrates tumor volume measurements of a syngeneic bladder cancer murine model plotted against days of treatment. Tumor bearing mice were treated with BQ-788-B (Compound 1) and an anti-PD-1 agent, BQ-788-B (Compound 1) alone, an anti-PD-1 agent alone, or untreated.

Tumor volume measurements were taken every two days post treatment and show that as compared to control and BQ-788-B (Compound 1) alone or anti-PD-1 alone, the combination treatment of anti-PD-1 and BQ-788-B (Compound 1) yields the greatest anti-bladder cancer treatment efficacy, FIG. 19. The syngeneic bladder cancer murine model shows synergy between anti-PD1 and BQ-788-B ("ENB-003") treatment.

Example 4: Intratumoral TLO Formation Induced by Combination Therapy Including ETBR Antagonists and Immune Checkpoint Inhibitors 6 week old female C57BL/6 mice, n=5 per group, were implanted with V600E+ melanoma cancer tumor cells. Once tumors were established, mice were dosed with ETBR antagonists and immune checkpoint inhibitors combination therapy. 21 days post treatment, histological examination was performed, FIG. 20. Staining of CD8+, CD4+ and Treg (FoxP3) lymphocytes (dark punctate staining) indicates that the combination therapy promotes strong mobilization of lymphocytes to the tumor, which is associated with tumor eradication and positive patient outcomes. Results show that infiltration of T cells into the tumor (TILs).

The data indicated that (i) internal TLO formation is associated with tumor eradication; and (ii) the combination of immune checkpoint inhibitors and ETBR antagonists is associated with intratumoral TLO formation and tumor reduction. The inclusion of ETBR antagonists with immune checkpoint inhibitors is synergistic and appears to help restore sensitivity to immune checkpoint inhibitors. The addition of dabrafenib to anti-PD1/ETBR antagonist combination impairs efficacy, possibly due to dabrafenib's ability to increase Tregs and tumor-associated macrophages (TAMs). Intratumoral TLO formation is associated with treatment with ETBR antagonists

Example 5: Syngeneic Bladder Cancer Model Shows Synergy Between Immunotherapy and BQ-788-B (Compound 1)

6 week old female C57BL/6 mice, n=5 per group, were implanted with bladder cancer tumor cells, MB49-PD1RA-220 at the right flank. When tumors reached from about 100 $mm^3$ in volume, mice were separated into 4 treatment groups: (1) dosed with BQ-788-B (Compound 1) intravenously on days 1, 3, 5, and 8 with 100 μg of an immunotherapeutic agent, namely an anti-PD-1 antibody intraperitoneally on days 1, 4, 9 and 13 (2) dosed with 4 μg of BQ-788-B (Compound 1) intravenously on days 1, 3, 5, and 8 (3) dosed with 100 μg of an anti-PD-1 agent intraperitoneally on days 1, 4, 9 and 13 or (4) untreated control. Tumor volume measurements were taken 3 times per week. The study was terminated on day 8 due to morbidity of control groups.

Figure 21:
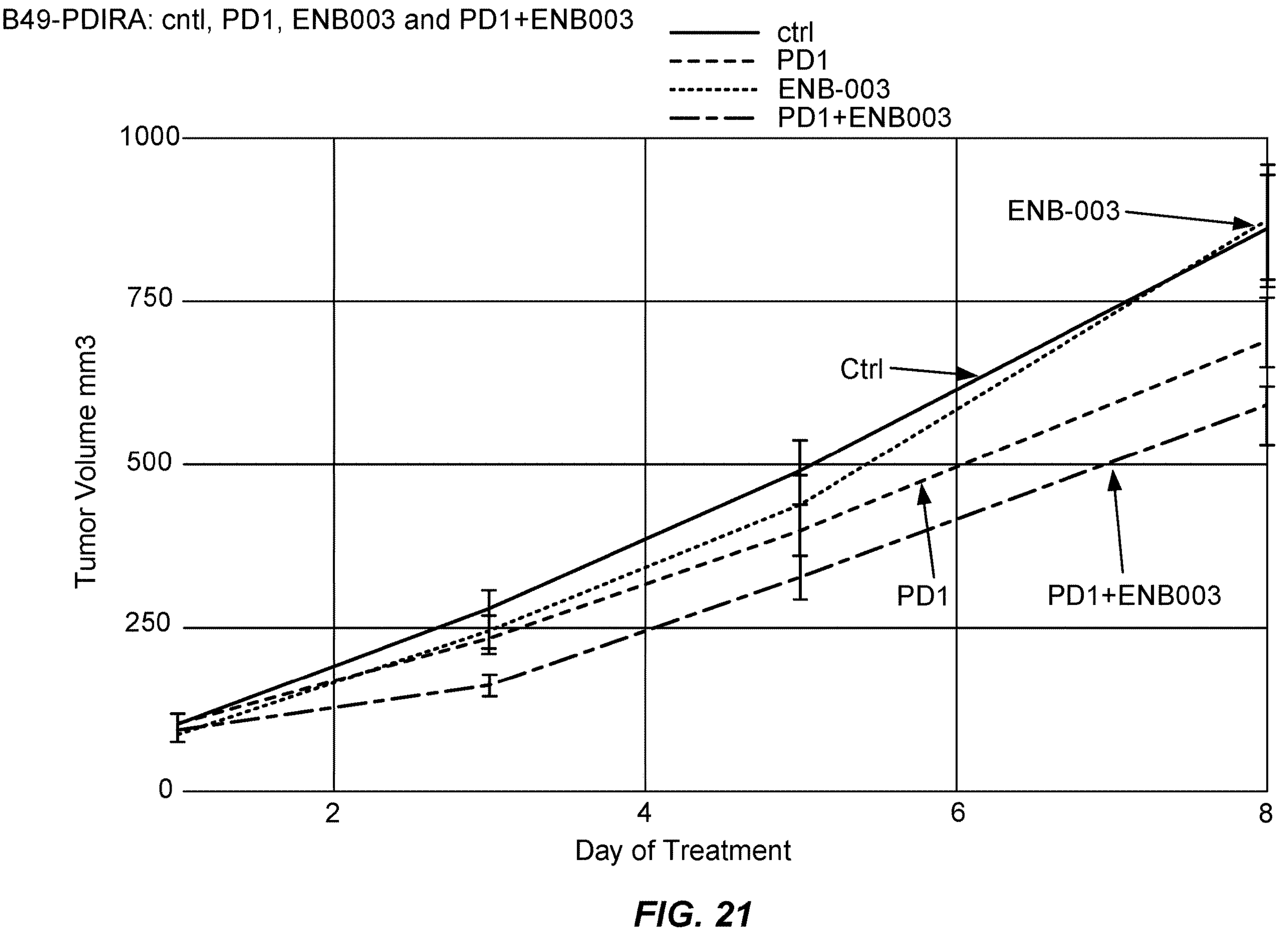
FIG. 21 illustrates tumor volume measurements of a syngeneic bladder cancer murine model plotted against days of treatment. Tumor bearing mice were treated with BQ-788-B (ENB003) and an anti-PD-1 agent, BQ-788-B (ENB003) alone, an anti-PD-1 agent alone, or untreated (ctrl).

Tumor volume measurements show that as compared to control and BQ-788-B ("ENB003") alone or anti-PD-1 alone, the combination treatment of anti-PD-1 and BQ-788-B ("ENB003") yields the greatest anti-bladder cancer treatment efficacy, FIG. 21. The syngeneic bladder cancer murine model shows synergy between anti-PD1 and BQ-788-B ("ENB003") treatment.

Example 6: Syngeneic Bladder Cancer Model Shows Synergy Between Anti-PD1 and BQ-788-B (Compound 1)

6 week old female C57BL/6 mice, n=5 per group, were implanted with bladder cancer tumor cells, MB49-PDIRA-220 at the right flank. When tumors reached from about 25 $mm^3$-50 $mm^3$ volume, mice were separated into 4 treatment groups: (1) dosed with 4 μg of BQ-788-B (BQ788) intravenously on days 1, 3, 5, and 8 with 100 μg of an anti-PD-1 agent intraperitoneally on days 1, 4, and 9 (2) dosed with 4 μg of BQ-788-B (BQ788) intravenously on days 1, 3, 5, and 8 (3) dosed with 100 μg of an anti-PD-1 agent intraperitoneally on days 1, 4, and 9 or (4) untreated control. Tumor volume measurements were taken 3 times per week. The study was terminated on day 12 due to morbidity of control groups.

Figure 22:
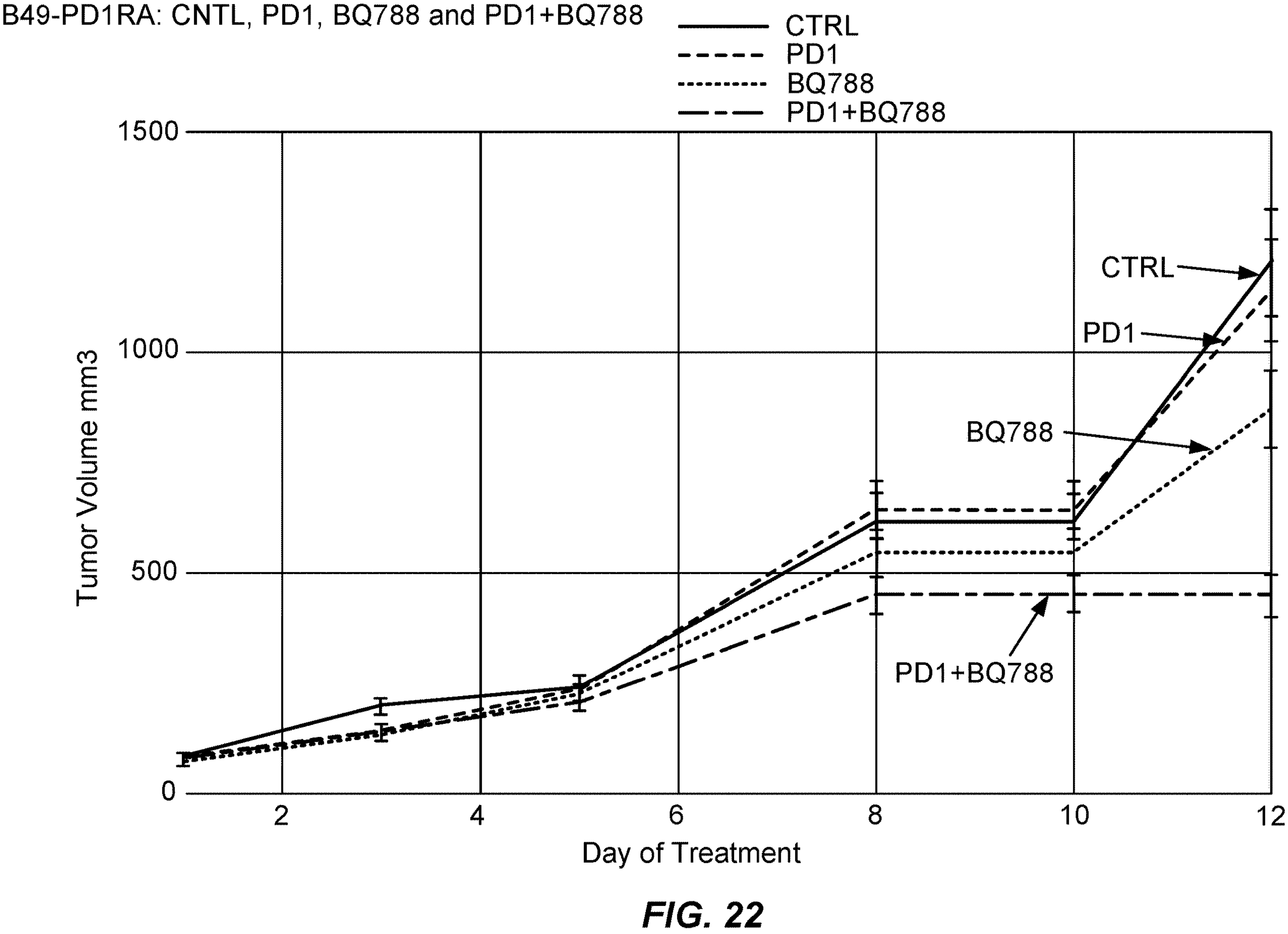
FIG. 22 illustrates tumor volume measurements of a syngeneic bladder cancer murine model plotted against days of treatment. Tumor bearing mice were treated with BQ-788-B (BQ788) and an anti-PD-1 agent, BQ-788-B (BQ788) alone, an anti-PD-1 agent alone, or untreated (ctrl).

Tumor volume measurements show that as compared to control and BQ-788-B ("BQ788") alone or anti-PD-1 alone, the combination treatment of anti-PD-1 and BQ-788-B ("BQ788") yields the greatest anti-bladder cancer treatment efficacy, FIG. 22. The syngeneic bladder cancer murine model shows synergy between anti-PD1 and BQ-788-B ("BQ788") treatment.

While some embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating urothelial cancer in a subject in need thereof, comprising administering to said subject:

(a) an endothelin B receptor (ETBR) antagonist having the structure:

Compound (1)

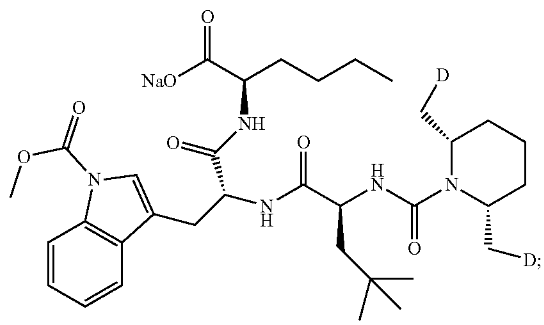

and (b) an anti-PD1 antibody, wherein said administering is effective to treat said urothelial cancer in said subject.

2. The method of claim 1, wherein a greater reduction in volume of said urothelial cancer is observed in said subject upon administration of said anti-PD1 antibody and said ETBR antagonist as compared to the reduction in volume of said urothelial cancer upon individual administration of said ETBR antagonist or said anti-PD1 antibody.

3. The method of claim 1, wherein extended survival of said subject is observed upon administration of said anti-PD1 antibody and said ETBR antagonist as compared to the survival of said subject upon individual administration of said ETBR antagonist or said anti-PD1 antibody.

4. The method of claim 1, wherein the ETBR antagonist and the anti-PD1 antibody are administered sequentially.

5. The method of claim 1, wherein the ETBR antagonist and the anti-PD1 antibody are administered simultaneously.

6. The method of claim 1, wherein the subject has a urothelial cancer selected from bladder cancer, ureter cancer, renal pelvic cancer, and any combination thereof.

7. The method of claim 6, wherein said urothelial cancer is bladder cancer.

8. The method of claim 1, wherein the anti-PD1 antibody is pidilizumab, nivolumab, or pembrolizumab.

9. The method of claim 8, wherein the anti-PD1 antibody is pembrolizumab.

10. The method of claim 1, wherein the daily dose of ETBR antagonist is about 100 μg to about 4000 μg.

11. The method of claim 1, further comprising administering to the subject an additional therapeutic agent.

12. The method of claim 11, wherein the additional therapeutic agent is an anti-oncologic selected from a bRAF inhibitor, a caspase-8 inhibitor, an endothelin A receptor (ETAR) antagonist, niacinamide, a chemotherapeutic agent, or any combination thereof.

13. The method of claim 11, wherein the ETBR antagonist is administered 3 times about every 2-3 weeks and the additional therapeutic agent is administered 1 time about every 2-3 weeks.

14. The method of claim 13, wherein the ETBR antagonist is administered 3 times about every 21 days and the additional therapeutic agent is administered 1 time about every 21 days.

* * * * *